United States Patent
Py et al.

(10) Patent No.: US 7,331,944 B2
(45) Date of Patent: Feb. 19, 2008

(54) OPHTHALMIC DISPENSER AND ASSOCIATED METHOD

(75) Inventors: Daniel Py, Stamford, CT (US);
Norbert M. Assion, Shelton, CT (US);
Julian V. Chan, Spring Valley, NY (US); Joseph M. Ting, Sudbury, MA (US)

(73) Assignee: Medical Instill Technologies, Inc., New Milford, CT (US)

( * ) Notice: Subject to any disclaimer, the term of this patent is extended or adjusted under 35 U.S.C. 154(b) by 365 days.

(21) Appl. No.: 10/691,270

(22) Filed: Oct. 21, 2003

(65) Prior Publication Data

US 2005/0029307 A1    Feb. 10, 2005

Related U.S. Application Data

(63) Continuation-in-part of application No. 10/001,745, filed on Oct. 23, 2001, now Pat. No. 6,761,286.

(60) Provisional application No. 60/443,524, filed on Jan. 28, 2003, provisional application No. 60/420,334, filed on Oct. 21, 2002, provisional application No. 60/242,974, filed on Oct. 24, 2000, provisional application No. 60/242,595, filed on Oct. 23, 2000.

(51) Int. Cl.
*A61M 35/00* (2006.01)
*B67D 5/064* (2006.01)

(52) U.S. Cl. .................. 604/298; 222/321.2; 222/325; 222/631; 222/321.8; 222/420; 222/162

(58) Field of Classification Search ............. 222/321.2, 222/420, 325, 631, 322, 321.8, 464.7, 321.6; 604/298
See application file for complete search history.

(56) References Cited

U.S. PATENT DOCUMENTS 1,471,091 A    10/1923    Bessesen (Continued)

FOREIGN PATENT DOCUMENTS

EP    0802827 B1    8/1998

OTHER PUBLICATIONS

International Search Report of PCT Application No. PCT/US03/33503 Dated Dec. 1, 2004.
U.S. Appl. No. 10/640,500, filed Aug. 13, 2003, Py et al.
U.S. Appl. No. 60/403,484, filed Aug. 13, 2002, Py.

*Primary Examiner*—Kevin Shaver
*Assistant Examiner*—Melvin A. Cartagena
(74) *Attorney, Agent, or Firm*—McCarter & English, LLP

(57) ABSTRACT

An ophthalmic dispenser has a rigid housing defining a fluid-receiving chamber, a flexible bladder receivable within the fluid-receiving chamber, a pump coupled in fluid communication with the fluid-receiving chamber, and a nozzle having a valve defining an annular, axially-extending valve seat, an outlet aperture coupled in fluid communication between the valve seat and the pump, and a flexible valve cover extending about the valve seat and forming an annular, axially-extending interface therebetween. The valve interface is connectable in fluid communication with the outlet aperture, and at least part of the valve cover is movable between (i) a normally closed position with the valve cover engaging the valve seat to close the interface and form a fluid-tight seal therebetween, and (ii) an open position with at least part of the valve cover spaced away from the valve seat in response to pumped fluid flowing through the outlet aperture at a pressure greater than a valve opening pressure to allow the passage of pressurized fluid therebetween. A spring is drivingly connected to the housing and moves at least one of the pump and housing relative to the other to actuate the pump. The rigid housing is mountable within a cartridge which, in turn, is mountable within a dispenser housing including an eyelid depressor and a trigger for simultaneously actuating the eyelid depressor and pump.

36 Claims, 62 Drawing Sheets

U.S. PATENT DOCUMENTS

| | | |
|---|---|---|
| 3,698,595 A | 10/1972 | Gortz et al. |
| 3,921,333 A | 11/1975 | Clendinning et al. ........... 47/37 |
| 3,993,069 A | 11/1976 | Buckles et al. .......... 128/214 F |
| 4,023,607 A | 5/1977 | Jensen et al. ................... 150/1 |
| 4,233,262 A | 11/1980 | Curto ......................... 264/509 |
| 4,240,465 A | 12/1980 | Rader ...................... 137/564.5 |
| 4,264,018 A | 4/1981 | Warren ........................ 222/95 |
| 4,425,698 A | 1/1984 | Petrie |
| 4,479,989 A | 10/1984 | Mahal .......................... 428/35 |
| 4,482,585 A | 11/1984 | Ohodaira et al. ............. 428/35 |
| 4,501,781 A | 2/1985 | Kushida et al. ............... 428/35 |
| 4,578,295 A | 3/1986 | Jabarin ......................... 428/35 |
| 4,579,757 A | 4/1986 | Su et al. ....................... 428/35 |
| 4,603,066 A | 7/1986 | Jabarin ......................... 428/35 |
| 4,636,412 A | 1/1987 | Field ............................ 428/35 |
| 4,700,838 A | 10/1987 | Falciani et al. ............. 206/438 |
| 4,704,510 A | 11/1987 | Matsui ................ 219/10.55 E |
| 4,784,652 A | 11/1988 | Wikström ................... 604/295 |
| 4,854,481 A | 8/1989 | Bohl et al. .................... 222/94 |
| 4,859,513 A | 8/1989 | Gibbons et al. ........... 428/34.2 |
| 4,880,675 A | 11/1989 | Mehta ....................... 428/35.7 |
| 4,910,147 A | 3/1990 | Bacehowski et al. ....... 435/296 |
| 4,921,733 A | 5/1990 | Gibbons et al. ........... 428/34.2 |
| 4,981,479 A | 1/1991 | Py ............................. 604/302 |
| 5,102,705 A | 4/1992 | Yammoto et al. ........ 428/36.92 |
| 5,238,153 A | 8/1993 | Castillo et al. ............. 222/189 |
| 5,263,946 A | 11/1993 | Klug .......................... 604/327 |
| 5,267,986 A | 12/1993 | Py ............................. 604/294 |
| 5,320,845 A | 6/1994 | Py ............................. 424/427 |
| 5,366,108 A | 11/1994 | Darling ........................... 222/1 |
| 5,401,259 A * | 3/1995 | Py ............................. 604/294 |
| 5,419,465 A | 5/1995 | Schroeder ................ 222/386.5 |
| 5,429,254 A | 7/1995 | Christine ................... 215/11.1 |
| RE35,187 E | 3/1996 | Gortz ......................... 222/105 |
| D368,774 S | 4/1996 | Py ............................. D24/113 |
| D374,719 S | 10/1996 | Py ............................. D24/120 |
| 5,562,960 A | 10/1996 | Sugiura et al. ............. 428/35.7 |
| 5,565,160 A | 10/1996 | Makuuchi et al. .......... 264/485 |
| 5,613,957 A | 3/1997 | Py ............................. 604/294 |
| 5,615,795 A | 4/1997 | Tipps ......................... 220/410 |
| 5,641,004 A | 6/1997 | Py ................................. 141/3 |
| 5,665,079 A * | 9/1997 | Stahl ......................... 604/294 |
| 5,676,267 A | 10/1997 | Slat et al. .................. 215/12.1 |
| 5,685,869 A | 11/1997 | Py ............................. 604/294 |
| 5,687,882 A | 11/1997 | Mueller ..................... 222/212 |
| 5,746,728 A | 5/1998 | Py ............................. 604/298 |
| 5,780,130 A | 7/1998 | Hansen et al. ............. 428/35.7 |
| 5,803,311 A | 9/1998 | Fuchs ......................... 222/105 |
| 5,804,236 A | 9/1998 | Frisk .......................... 426/106 |
| 5,816,772 A | 10/1998 | Py ............................. 414/786 |
| 5,875,931 A | 3/1999 | Py ............................. 222/137 |
| 5,931,386 A | 8/1999 | Jouillat ....................... 239/463 |
| 5,944,702 A | 8/1999 | Py ............................. 604/298 |
| RE36,410 E | 11/1999 | Meshberg ...................... 141/2 |
| 6,033,384 A | 3/2000 | Py ............................. 604/186 |
| 6,062,430 A | 5/2000 | Fuchs ......................... 222/105 |
| 6,189,739 B1 * | 2/2001 | von Schuckmann ........ 222/182 |
| 6,254,579 B1 * | 7/2001 | Cogger et al. .............. 604/298 |
| 6,343,713 B1 | 2/2002 | Abplanalp ................... 222/95 |
| 6,419,124 B1 * | 7/2002 | Hennemann et al. .... 222/321.6 |
| 6,423,040 B1 * | 7/2002 | Benktzon et al. ........... 604/300 |
| 6,478,196 B2 * | 11/2002 | Fuchs ...................... 222/321.6 |
| 6,524,287 B1 * | 2/2003 | Cogger ....................... 604/298 |
| 6,604,561 B2 | 8/2003 | Py ............................. 141/329 |
| 2003/0089743 A1 | 5/2003 | Py et al. ..................... 222/386 |

* cited by examiner

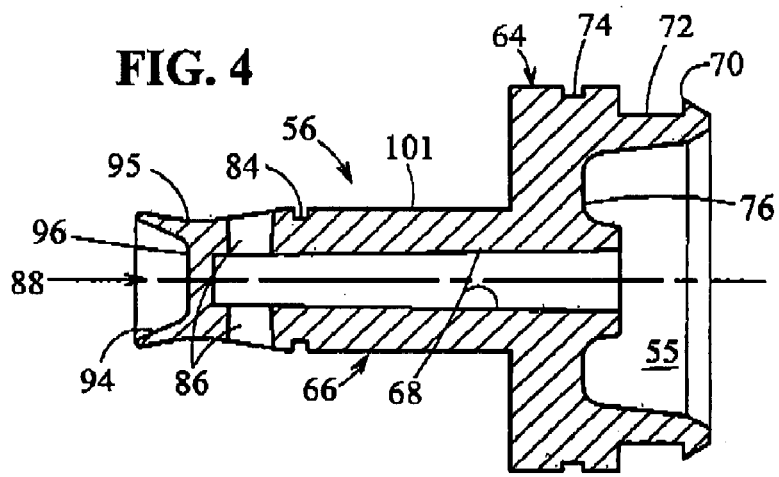
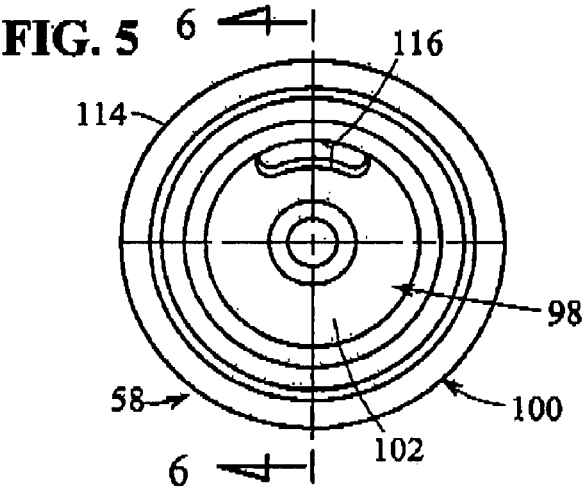
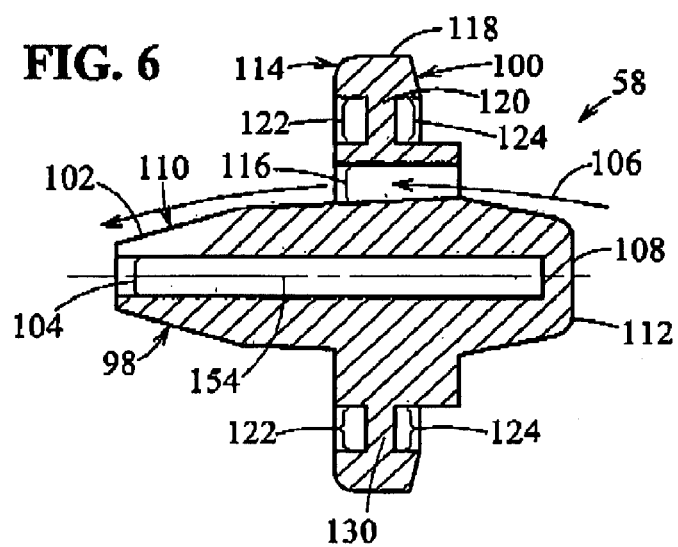

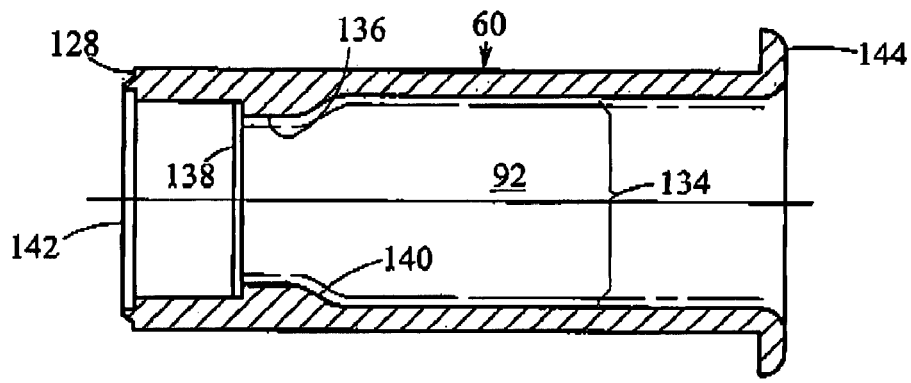
FIG. 7
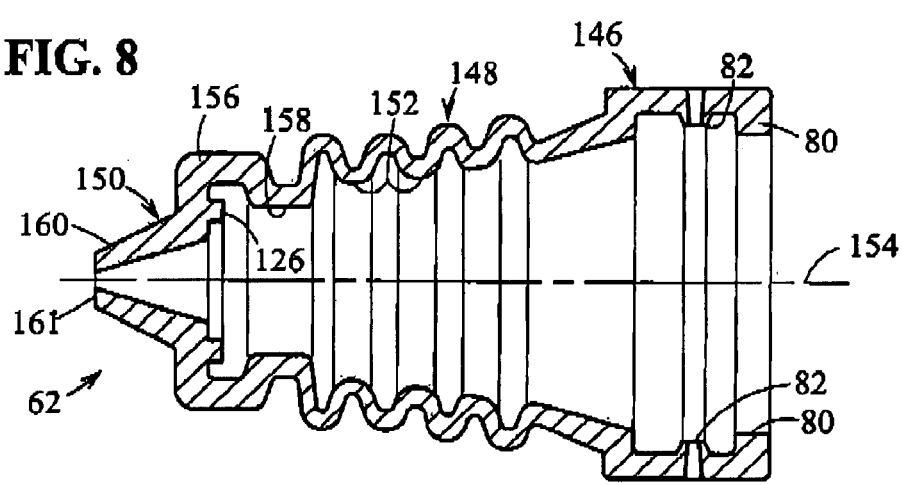
FIG. 8
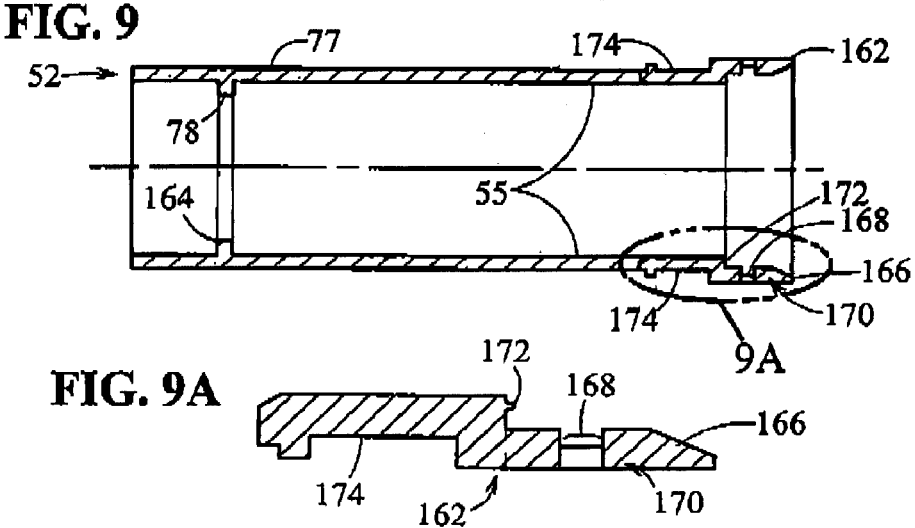
FIG. 9
FIG. 9A

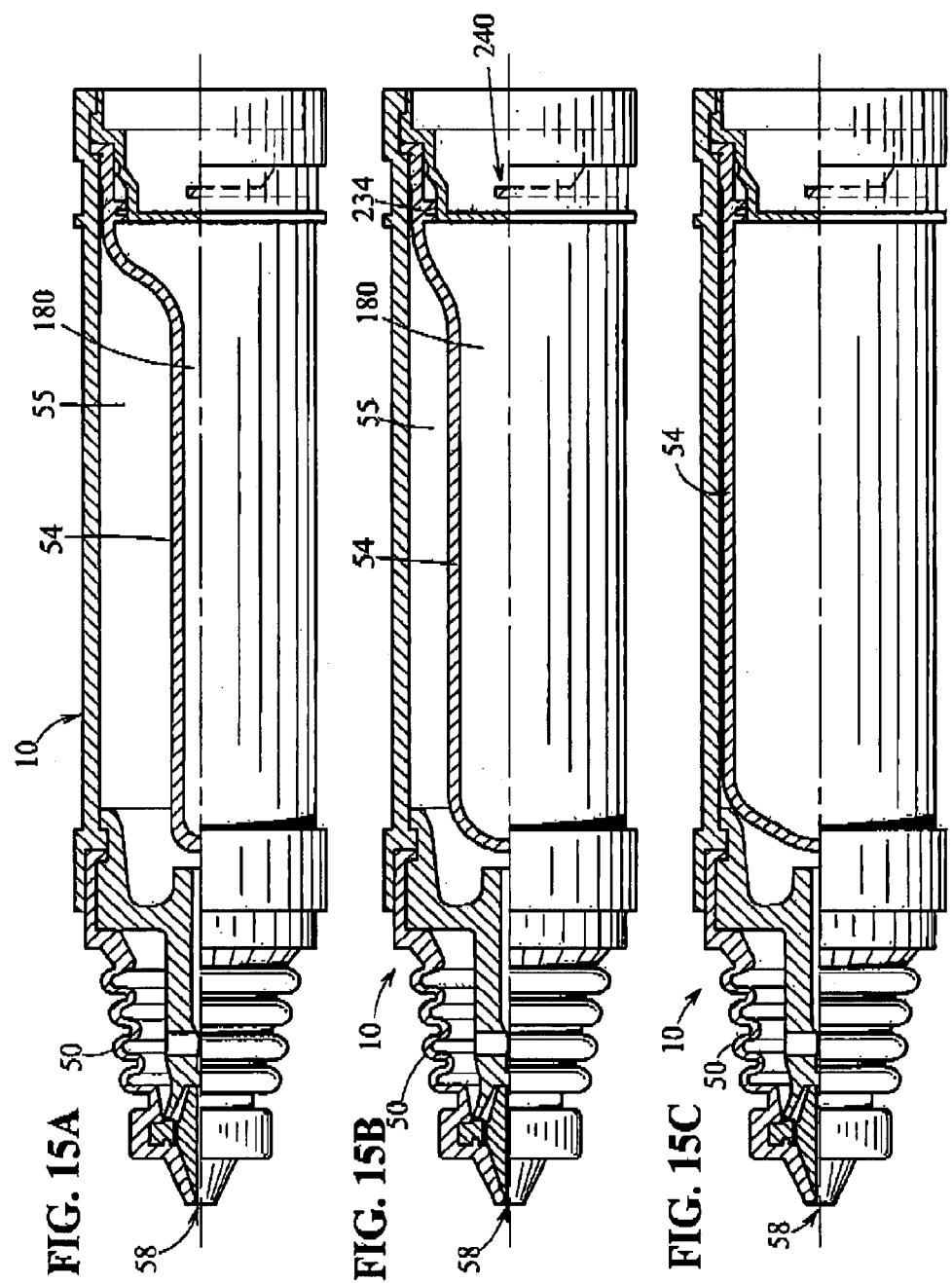

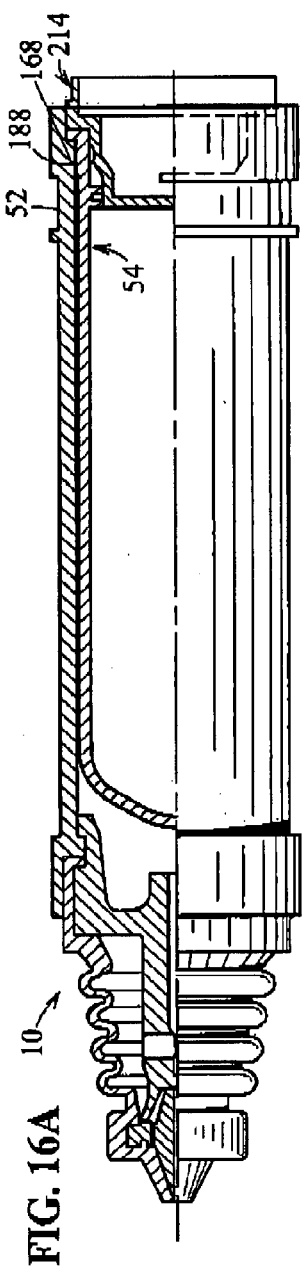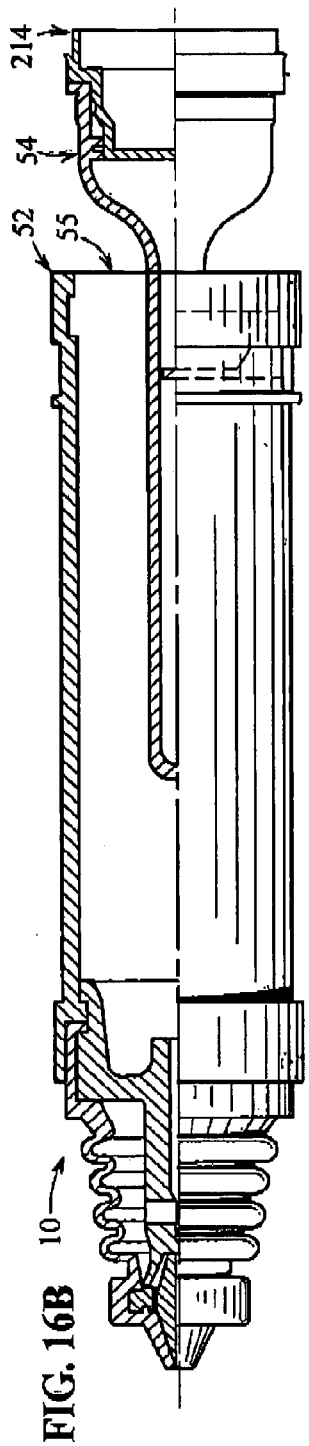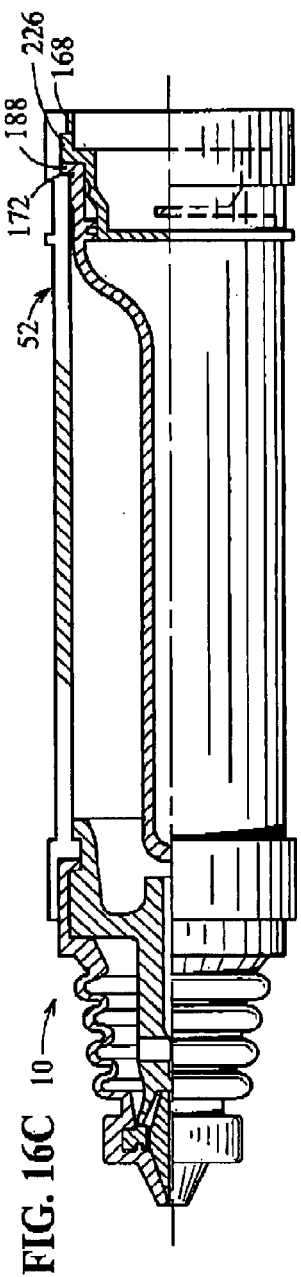

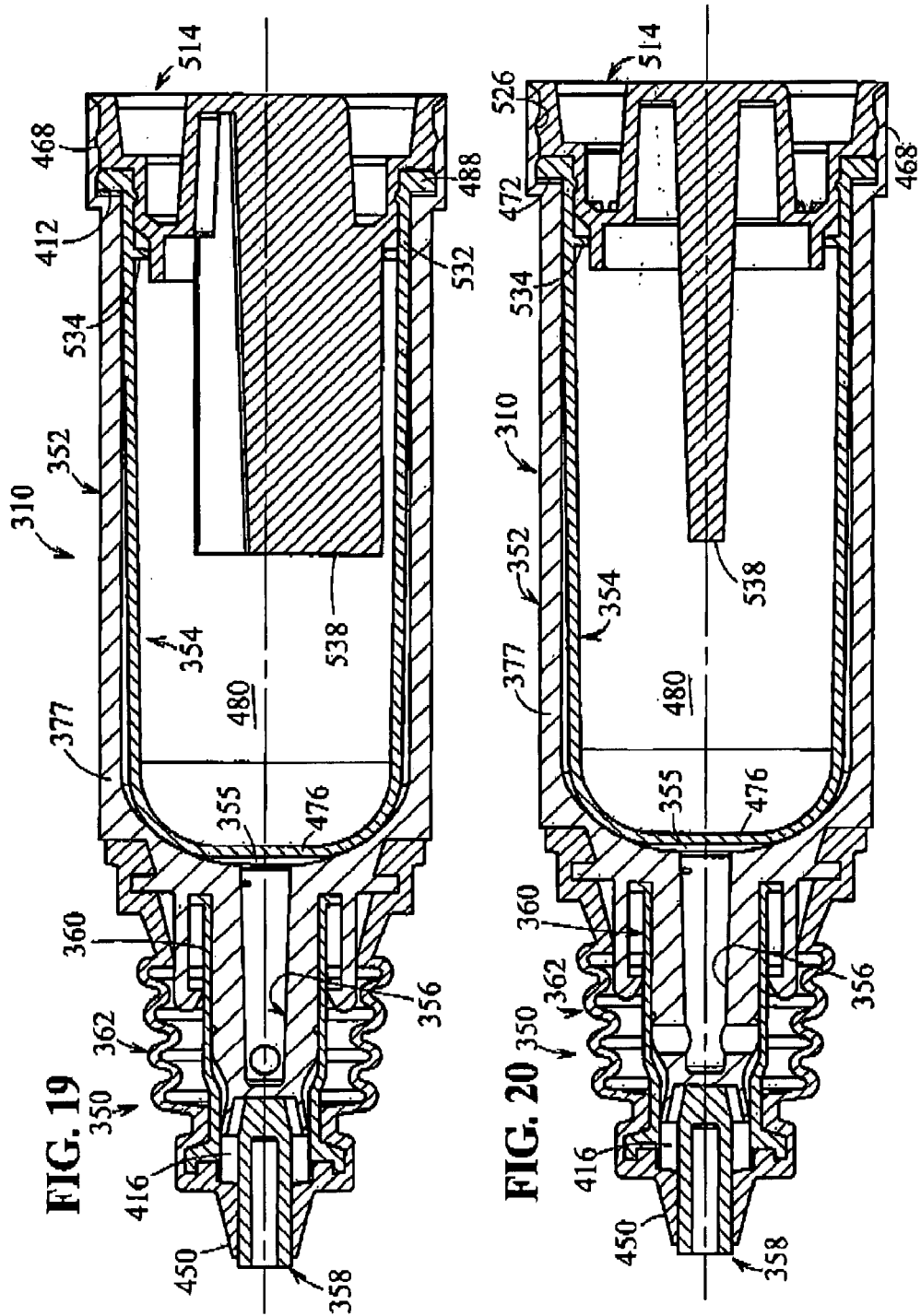

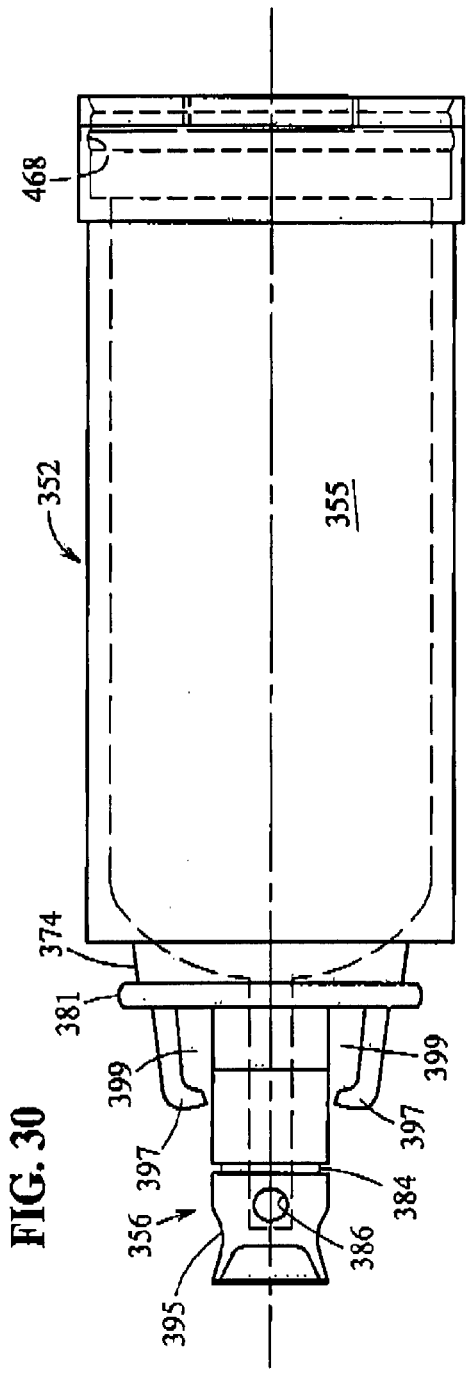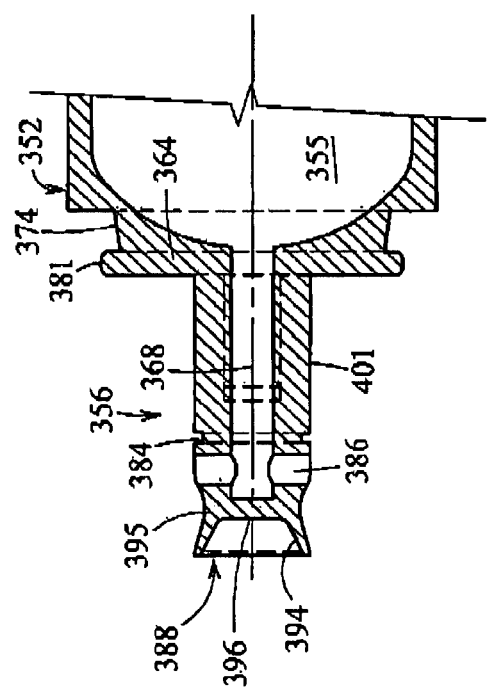

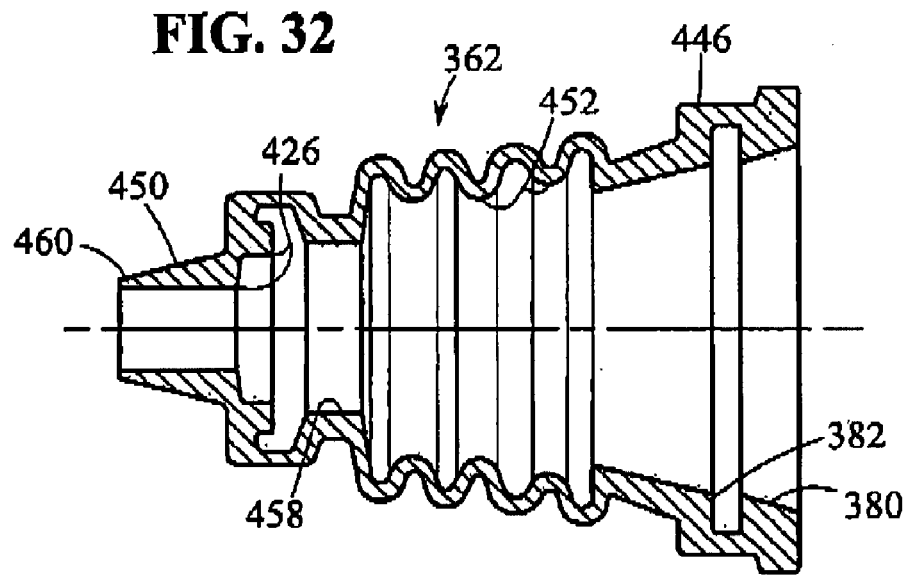

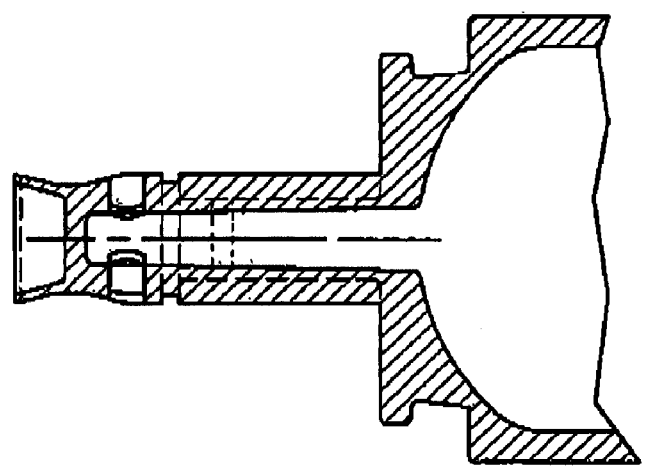
FIG.39D 1052/1056

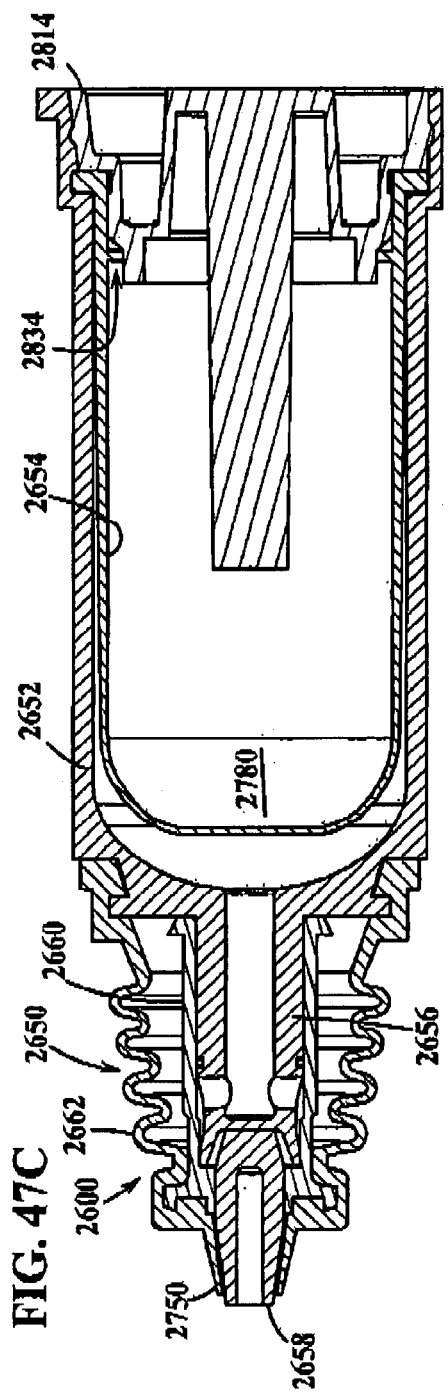
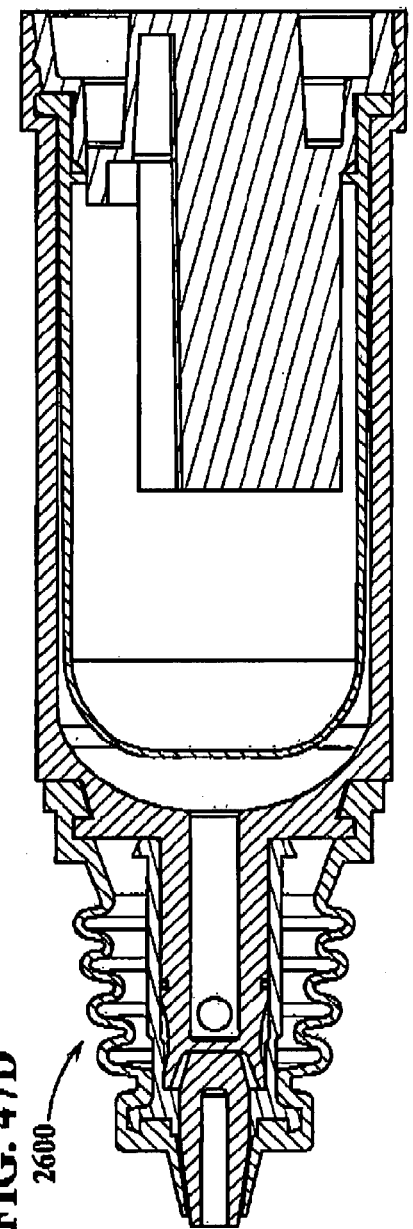
FIG. 47C
FIG. 47D

OPHTHALMIC DISPENSER AND ASSOCIATED METHOD

CROSS-REFERENCE TO RELATED APPLICATIONS

This patent application is a continuation-in-part of U.S. patent application Ser. No. 10/001,745, filed Oct. 23, 2001, now U.S. Pat. No. 6,761,286 entitled "Fluid Dispenser Having A Rigid Vial And Flexible Inner Bladder", which claims the benefit of similarly-entitled U.S. Provisional Application Ser. No. 60/242,595, filed Oct. 23, 2000, and U.S. Provisional Application Ser. No. 60/242,974, filed Oct. 24, 2000, each of which is hereby expressly incorporated by reference as part of the present disclosure. This patent application also claims the benefit of U.S. Provisional Application Ser. No. 60/443,524, filed Jan. 28, 2003, entitled "Fluid Dispenser Having A Rigid Vial And Flexible Inner Bladder", and similarly-entitled U.S. Provisional Patent Application Ser. No. 60/420,334, filed Oct. 21, 2002, each of which is hereby expressly incorporated by reference as part of the present disclosure.

FIELD OF THE INVENTION

The present invention relates generally to dispensers and to methods for storing and dispensing fluids or other substances, and to methods for manufacturing, distributing, and/or selling such dispensers, including but not limited to, dispensers having a rigid vial, a flexible bladder disposed within the rigid vial and defining a chamber between the flexible bladder and rigid vial for receiving therein a fluid or other substance, and a nozzle and pump assembly coupled in fluid communication with chamber for dispensing fluids or other substances therefrom.

BACKGROUND INFORMATION

Typical fluid dispensers include a container defining therein a chamber for receiving a fluid to be dispensed, a nozzle and pump assembly mounted on the container, and a dip tube extending downwardly from the nozzle into the chamber for pumping the fluid from the bottom of the chamber, through the dip tube, and out of the dispenser. Other known dispensers include a vial and a flexible bladder received within the vial. For example, U.S. Pat. No. 6,062,430 to Fuchs shows in FIG. 1 a dispensing container with variable volume compensation including a bottle-shaped vessel 2 in the form of a thin-walled, hollow body made from soft elastic plastic, and a reception container 15 formed of a wrinkle film encapsulated within the vessel body 2.

One of the drawbacks associated with typical prior art fluid dispensers is that the fluid chamber(s) are not maintained in a substantially airless condition throughout the storage, shelf life and/or usage of the dispenser. For example, the nozzles and/or valves used in typical prior art dispensers frequently are incapable of maintaining the dispenser in a hermetically sealed condition. Such nozzles and/or valves allow the passage of air or other gases therethrough and into contact with the medicament or other substance contained within the fluid chamber(s). In addition, such nozzles and/or valves frequently allow vapor loss therethrough either during the storage, shelf life or usage of the dispensers.

Another drawback associated with prior art dispensers is that the materials of construction may undergo creep that, in turn, causes seals formed within the dispensers to leak. Many medicaments are maintained in storage and/or on store shelves for at least several, and in some instances, many months. During transportation and storage, the dispensers can be subjected to varying atmospheric conditions involving large variations in atmospheric temperature, pressure and/or humidity. As a result, the dispensers are frequently subjected to substantial differential thermal expansion and/or contraction that, in turn, cause the materials of construction to undergo creep. The seals and other components of such prior art dispensers typically are not designed to address such creep, and as a result, the dispensers develop leaks or otherwise allow air ingress and/or vapor loss when subjected to such long periods of storage or varying atmospheric conditions. For example, some polyethylene dispensers have been known to lose between about 10% to about 25% of the weight of their contents during storage. Such weight loss is believed to be due to vapor loss from the medicament or other fluid-containing chambers through the polyethylene walls of the dispensers and/or through leaks otherwise created in the seals or other structural interfaces of the containers. The vapor loss is typically offset by air ingress into the chambers. Vapor loss and/or air ingress is particularly problematic for dispensers containing medicaments, such as pharmaceutical preparations or vaccines, because they tend to dilute each predetermined dosage of the medicament dispensed from the container, and/or cause the dispenser to dispense inconsistent concentrations of medicament from one dose to the next.

Yet another disadvantage associated with prior art dispensers is that because they cannot reliably maintain the medicament or other substance contained therein in an airtight condition, they cannot be used for either multiple dose applications or preservative-free formulations. The use of single dose dispensers can be substantially more expensive than multiple dose dispensers. In addition, the preservatives used in many medicaments, such as pharmaceutical preparations and vaccines, can cause adverse reactions in patients and/or dilute the effect of the medicament on the patient.

Another drawback of prior art dispensers is that the ullage or "dead space" inherent in such dispensers allows sediment build-up. Many medicaments and other formulations contained within such dispensers are suspensions. The ullage or dead space in the prior art dispensers allows the solutes or other solid components of such suspensions to form sediment therein. Such settling of the suspensions dilutes the medicaments or other substances contained within the dispensers and, in turn, alters the medicament and/or the concentration of medicament in each patient dose.

Another drawback associated with many prior art dispensers is that they can only dispense the medicament or other substance contained therein in an upright or other single orientation. This drawback prevents such dispensers from being used effectively in other orientations, such as upside down. In addition, because such dispensers do not maintain the medicament or other substance contained therein in an airless condition, they cannot be used in low gravity environments, such as outer space.

Dispensers for storing and dispensing fluids (or other substances) are used in a variety of applications. One such application is that of eye treatment. Indeed, numerous dispensers have been developed for dispensing medicament to an eye. Some of these dispensers consist of a flexible vial that dispenses medicament when the side walls of the vial are squeezed. Such dispensers are commonly referred to as "eye droppers". Less common, are dispensers that include a pump type delivery system.

Various difficulties can arise with respect to properly applying medicament to the eye. For example, many people encounter difficulty in applying drops to their eyes. The eye is a very sensitive body part and individuals find it difficult to control reflexive blinking when applying drops thereto. Also, some users have trouble positioning the tip of a dropper bottle over the eye. Others have difficulty holding a dropper bottle steady or encounter difficulty in squeezing a bottle to apply a proper quantity. Moreover, it is often desirable to deliver medicament to a particular region of the eye. For example, when eye drops are applied to the surface of the eyeball, blinking and natural tear flow combine to dispel and/or dilute the medicament thereby limiting its effectiveness. Moreover, some medicaments can cause "redeye" if delivered directly to the cornea area of the eyeball. On the other hand, if the medicament is delivered to the cul-de-sac of the conjunctiva, the medicament is less susceptible to blinking and tear flow and therefore remains effective for a longer period of time.

Some dispensers have features adapted to address one or more of these difficulties. Examples of these types of features are an eyelid cover, an eyelid depressor, a pump type delivery system, and/or a trigger mechanism. The eyelid cover helps the user properly position the dispenser over the eye. The eyelid depressor helps expose the conjunctive cul-de-sac. A pump type delivery system helps deliver the medicament. A trigger mechanism provides the user with a convenient way to activate the delivery system.

One drawback associated with such dispensers is that their cost can be more than otherwise would be desired. Moreover, even those who can afford such dispensers may forgo the extra features in favor of a less costly alternative. Consequently, it would be desirable to enable manufacturers of such dispensers to be able to offer less costly alternative(s) in order to reach all sectors of the market.

Another drawback associated with these dispensers is that they can be bulkier than dispensers without such features, thereby making them less convenient to transport (e.g., carry in a pocket, ship, etc.) than is desired.

Another drawback associated with these types of dispensers is that they are limited in regard to the amount of medicament (or other fluid) that is able to be stored in the dispenser. Although most (if not all dispensers) suffer from this drawback, the cost of certain dispensers may make it impractical to throw them away when empty. Thus, there may be a need to refill the chamber that holds the medicament. In many of these dispensers, the chamber is not readily accessible to the user, and consequently, impractical to refill. Some types of dispensers employ a replaceable cartridge. This solves the refill problem; however, the actuation mechanisms on such dispensers are less convenient to use than is currently desired.

Another drawback associated with many of these types of dispensers is that a vacuum pump is needed in order properly fill and cap the chamber without spillage.

Accordingly, it is an object of the present invention to overcome one or more of the above-described drawbacks or disadvantages of the prior art.

SUMMARY OF THE INVENTION

The present invention is directed to a dispenser for dispensing a fluid. According to one aspect of the present invention, the dispenser comprises a rigid housing, and a flexible bladder mounted within the housing and defining an interior chamber within the flexible bladder, and a fluid-receiving chamber between the flexible bladder and the rigid housing. The dispenser further comprises means for creating a first pressure within the fluid-receiving chamber greater than a second pressure within the interior chamber of the bladder to thereby prevent the ingress of gases or vapors into the fluid-receiving chamber. In a currently preferred embodiment of the present invention, the means for creating the pressure differential is formed by a resilient material of the bladder that flexes the bladder outwardly toward an expanded condition, and thereby creates the first pressure within the fluid-receiving chamber greater than the second pressure in the interior chamber of the bladder. Preferably, the resilient bladder is molded in the expanded condition, and therefore the resilient bladder will inherently tend to force itself into the expanded condition and thereby create the desired pressure differential between the fluid-receiving chamber and the interior chamber of the bladder.

One embodiment of the dispenser further comprises a pump coupled in fluid communication with the fluid-receiving chamber for pumping a fluid received therein from the dispenser; and a one-way valve coupled in fluid communication with the pump for allowing the passage of the pumped fluid therethrough and preventing the passage of fluids in the opposite direction. The one-way valve is preferably formed by a nozzle, and a flexible cover overlying the nozzle and creating the one-way valve at the interface of the nozzle and cover.

According to another aspect of the present invention, the dispenser further comprises a seal formed between the flexible bladder and the rigid vial for sealing the fluid-receiving chamber. The seal includes a first protuberance extending radially outwardly on an outer surface of the flexible bladder, and a second protuberance axially spaced relative to the first protuberance and extending radially inwardly on an inner surface of the bladder. The first and second protuberances are subject to radial compression to seal the interface between the flexible bladder and rigid vial. Preferably, the first protuberance extends about an outer peripheral surface of the bladder and defines an outer annular sealing surface, and the second protuberance extends about an inner peripheral surface of the bladder and defines an inner annular sealing surface. In addition, the first protuberance defines a tapered surface for directing bladder material in approximately the direction of the second protuberance to thereby facilitate maintaining a fluid-tight seal in the event of bladder material creep. The seal preferably further includes a peripheral flange extending about an open end of the flexible bladder and subject to axial compression for further sealing the interface between the bladder and rigid vial.

According to another aspect of the present invention, the dispenser further comprises a plug receivable within an open end of the rigid vial and engageable with at least one of the first and second protuberances for radially compressing the protuberances to seal the interface between the flexible bladder and rigid vial. The plug defines at least one aperture therethrough in fluid communication with the interior chamber of the flexible bladder. Preferably, a two-way valve of the dispenser is coupled in fluid communication between the interior chamber of the flexible bladder and the aperture of the plug for preventing fluid communication between the interior chamber of the bladder and the ambient atmosphere when a pressure differential across the two-way valve is less than a threshold level. The two-way valve preferably is formed by a flexible, annular protuberance extending radially inwardly from an inner peripheral surface of the flexible bladder, and engageable with an annular surface of the plug to thereby seal the interface between the flexible bladder and plug. In one embodiment of the present invention, the annular protuberance defines axially-opposed surfaces that taper inwardly in the radial direction to facilitate flexing of the protuberance in response to the pressure differential across the protuberance exceeding the predetermined threshold level.

The flexible bladder of the dispenser further defines an open end and a closed end, and is movable between a collapsed condition and an expanded condition. Upon expansion of the flexible bladder from the collapsed condition into the expanded condition, the flexible bladder and rigid vial define an annular gap therebetween. In one embodiment, the annular gap defines an increasing width in the axial direction from the open end toward the closed end of the flexible bladder, to facilitate removal of fluid from the fluid-receiving chamber upon expansion of the bladder. Preferably, the flexible bladder initially contacts the rigid vial adjacent to or near the open end of the bladder, and then progressively engages the rigid vial in the axial direction from the open end toward the closed end of the flexible bladder with further expansion thereof. Also in accordance with one embodiment of the dispenser, the flexible bladder defines an external morphology in an expanded condition, the rigid vial defines an internal morphology, and the external and internal morphologies are substantially the same to thereby allow the flexible bladder to conformably contact the rigid vial and substantially eliminate any dead space in the fluid-receiving chamber therebetween.

In accordance with another aspect of the present invention, the pump of the dispenser comprises a piston, and a slide for slidably receiving the piston therein. At least one of the piston and the slide is reciprocable relative to the other. In addition, the piston is made of a relatively hard material, the slide is made of a relatively soft material, and the piston causes a compression zone of the slide to flex outwardly upon moving at least one of the piston and the slide relative to the other to thereby effect a fluid-tight seal between the piston and slide. In addition, forming the slide from a relatively flexible material allows the slide to be formed integral with a nozzle, such as by molding the two components in a single part, wherein the integral nozzle and slide may be released from a core pin by injecting pressured air therebetween.

In accordance with another aspect of the present invention, the dispenser further comprises means for controlling the flexible bladder to collapse into a predetermined collapsed condition. In one embodiment of the present invention, the means for controlling includes a plurality of legs extending axially inwardly into the interior chamber of the flexible bladder for conformably contacting the flexible bladder upon collapse thereof. In another embodiment of the present invention, the means for controlling is defined by at least one axially elongated surface discontinuity formed in the flexible bladder.

In accordance with another embodiment of the present invention, the flexible bladder is capable of being penetrated by a needle or like injection member for introducing a predetermined substance into the fluid-receiving chamber. In this embodiment, the flexible may bladder include a first portion substantially infusible in response to the application of thermal energy thereto and compatible with the substance to be received within the fluid-receiving chamber, and a second portion overlying the first portion and fusible in response to the application of thermal energy thereto. Thus, the second portion enables the formation of a substantially fluid-tight seal between the flexible bladder and fluid-receiving chamber in a region thereof penetrated by the needle or like injection member. In one embodiment of the present invention, the second portion is formed of either a thermoplastic or an elastomeric material, and the bladder, including the first portion thereof, is formed of vulcanized rubber. Alternatively, the entire penetrable portion of the flexible bladder is formed of a thermoplastic material that is heat resealable to hermetically seal the aperture formed by the needle or other injection member by applying laser radiation at a predetermined wavelength and power thereto.

According to another aspect of the present invention, a dispenser for storing and dispensing a fluid includes a housing, a first actuator coupled to the housing, and a self contained cartridge. The self contained cartridge includes a vial, the vial including an interior fluid receiving chamber defined therein; a pump in fluid communication with the fluid receiving chamber for pumping a fluid received therein from the dispenser; a nozzle disposed in fluid communication with the pump for allowing the passage of the pumped fluid therethrough; and a casing that retains the nozzle, the pump, and the vial arranged in that order along a longitudinal axis moving in a direction toward a posterior end of the dispenser. The casing includes an anterior wall with an aperture for receiving the nozzle; and a second actuator is coupled to the casing and is responsive to the first actuator. The second actuator has at least a portion disposed outside the casing and at least a portion disposed internal to the casing and operatively coupled to at least one of the pump and the vial. In a first phase of actuation of the actuator, at least one of the pump and the vial moves along the longitudinal axis in a direction toward the other, and in a second phase of actuation by the actuator, at least one of the pump and the vial moves in a direction away from the other.

According to another aspect of the present invention, a method comprises the following steps: providing a plurality of cartridges for storing and dispensing fluid, the plurality of cartridges being substantially identical to one another and each having a vial, a pump, and a nozzle, the vial including an interior fluid receiving chamber defined therein, the pump being in fluid communication with the fluid receiving chamber for pumping a fluid received therein from the dispenser, the nozzle being disposed in fluid communication with the pump for allowing the passage of the pumped fluid therethrough, the cartridge further having a casing that retains the nozzle, the pump, and the vial arranged in that order along a longitudinal axis moving in a direction toward a posterior end of the cartridge, and an actuator operatively coupled to the pump; installing at least one of the plurality of cartridges in a dispenser having an actuator to operatively couple to the cartridge, wherein actuation of the actuator initiates dispensing; and using at least one of the cartridges to dispense fluid without installing the cartridge in a dispenser having an actuator to operatively couple to the cartridge.

According to another aspect of the present invention, a method comprises the following steps: providing a plurality of cartridges for storing and dispensing fluid, the plurality of cartridges being substantially identical to one another and each having a vial, a pump, and a nozzle, the vial including an interior fluid receiving chamber defined therein, the pump being in fluid communication with the fluid receiving chamber for pumping a fluid received therein from the dispenser, the nozzle being disposed in fluid communication with the pump for allowing the passage of the pumped fluid therethrough, the cartridge further having a casing that retains the nozzle, the pump, and the vial arranged in that order along a longitudinal axis moving in a direction toward a posterior end of the cartridge, and an actuator operatively coupled to the pump; providing a plurality of dispensers adapted to receive and operate the cartridges, the plurality of cartridges being substantially identical to one another and being capable of operation as a stand alone unit or in the dispenser; selling at least one of the cartridges in combination with at least one of the dispensers; and selling at least one of the cartridges without a dispenser.

According to another aspect of the present invention, a dispenser for dispensing a fluid comprises: a self contained replaceable cartridge having: a posterior portion including a vial, the vial including an interior fluid receiving chamber defined therein, a pump in fluid communication with the fluid receiving chamber for pumping a fluid received therein from the dispenser; a nozzle disposed in fluid communication with the pump for allowing the passage of the pumped fluid therethrough; a casing that retains the nozzle, the pump, and the posterior portion arranged in that order along a longitudinal axis moving in a direction toward a posterior end of the dispenser, the pump being operationally coupled to at least a portion of the posterior portion to move along the longitudinal axis in concert with movement of said portion of the posterior portion along said axis, the casing having an anterior wall with an aperture for receiving the nozzle; and an actuator operatively coupled to at least a portion of the posterior portion, wherein in a first phase of actuation, the actuator moves at least a portion of the posterior portion along the longitudinal axis in a direction toward the posterior end of the casing and thereby causes the pump to move in the same direction, and in a second phase of actuation, the posterior portion moves along the longitudinal axis in a direction toward the anterior end of the casing and thereby causes the pump to move in a direction toward the anterior end of the casing.

According to another aspect of the present invention, a dispenser for dispensing a fluid comprises: a cartridge having: a vial, the vial including an interior fluid receiving chamber defined therein, a pump in fluid communication with the fluid receiving chamber for pumping a fluid received therein from the dispenser; a nozzle disposed in fluid communication with the pump for allowing the passage of the pumped fluid therethrough; a spring portion disposed posterior to said interior fluid receiving chamber defined therein, a casing that retains the nozzle, the pump, and the vial arranged in that order along a longitudinal axis moving in a direction toward a posterior end of the dispenser, the casing having an anterior wall with an aperture for receiving the nozzle; and an actuator operatively coupled to the pump, wherein in a first phase of actuation, the actuator causes the pump to move along the longitudinal axis in a direction toward the posterior end of the casing thereby applying force to the interior fluid receiving chamber and compressing the spring, and in a second phase of actuation, the compressed spring applies a force to help propel the pump in a direction toward the anterior end of the casing.

According to another aspect of the present invention, a dispenser for dispensing a fluid comprises: a self contained replaceable cartridge having: a vial, the vial including an interior fluid receiving chamber defined therein, a pump in fluid communication with the fluid receiving chamber for pumping a fluid received therein from the dispenser; a nozzle disposed in fluid communication with the pump for allowing the passage of the pumped fluid therethrough; a casing that retains the nozzle, the pump, and the vial arranged in that order along a longitudinal axis moving in a direction toward a posterior end of the dispenser, the casing having an anterior wall with an aperture for receiving the nozzle; and an actuator having a first end and a second end, the first end being pivotably mounted to the casing, the second end being operatively coupled to the pump, the actuator further having a pivoting portion disposed between the first end and the second end.

One advantage of the currently preferred embodiments of the present invention is that the pressure differential between the fluid-receiving chamber and the internal chamber of the bladder and ambient atmosphere substantially prevents the ingress of air or other gases or vapors through the flexible bladder, or otherwise into the fluid-receiving chamber. As a result, the dispensers of the present invention may maintain the medicaments or other substances contained therein in an airless condition throughout substantial periods of storage, shelf life and/or use. Accordingly, the dispensers of the present invention are particularly well suited for dispensing multiple doses of non-preserved medicaments or other substances requiring storage in an airless condition.

Another advantage of the currently preferred embodiments of the present invention is that the seal formed between the flexible bladder and the rigid vial radially and axially directs the material of the flexible bladder to persistently maintain a fluid-tight seal regardless of any creep of the material during the storage or shelf-life of the dispenser. In addition, the one-way valve employed in the preferred embodiments of the present invention further maintains the fluid-receiving chamber in a hermetically-sealed condition throughout the storage, shelf-life and/or use of the dispenser.

Yet another advantage of the dispensers of the present invention is that because the medicament or other substance may be maintained in an airless condition in the fluid-receiving chamber, the dispensers may be used in virtually any orientation, and furthermore, may be used in low gravity environments.

Another advantage of the dispensers of the present invention is that the flexible bladder may define an external morphology substantially matching the internal morphology of the rigid vial. As a result, the flexible bladder may expand and conformably contact the rigid vial throughout the interface between these two parts and, in turn, eliminate any dead space within the fluid-receiving chamber.

Yet another advantage of a currently preferred embodiment of the present invention is that the two-way valve coupled in fluid communication between the interior chamber of the flexible bladder and the ambient atmosphere prevents any exchange of gases or vapors between the interior chamber of the bladder and ambient atmosphere, provided the pressure differential across the valve is less than a predetermined level. As a result, the two-way valve creates a relatively stable micro-atmosphere within the interior chamber of the flexible bladder, thus insulating the interior chamber from fluctuations in pressure and/or humidity in the ambient atmosphere and thereby further preventing the ingress of gas or vapors into the fluid-receiving chamber.

One advantage of a currently preferred embodiment of the present invention is that the replaceable cartridge eliminates the need to return the dispenser to the factory for refilling. The dispenser can be refilled by installing a new cartridge. Moreover, because the cartridge has its own actuator, which is coupled to the actuator on the dispenser, the actuation of the dispenser is improved compared to prior art dispensers with cartridges, and meets the currently desired level of convenience.

Another advantage of a currently preferred embodiment of the present invention is that the presence of an actuator on the cartridge makes the cartridge usable as a dispenser.

Another advantage of a currently preferred embodiment of the present invention is that because the cartridge is usable as a dispenser, the manufacturer can sell the cartridge by itself to reach the sectors of the market that are unable to afford or unwilling to purchase the dispenser.

Another advantage of a currently preferred embodiment of the present invention is that a distributor can stock cartridges and dispensers, sell the cartridge (with or without a dispenser) for use with a dispenser, and sell the cartridge by itself to reach the sectors of the market that are unable to afford or unwilling to purchase the dispenser.

Another advantage of a currently preferred embodiment of the present invention is that the cartridge is less bulky than the dispenser and therefore more convenient to transport (e.g., carry in a pocket, ship, etc.).

One advantage of some embodiments of the present invention is that the actuator has multiple pivot points thereby making it easier to use than previous dispensers.

One advantage of a some embodiments of one aspect of the present invention is that a vacuum pump is not needed in order to fill and cap the chamber without spillage.

Other objects and advantages of the various preferred embodiments of the present invention will become apparent in view of the following detailed description and accompanying drawings.

BRIEF DESCRIPTION OF THE DRAWINGS

FIG. 4 is a central cross-sectional view taken along a longitudinal axis of a piston of the pump assembly of FIG. 1.

FIG. 5 is a front elevational view of a tip of a nozzle of the pump assembly of FIG. 1.

FIG. 6 is a longitudinal cross-sectional view taken along line 6-6 of FIG. 5.

FIG. 7 is a central cross-sectional view taken along a longitudinal axis of a slide or body of the pump assembly of FIGS. 2 and 3 and forming essentially the compression zone.

FIG. 8 is a central cross-sectional view taken along a longitudinal axis of a flexible pump cover of the pump assembly of FIGS. 2 and 3, and illustrating the manner in which the pump cover extends from the tip of the nozzle to the rigid vial and is configured to allow reciprocal movement of the piston connected to the vial.

FIG. 9 is a central, cross-sectional view taken along a longitudinal axis of the rigid vial of the dispenser of FIGS. 2 and 3.

FIG. 9A is an enlarged view of a portion of the vial of FIG. 9 showing a rear mounting portion for receiving the bladder of FIG. 10.

FIGS. 15A-C are sequential side elevational views, partly in section, showing the reduction in volume of fluid and corresponding expansion of the bladder in the full, half-full and empty conditions of the dispenser of FIG. 1, respectively.

FIGS. 16A-C are sequential side elevational views, partly in section, showing the steps of assembling the bladder to the vial during sterilization and filling of the dispenser of FIGS. 2 and 3.

FIG. 19 is a cross-sectional view of the dispenser of FIGS. 17 and 18 taken along line 19-19 of FIG. 18.

FIG. 20 is a cross-sectional view of the dispenser of FIGS. 17 and 18 taken along line 20-20 of FIG. 18.

FIG. 30 is a side elevational view of the integral piston and rigid vial of the dispenser of FIG. 17.

FIG. 31 is a partial, cross-sectional view of the integral piston and rigid vial of FIG. 30.

FIG. 32 is a cross-sectional view of the flexible nozzle cover and bellows of the dispenser of FIG. 17.

FIG. 39D is a cross-sectional view of a portion of the integral piston and vial of FIG. 38.

FIGS. 47A-47D are views of another embodiment a storage and delivery system.

DETAILED DESCRIPTION OF PREFERRED EMBODIMENTS

Figure 1:
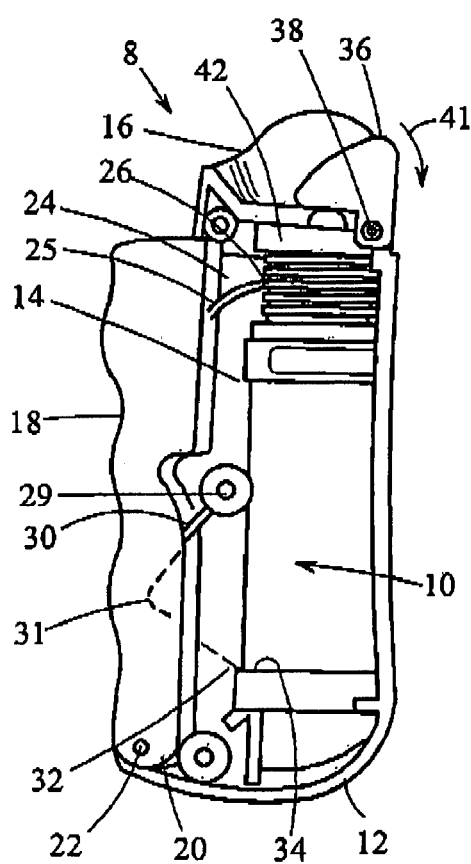
FIG. 1 is a partially broken-away, perspective view of an ocular treatment apparatus having a dispenser mounted therein in accordance with a preferred embodiment of the present invention.
Figure 1A:
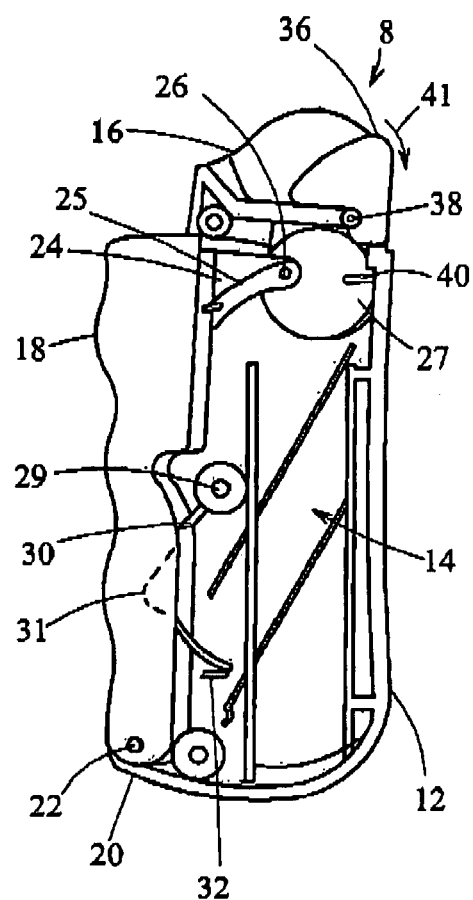
FIG. 1A is a view similar to FIG. 1 absent the dispenser.

In FIG. 1, there is shown an ocular treatment apparatus 8 that may be used in conjunction with a dispenser, shown generally at 10, in accordance with the present invention. As seen in FIGS. 1 and 1A, the treatment apparatus 8 comprises a housing 12 that may be generally U-shaped in cross section, and defines an interior cavity 14 and an eye cover 16. A trigger 18 is pivotably connected at one end 20 to the housing 12 via a hinge 22, and includes at the other end an arm portion 24 defining a slot 25. As shown best in FIG. 1A, a pin 26 of a wheel 27 is fixedly secured within the slot 25, and the wheel 27 is rotatably mounted on the interior wall of the housing 12. As best seen in FIG. 1, the trigger 18 is elongated and comprises finger grooves 28 for a comfortable fit with, e.g., a patient's hand. An approximately L-shaped spring arm 30 is fixedly secured at one end to a post 29 projecting inwardly from the interior wall of the housing 12, and the spring arm defines a knee or bent portion 31 (shown in phantom) engaging an interior surface of the trigger 18, and a free end 32 engageable with a rim 34 formed at one end of the dispenser 10. An eyelid depressor 36 is pivotably mounted by a hinge 38 to the end of the housing 12 adjacent to the eye cover 16, and includes a hook 40 fixedly secured to the wheel 27 for pivotably moving the eyelid depressor upon actuating the trigger 18.

In use, the eye cover 16 is placed adjacent to the tissue surrounding the eye with the eyelid depressor 36 engaging the tissue adjacent to the ocular cul-de-sac. Upon squeezing the trigger 18, the eyelid depressor 36 rotates in the direction of the arrow 41, and in turn moves the tissue adjacent to the eye to expose the ocular cul-de-sac. Rotation of the eyelid depressor 36 is caused by the wheel 27 which also uncovers a nozzle 42 formed at the adjacent end of the dispenser 10. Simultaneously, the spring arm 30 forces the rim 34 of the dispenser 10 away from the fixed nozzle 42 to thereby prime the pump of the dispenser, as described in further detail below. Upon squeezing the trigger 18 and correspondingly extending the dispenser 10 within the housing 12, the free end 32 of the spring arm 30 eventually disengages itself from the rim 34 of the dispenser to thereby release the extended dispenser from the spring arm. As a result, due to the resiliency or spring-like nature of the nozzle 42, as described further below, the extended dispenser contracts or moves back toward the nozzle and, in turn, releases a predetermined dosage of medicament (or other substance) from the nozzle and into the ocular cul-de-sac of the user's eye. Then, when the user removes the ocular treatment apparatus 8 from his or her eye and releases the trigger 18, the spring arm 30 automatically returns to its original or resting position as shown in FIG. 1 with the free end 32 engaging the rim 34. The force exerted by the spring arm 30 upon returning to its original position also rotatably drives the wheel 27 in the direction opposite that of the arrow 41 and, in turn, causes the eyelid depressor 36 to return to its original position, as shown. The ocular treatment apparatus is then ready to dispense another predetermined dosage of medicament or other liquid contained therein.

Other examples of ocular treatment apparatus that may employ the dispenser 10 are described in U.S. Pat. Nos. 4,981,479 and 6,033,384, which are assigned to the assignee of the present invention and are hereby incorporated by reference as part of the present disclosure. Accordingly, as may be recognized by those of ordinary skill in the pertinent art based on the teachings herein, the dispensers of the present invention may be utilized in any of numerous different apparatus or systems to facilitate holding and dispensing medicaments or other fluids, liquids or other substances contained therein, such as nasal inhalers.

Figure 2:
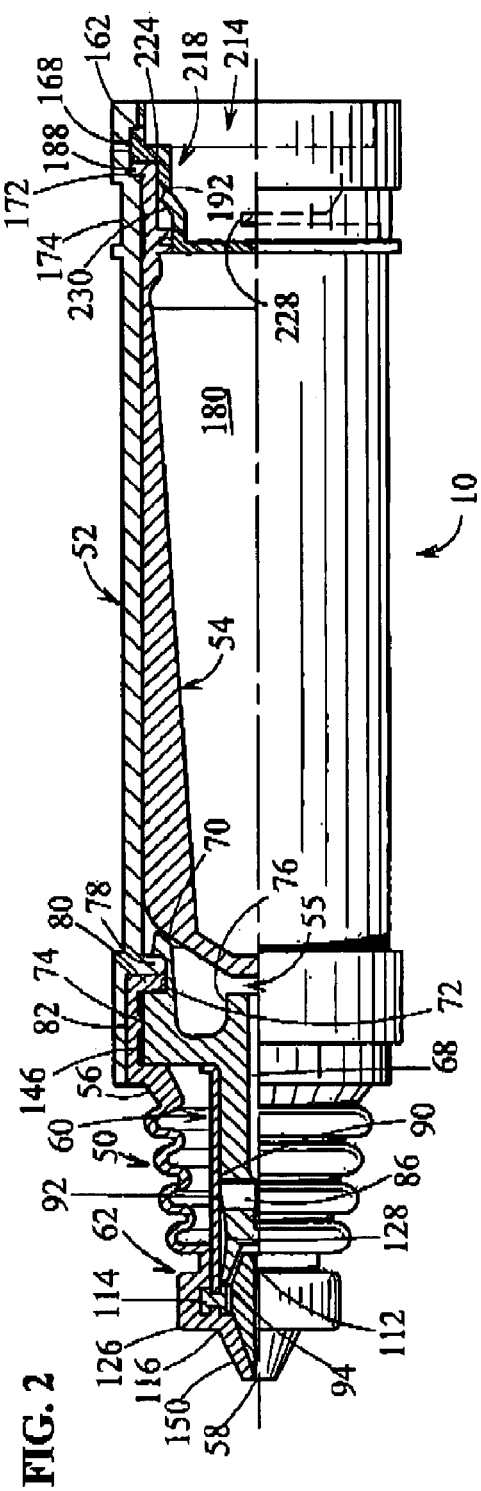
FIG. 2 is a side elevational view, partly in section, illustrating in further detail the dispenser of FIG. 1 including the pump assembly, vial and a bladder and wherein the pump assembly is disposed in a closed position.
Figure 3:
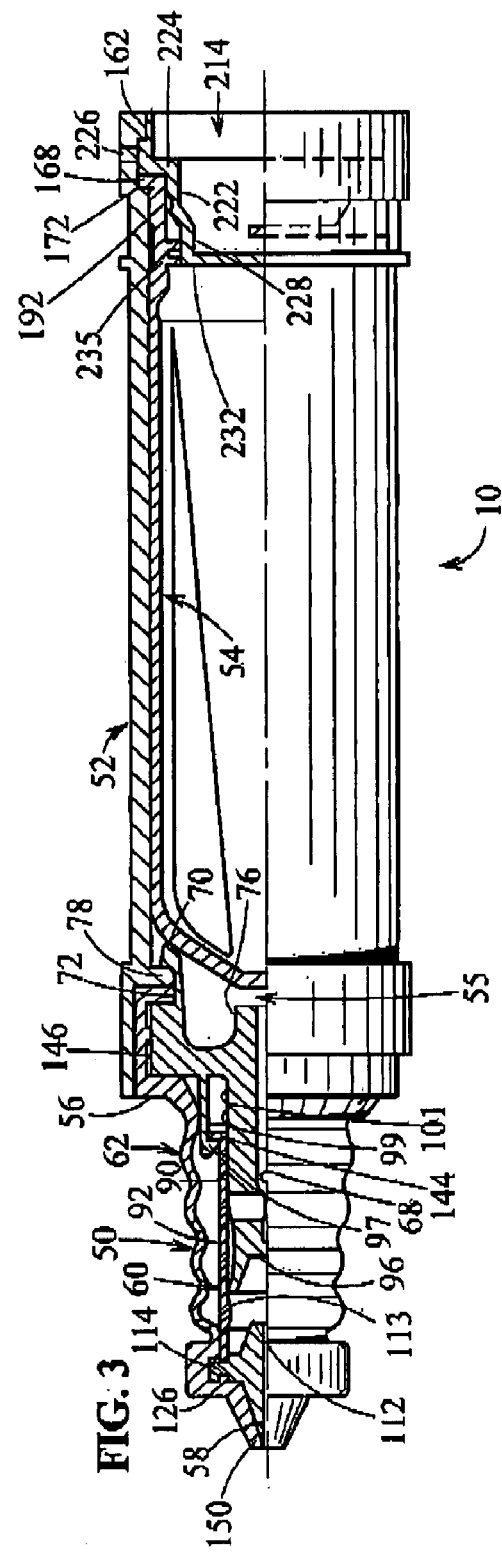
FIG. 3 is a view similar to that of FIG. 2, although the dispenser is rotated 90° with respect to its orientation in FIG. 2, and the pump assembly is disposed in an extended position.

Referring now to FIGS. 2 and 3, the dispenser 10 is shown partly in cross section to illustrate the internal components thereof. The dispenser 10 is generally cylindrical in outer configuration and comprises a pump assembly 50, a generally rigid vial 52, and a flexible bladder 54 disposed within a main fluid chamber 55 of the vial. The pump assembly 50 comprises a piston 56 for discharging predetermined doses of medicaments or other substances contained within the fluid chamber 55, a slide or body 60 for slidably receiving therein the piston and defining a predetermined dosage chamber therebetween, and a pump cover 62 forming with a nozzle 58 a one-way valve at the dispensing tip and a spring-like bellows for allowing either the piston or nozzle to be moved toward the other to eject a dose of medicament or other substance through the nozzle, and to force either the piston or the nozzle away from the other upon releasing the predetermined dose. The nozzle 58 hermetically seals the dispensing tip of the dispenser and ejects the pumped medicament or other substance therethrough.

Referring now also to FIG. 4, the piston 56 may be composed of any durable and moldable material, such as a plastic substance and, preferably, the material is suitable for use in connection with medicaments. A suitable material is a low density polyethylene. The piston 56 comprises a base portion 64, an elongated portion 66 extending from the base portion 64, and a central bore 68 which is in fluid communication with the main fluid chamber 55. The base portion 64 is generally disc-like in outer configuration, and comprises a connecting flange 70, an annular mounting portion 72, a first annular groove 74, and a second annular groove 76 spaced inwardly relative to the first annular groove and surrounding the inlet end of the central bore 68. The connecting flange 70 is configured to engage, e.g., in a snap-lock manner, the vial 52 defining a correspondingly dimensioned mounting flange 78 (FIG. 2). As shown in FIG. 2, the mounting portion 72 and first annular groove 74 receive an annular flange 80 and rib 82, respectively, of the pump cover 62 which is composed of a flexible material, as discussed in more detail below, and which thereby seals the main fluid chamber 55 of vial 52. As further shown in FIG. 2, when the piston 56 is assembled to the vial 52, the second annular groove 76 is located adjacent to the main fluid chamber 55. The second annular groove 76 thereby functions to provide a capture area to receive any gas bubbles improperly disposed within the main fluid chamber and to prevent the bubbles from passing into the central bore 68.

As shown best in FIG. 4, the elongated portion 66 comprises an annular groove 84, a laterally-extending bore 86, and a terminal end defining a receptacle portion 88. The annular groove 84 is configured to receive a seal 90 (FIG. 2), such as an o-ring, for sealing the piston in contact with the slide 60. The laterally extending bore 86 is in fluid communication with the central bore 68 and terminates adjacent to an annular interior surface 92 of the slide 60 (FIG. 3). As shown best in FIG. 4, the receptacle portion 88 comprises an annular wall 94, a tapered portion 95 extending between the annular wall 94 and bore 86, and a piston surface 96 for stopping movement of the nozzle 58 as described in more detail below in connection with FIGS. 5 and 6. The annular wall 94 defines a generally increasing outer diameter toward the distal end, and slidably engages the annular interior surface 92 of the slide 60 as described in more detail below in connection with FIG. 7.

As shown in FIG. 3, the piston 56 further includes two generally symmetrically-located hook portions 97, and each hook portion 97 defines in combination with an outer surface 101 of the piston 56 a respective slot 99. As described in more detail below in conjunction with FIG. 7, the slide 60 is reciprocally disposed within the slots 99 for allowing relative movement of the piston within the slide upon actuation of the pump.

Referring now to FIGS. 5 and 6, the nozzle 58 may be composed of any suitably durable, moldable, somewhat flexible material (in the configuration wherein the nozzle and body are made of one piece), such as a plastic material, and currently is composed of a material which has been found to be compatible with medicaments, such as those materials sold under the trademarks VELEX and LEXAN, both owned by the General Electric Company of Pittsfield, Mass. The nozzle 58 is preferably molded of one piece and comprises a truncated, conical-shaped body portion 98, and a disc portion 100 disposed coaxially with the conical-shaped portion and extending radially therefrom. It will be recognized that the conical-shaped portion 98 and disc portion 100 may be molded together or separately. The conical-shaped portion 98 comprises a tapered outer surface 102, a partial central bore 104, and an engagement portion 106. The partial central bore 104 terminates at a lever wall 108 which is dimensioned and configured to allow flexing of the tapered outer surface 102 in the direction of the arrow 110. The engagement portion 106 is configured to mate with the receptacle portion 88 of the piston 56, described above in connection with FIG. 4, and comprises a truncated conical configuration terminating in an engagement surface 112. As illustrated in FIGS. 2 and 3, when the piston 56 reaches the end of its stroke upon dispensing a predetermined dose, the engagement surface 112 of the nozzle is received within the guide wall 94 and engages the piston surface 96 to terminate further movement. It will be recognized that a variable stroke volume 113 is defined between the engagement surface 112 of the nozzle 58 and the piston surface 96 of the piston 56. As illustrated in FIG. 3, the maximum stroke volume is defined by the maximum extension of the engagement surface 112 from the piston surface 96.

As shown in FIG. 6, the disc portion 100 comprises an annular mounting portion 114 for affixably mounting the nozzle 58 to the pump cover 62 and slide 60 (FIGS. 2 and 3), and also comprises a slot 116 for the passage of fluid or other substances therethrough. The mounting portion 114 comprises an annular thickened portion 118 and a neck portion 120 disposed between a pair of annular grooves 122 and 124. As shown in FIGS. 2 and 3, the annular groove 122 is configured to engage a rib 126 of the pump cover 62 (FIG. 8), and the annular slot 124 is configured to engage a correspondingly configured terminal end portion 128 of the slide 60 (FIG. 7). As shown in FIG. 6, the annular groove 124 defines an annular crevice 130, employed, e.g., for easing assembly of the slide 60 to the nozzle 58. The slot 116 is disposed adjacent to a flattened portion 132 of the tapered outer surface 102, and provides fluid communication from the variable stroke volume 113 through the disc portion 100 to the tapered outer surface.

As illustrated in FIG. 7, the slide 60 defines a tubular body and may be composed of a similar substance to that described above with respect to the nozzle 58 (FIGS. 5 and 6). As described above and referring also to FIG. 2, the slide 60 comprises an annular inside surface 92 within which the piston 56 and engagement portion 106 of the nozzle 58 are disposed after assembly of the dispenser 10. The inside surface 92 defines a bore 134 with a neck portion 136 of reduced diameter disposed between a first transition zone 138 of relatively rapid increase in diameter, and a second transition zone 140 of relatively gradual increase in diameter. Referring now to FIG. 2, it will be understood that during relative movement of the nozzle 58 and the slide 60 away from the piston 56, the annular wall 94 of the piston (FIG. 4) will engage the second transition zone 140 (FIG. 7) in sealing engagement to thereby force fluid contained within the variable stroke volume 113 into the slot 116 of the nozzle tip.

With reference to FIG. 7 and as described above in connection with FIGS. 5 and 6, the slide 60 defines a terminal end 128 that includes an annular ridge 142 configured to engage the crevice 130 of the nozzle 58. As shown in FIG. 3, the opposite end of the slide 60 defines a flange 144 that is configured to engage the hook portion 97 of the piston 56.

FIG. 8 depicts a cross-sectional view of the flexible pump cover 62. The flexible pump cover 62 may be composed of any durable, resilient and flexible material, such as an elastomeric material. Preferably, the pump cover 62 is composed of a thermo-elastic material, such as a styrene-butadiene elastomer sold under the trademark KRATON by GLS of Illinois. Other suitable materials include polyvinylchloride, Santoprene™ and butyl rubber. The pump cover 62 comprises a mounting portion 146, a bellows portion 148, and a nozzle cover 150 which cooperates with the slot 116 (FIG. 6) to provide an elastic valve, as described further below in connection with FIG. 5. As described above in connection with FIG. 4, the mounting portion 146 comprises an annular flange 80 that fits within the mounting groove 72 adjacent to the mounting flange 78 of the vial 52 (FIG. 2). As shown in FIG. 8, the rib 82 defines in cross section a truncated conical shape corresponding to the configuration of the annular groove 74 of the piston (FIG. 4). Because of the resilient nature of the material of the pump cover 62, the annular flange 80 may be slightly oversized in order to provide a resilient fit with the vial 52 and piston 56 and thereby, in combination with the rib 82, hermetically seal the main fluid chamber 55 (FIG. 2).

The bellows portion 148 extends between the mounting portion 140 and nozzle cover 150, and comprises a plurality serpentine or inversely curled portions 152 which function to provide resiliency in a direction generally parallel to a central axis 154 and sufficient spring-like force to either drive the piston or the nozzle away from the other and return the piston to the top of its stroke upon dispensing a predetermined dose of a medicament or other substance contained within the chamber 55. Referring also to FIGS. 2 and 6, the nozzle cover 150, when mounted, is dimensioned and configured to resiliently engage the nozzle 58 and slide 60, and includes the annular rib 126 extending axially from a disc engagement portion 156. The disc engagement portion 156 is disposed between a slide engagement portion 158 and a nozzle body engagement portion 160. Referring also to FIG. 6, the nozzle body engagement portion 160 is configured to engage the tapered outer surface 102 of the nozzle 58 to thereby form a normally-closed, one-way valve therebetween. As can be seen in FIG. 8, the cross-sectional thickness of the nozzle engagement portion 160 gradually decreases in the axial direction from the disc engagement portion 156 toward the dispensing tip 161. The gradually-decreasing cross-sectional thickness of the nozzle engagement portion 160 facilitates the release of the medicament or other substance through the one-way valve formed by the elongated, annular interface between the relatively flexible nozzle engagement portion 160 of the cover and the tapered surface 102 of the nozzle body, while simultaneously preventing air or other gases from passing through the valve in the opposite direction, in accordance with the teachings of the below-mentioned patents incorporated by reference herein.

As shown in FIG. 6, the conical portion 98 defines a tapered outer surface or valve seat 102. The interference fit between the nozzle cover 150 and the valve seat 102 forms a normally-closed valve to hermetically seal the openings or slot 116 until a dose of the substance contained in the dispenser is delivered. As shown, the portion of the nozzle cover 150 that interfaces with the valve seat 102 is preferably tapered such that the thickness is greater near the base of the valve seat and gradually reduces to a lesser thickness near the end of the valve seat to facilitate opening of the valve and the flow of substance therethrough. In addition, the axial length of each of the valve seat 102, nozzle cover 150 and annular valve opening formed therebetween is sufficiently long to always maintain an annular segment of the valve cover in contact with the valve seat when dispensing substance through valve opening. As can be seen, the nozzle cover 150 defines an aperture therethrough, the valve seat 102 is received within the aperture to form the normally-closed annular valve opening at the interface between the valve seat and valve cover, and the diameter (or width) of the valve seat is greater than the diameter (or width) of the aperture in the cover to thereby form an interference fit and normally-closed valve opening therebetween. Preferably, the degree of interference between the valve cover aperture and valve seat decreases in the axial direction of the valve seat from the interior toward the exterior of the dispenser to facilitate the flow of substance therethrough.

As may be recognized by those of ordinary skill in the pertinent art based on the teachings herein, the one-way valve of the dispensers of the present invention may take any of numerous different configurations that are currently or later become known for performing the function of the valve described herein, including any of the one-way valve configurations disclosed in co-pending patent application Ser. No. 60/403,484, filed Aug. 13, 2002, Ser. No. 10/272,577, filed Oct. 16, 2002, and Ser. No. 10/640,500, filed Aug. 13, 2003, each of which is hereby expressly incorporated by reference as part of the present disclosure.

In operation, as described above in connection with FIGS. 1 and 1A, movement of the vial 52 in the axial direction causes the piston 56 to move from the position shown in FIG. 2 into the position shown in FIG. 3 (or vice versa), e.g., by actuating the trigger 28 of FIG. 1 or other actuator, which draws fluid into the variable volume fluid chamber 113 from the main fluid chamber 55 via the central bore 68 and laterally-extending bore 86 of the piston. Referring now also to FIGS. 6 and 8, as the piston 56 moves toward the nozzle 58 (or vice versa), the fluid is injected through the slot 116 (FIG. 6), along the flattened surface 132, between the tapered surface 102 and nozzle body engagement portion 160, and then outwardly of the nozzle tip. Further details of pump assemblies that may be used in the practice of the present invention are described in U.S. Pat. Nos. 5,944,702, 5,875,931 and 5,746,728, which are assigned to the same assignee as the present invention, and are hereby expressly incorporated by reference as part of the present disclosure.

One advantage of the pump configuration of the illustrated embodiment, and as indicated by the arrow indicating the path of fluid flow in FIG. 6, the pumped fluid follows a fairly straight path extending in a direction parallel to the axis 154 from the variable stroke volume 113, over the tapered surfaces of the engagement portion 106, through the slot 116, and between the one-way valve formed by the interface of the nozzle engagement portion 160 of the cover and the tapered outer surfaces 132 and 102 of the nozzle body. This relatively straight and smooth fluid flow path allows the pumped fluid to flow through the nozzle with relatively little head loss, thus allowing lesser force to dispense the fluid and otherwise facilitating precise control over the type of fluid flow to be emitted at the dispensing tip, such as control over drop size, flow velocity, and/or spray droplet size, spray pattern, etc.

Yet another advantage of the illustrated pump configuration is that the bellows 148 is sealed relative to the variable-stroke volume 113 to thereby prevent any of the medicament or other substance contained within the chamber 55 from collecting in the space between the bellows and the piston or slide. As can be seen, the o-ring or like seal 90 forms a fluid-tight seal between the piston and the slide, thus preventing any fluid from flowing therethrough and into the bellows. Similarly, fluid-tight seals are formed at the interfaces of the cover 62, nozzle 58 and slide 60, including fluid-tight seals at the interfaces of the slide engagement portion 158 of the cover and the slide 60, and at the interface of the annular rib 126 of the cover and at the annular groove 122 of the nozzle 58.

Referring now to FIGS. 9 and 9A, the vial 52 is preferably composed of a suitably rigid and moldable material, such as a rigid polymeric material, e.g., polycarbonate or polyvinylchloride. Preferably, this material is selected to be compatible with a wide variety of medicaments, such as that sold under the trademark Lexan of the General Electric Corporation of Pittsfield, Mass. The vial 52 is tubular in configuration and comprises an outer wall 77 that defines the main fluid chamber 55, the annular mounting flange 78 discussed above in connection with FIGS. 2 and 4, and an annular connecting portion 162 formed on an opposite end of the vial relative to the mounting flange 78. The main fluid chamber 55 is dimensioned such that it is large enough to contain a predetermined quantity of a fluid to be dispensed, such as a medicament, along with the flexible bladder 54 (FIG. 2) discussed in more detail below. The mounting flange 78 includes an annular ridge 164 for mounting the vial 52 into sealing engagement with the nozzle cover 62 (FIG. 2) and preventing movement of the cover during use of the dispenser 10. As seen in FIGS. 2 and 3, the mounting portion 146 of the cover 62 is sandwiched between the base 64 of the piston 56 and the rigid vial 52 to form a fluid-tight seal.

As shown in FIG. 9A, the annular connecting portion 162 comprises a tapered end 166 and a peripheral groove 168 spaced inwardly therefrom on an increased diameter portion 170. An annular ridge 172 is provided for engaging the flexible bladder 54 (FIG. 2). As described further below, the increased diameter portion 170 and annular ridge 172 function to allow hermetic sealing of the main fluid chamber 55 after assembly of the vial 52. As also described further below, an annular groove 174 is provided for retention of the vial 52 during filling of the main fluid chamber 55.

Figure 10:
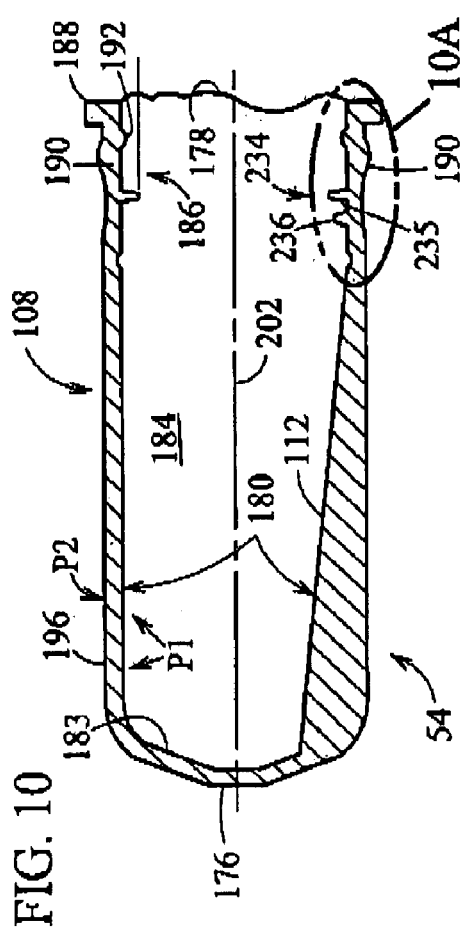
FIG. 10 is a central, cross-sectional view taken along a longitudinal axis of the bladder of the dispenser of FIGS. 2 and 3 showing in this configuration a three-ribbed structure provided to allow the bladder to collapse into a predetermined collapsed condition.

Referring now to FIG. 10, the flexible bladder 54 may be composed of any suitably flexible material, and preferably defines barrier properties to prevent the passage therethrough of vapor, moisture and gas. For ease of manufacture, the material preferably may be molded and is compatible with a wide variety of medicaments or other substances to be contained within the chamber 55, and therefore in a preferred embodiment may be formed of a rubber or synthetic rubber. Alternatively, the flexible bladder 54 may be composed of a thermo-elastic material, such as the styrene-butadiene elastomer sold under the trademark KRATON as discussed above in connection with the pump cover 62. Similarly, materials sold under the trademarks VISKAFLEX owned by the AES Company, ALCRYN or HYTREL owned by the Dupont Company of Wilmington, Del., and SARLINK owned by the DSM Company may be used instead. These materials are only exemplary, however. As may be recognized by those skilled in the pertinent art based on the teachings herein, the flexible bladder may be made of any of numerous other materials that are currently or later become known for performing the function of the flexible bladder as disclosed herein.

In the preferred embodiments of the present invention, the flexible bladder 54 is made of a resilient material as described above and is molded in the expanded condition. Accordingly, when collapsed in the manner described further below, the resilient bladder tends to force itself outwardly and, in turn, increase the pressure of the medicament or other fluid in the main fluid chamber 55 in comparison to the pressure in the interior of the bladder. A significant advantage of this pressure differential is that it facilitates in preventing the ingress of air, other gases or vapors located within the interior chamber of the bladder through the bladder or otherwise into the main fluid chamber. As a result, the dispensers of the present invention are particularly well suited for containing multiple dose, non-preserved medicaments or other substances, and in maintaining such substances in a sterile, airless condition, throughout substantial periods of storage, shelf life and/or use of the dispensers. This advantageous feature also facilitates in preventing any changes in the ambient conditions of the dispenser from affecting the airless condition of the main fluid chamber 55, and otherwise prevents the ingress of air, other gases or vapors into the main fluid chamber.

Figure 10B:
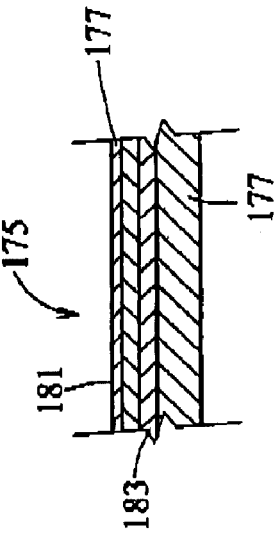
FIG. 10B is a highly enlarged view of a portion of the bladder of FIG. 10.

The flexible bladder 54 preferably also provides a barrier to the passage of gas, such as air, through the flexible bladder, and thus may be composed of a single layer of material that has a substantially reduced permeability to air. In one embodiment of the present invention, the bladder 54 is composed of a multi-layered material. For example, as illustrated in FIG. 10B, a bladder wall 175 may comprise a first flexible layer 177 of an elastomer that is relatively porous to air, and a barrier layer 179, such as a metallized MYLAR, e.g., an aluminum and polyester composition, sold by the Dupont Corporation of Wilmington, Del., that is relatively impervious to air. The barrier layer 179 may be disposed between a polyethylene upper layer 181 and lower layer 183 to facilitate adhesion of the barrier layer to the bladder wall 175 while maintaining flexibility. Alternatively, the barrier layer 179 may be composed of polyvinylidene chloride sold under the mark SARAN owned by the Dow Chemical Company of Midland, Mich. It will be appreciated that the barrier layer 179 is preferably dimensioned to cover as much of the bladder wall 175 as permitted in order to reduce the passage of air therethrough without interfering with the various functions of the flexible bladder as more fully described below. The barrier layer 179 is also preferably disposed on the interior of the bladder wall 175. Optionally, the barrier material may be a butyl rubber-based material, such as that used for the manufacture of syringe stoppers, or used in the tire industry. As may be recognized by those skilled in the pertinent art based on the teachings herein, the flexible bladder and barrier materials disclosed herein are only exemplary, and any of numerous other materials that are currently known, or later become known for performing the functions disclosed herein, may be equally employed.

Referring now again to FIG. 10, the flexible bladder 54 is tubular in configuration and comprises a closed end 176 and an open end 178 that fluidly communicates with a cavity 180. The bladder 54 defines an external diameter dimensioned to fit within the vial 52 (FIG. 2) when in the expanded condition as shown in FIG. 10. As shown in FIGS. 2 and 3, the outer surface of the bladder 54 preferably defines a shape or morphology substantially the same as that of the interior surface of the rigid vial 52 so that upon expanding the flexible bladder, the flexible bladder conforms to and contacts the rigid vial throughout the interface of these two components to thereby eliminate any ullage or dead space between the components, and force all of the medicament or other substance within the chamber 55 into the variable stroke volume 113 of the pump 50 for dispensing therefrom. In addition, the outer diameter (or width) of the flexible bladder when fully expanded is preferably slightly greater than the inner diameter (or corresponding width) of the rigid vial, so that the expanded bladder may exert a resilient force against the vial to maintain at least a slight pressure differential between the chamber 55 on one side of the bladder and the interior of the bladder and thereby prevent the ingress of air, other gases or vapors through the bladder and into the main fluid chamber, as described above.

Figure 11:
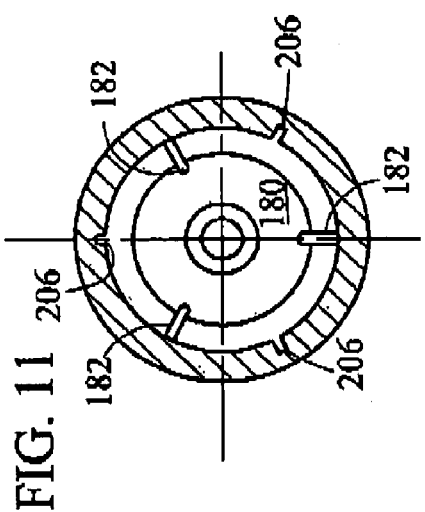
FIG. 11 is a cross-sectional view taken along a transverse axis of the bladder of FIG. 10.

As shown in FIGS. 10 and 11, longitudinally extending stiffeners or rib portions 182 are disposed along the inside surface 184 and function to provide a supporting structure about which the bladder 54 may collapse as will be described in more detail below in conjunction with FIG. 12. To achieve this, the rib portions 182 extend axially along the interior surface 184 and are approximately equally spaced about the circumference of the interior surface. It will be recognized that other configurations of the rib portions 182 and/or locations at which the rib portions may be employed are contemplated by the present invention. For example, the rib portions 182 also may extend along the inside surface 183 of the closed end 176 of the flexible bladder 54.

Figure 10A:
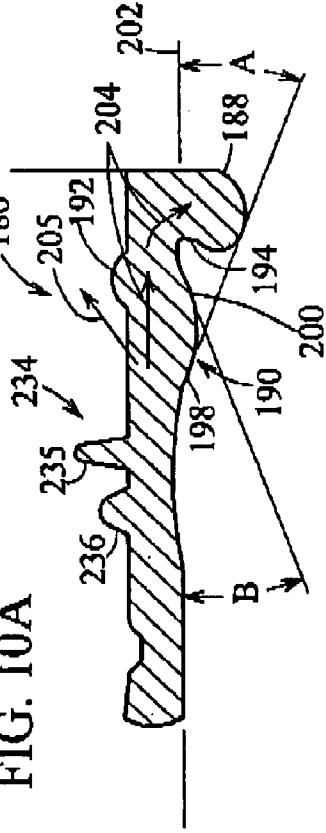
FIG. 10A is an enlarged view of a portion of the bladder of FIG. 10.

As illustrated in FIGS. 10 and 10A, the flexible bladder 54 includes a mounting portion 186 that comprises an annular flange 188 formed at the rear end of the bladder, an outer annular lobe 190 spaced axially inwardly relative to the flange 188, and an inner annular lobe 192 spaced between the outer annular lobe 190 and the flange 188. As shown in FIG. 10A, the annular flange 188 defines on its underside an annular, V-shaped indent 194 for sealing engagement with the annular ridge 172 of the vial 52 (FIG. 9A). In addition, the annular flange 188 is over-sized so that during initial assembly with the vial 52, as will be discussed in more detail below, the peripheral surface of the annular flange may engage the corresponding annular groove 168 of the vial 52 (FIG. 9A).

During storage and/or shelf life of the dispenser 10, the material of the flexible bladder 54 may flow or move in order to equalize the tensile and compressive forces that it is subject to. Creep, as used herein, refers to a change in property of the material wherein there is a loss in resilience and memory of the material. In particular, after undergoing creep the elastic material may permanently deform and lose at least some of its original elasticity. Accordingly, after assembly and during filling of the dispenser 10, the cavity 180 of the flexible bladder 54 may be subject to low pressure which causes collapse and elastic deformation thereof which is maintained by the pressure of fluid filled in the main fluid chamber 55 (FIG. 2). Thereafter, the filled dispenser may be maintained in storage and/or on a store or other shelf for at least two or more months prior to use, during which the material of the bladder may undergo creep causing at least some deformation thereof. To properly manage the movement of the material during creep of the flexible bladder 54, and as shown best in FIG. 10A, the bladder is provided with the outer annular sealing lobe 190 and the inner annular sealing lobe 192 spaced axially between the outer sealing lobe and the flange 188 so that, when creep resulting from compression of the elastomeric or rubber-like material occurs, the intra material pressure is balanced in between the two lobes 190,192 and a persistent, fluid-tight seal is provided. This mechanical seal can then be maintained due at least in part to the material reservoir formed by the inner lobe 192 in which creeping material in the outer lobe 190 offsets that of the inner lobe.

Figure 14:
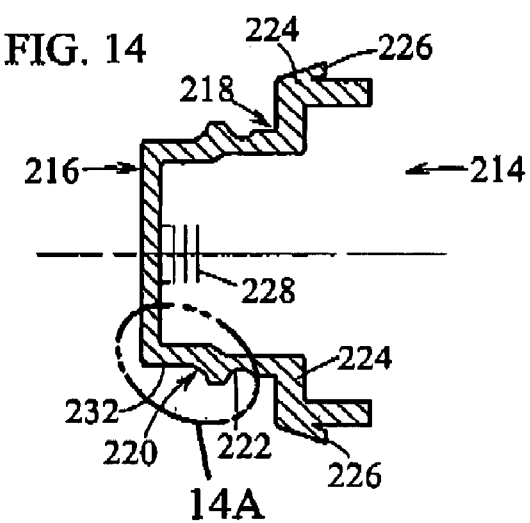
FIG. 14 is a sectional view of the rear plug taken along line 14-14 of FIG. 13.

As shown in FIG. 10A, the outer annular lobe 190 comprises a first angular portion 198 located on one side of the lobe 192, and a second angular portion 200 disposed on the opposite side of the lobe. The first angular portion 198 defines a first acute angle "A" with respect to a center axis 202 that may be within the range of approximately 0° to approximately 30°, and more preferably within the range of approximately 0° to approximately 10°. The second angular portion 200 defines a second acute angle "B" relative to the axis 202 that may be within the range of approximately 0° to approximately 15°, and more preferably within the range of approximately 0° to approximately 5°. In order to ensure that during creeping of the material of the flexible bladder 54 the material moves approximately in the directions of the arrow 204 and arrow 205, the first angle A is larger than the second angle B and the flexible bladder is axially fixed by the inner annular sealing lobe 192 received within the corresponding annular groove 22 of the rear plug (FIG. 14). As shown in FIGS. 2 and 3, when the flexible bladder 54 is fully received within the rigid vial 52, the outer annular lobe 190 is pressed against the smooth interior wall of the vial, the inner annular lobe 192 is received within the corresponding annular groove 22 of the rear plug (FIG. 14), and the annular flange 188 is sandwiched between the rear plug and the annular ridge 172 of the rigid vial. Thus, the inner annular sealing lobe 192 functions as a material reservoir for the outer annular sealing lobe 190, and as indicated by the arrows 204 and 205, the axially-offset lobes cause the material to flow generally from the outer lobe 190 toward the inner lobe 192, and from both lobes generally toward the annular flange 188. As a result, the material flow is persistently directed toward the inner sealing lobe 192 and/or annular flange 188 to thereby maintain a fluid-tight seal between the flexible bladder, rigid vial and rear plug, regardless of the degree of creep of the bladder material. As can be seen, the shape and relative position of the outer annular lobe 190 as described above facilitates in directing the forces within the bladder and thus the material in the directions of the arrows 204 and 205 to thereby maintain the fluid-tight seal throughout the storage, shelf-life and usage of the dispenser 10.

As shown in FIG. 11, the flexible bladder 54 preferably also comprises at least one surface discontinuity 206 that facilitates and controls the collapse of the bladder from a tubular configuration to a predetermined collapsed configuration to thereby substantially eliminate the volume of the cavity 180 defined by the interior of the bladder. In the illustrated embodiment, the flexible bladder comprises three surface discontinuities 206 located on the interior surface 184 of the bladder and approximately equally spaced relative to each other. As can be seen, the discontinuities 206 are each approximately equally spaced between adjacent elongated ribs 182. The discontinuities 206 are illustrated in the configuration of a crevice or crack terminating in a generally flat center portion (not numbered) in cross section as shown. As can be seen, the surface discontinuities 206 cause the bladder to collapse or fold onto itself about each elongated rib 182 to thereby form in the collapsed condition three folded sections or legs spaced about 120° relative to each other. As may be recognized by those skilled in the pertinent art based on the teachings herein, and illustrated by the additional embodiments below, any of numerous other structures or configurations may be equally employed to collapse the bladder into a predetermined shape, such as the predetermined collapsed shape formed by discontinuities and elongated ribs described above.

Figure 12:
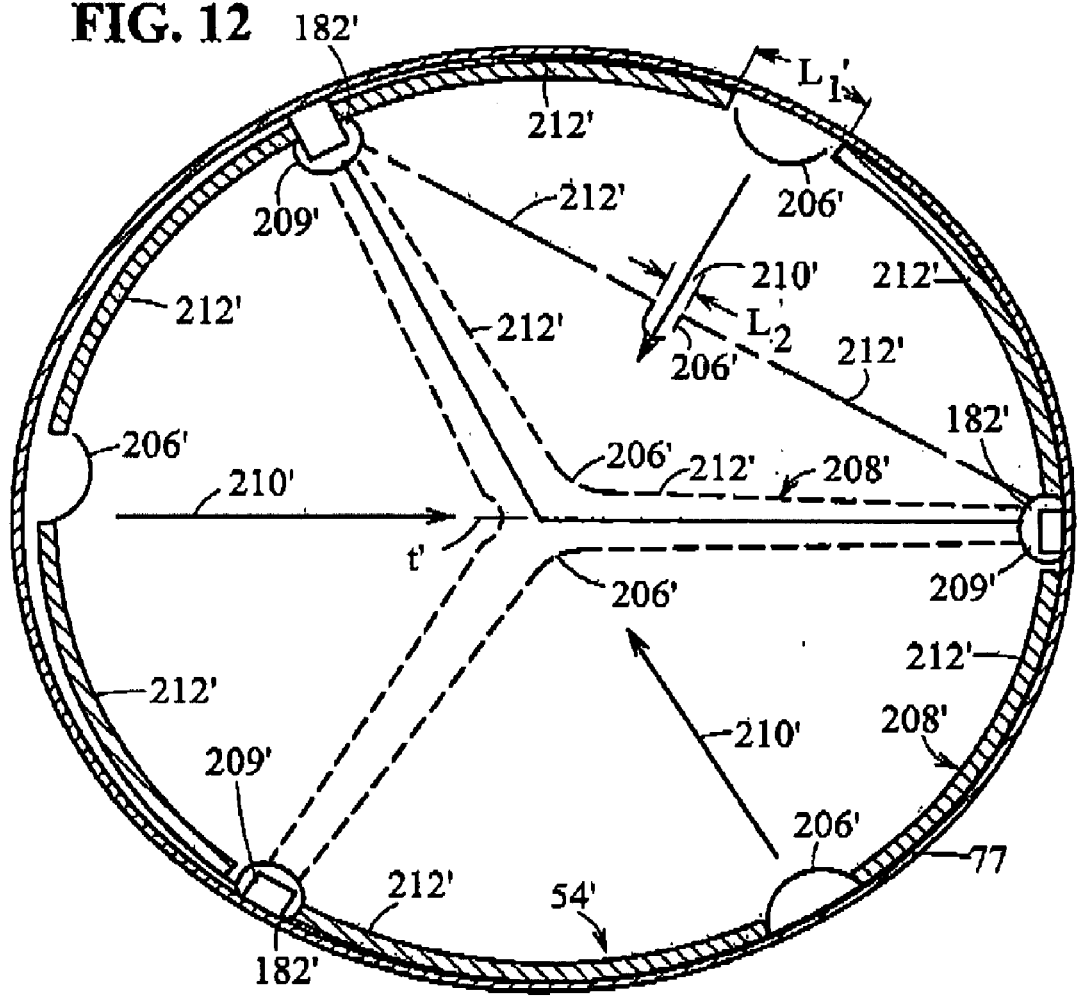
FIG. 12 is a schematical view showing, in cross section, another embodiment of the bladder of the dispenser of FIGS. 2 and 3 disposed within the rigid vial and including elongated discontinuities or elongation buffers disposed in an outer wall of the bladder to facilitate the collapse of the arcs that pass through the chords of the respective arcs.

Referring now to FIG. 12, a cross section of an outer wall 208' of a flexible bladder 54' is illustrated in schematic. The flexible bladder 54' is capable of collapsing in the direction of arrows 210' from an expanded position, shown in solid lines adjacent to the outer wall 77 of the vial 52 (FIG. 9) to a collapsed position shown in broken lines. The flexible bladder 54' is functionally similar to the flexible bladder 54 and thus like elements are labeled with like reference numerals followed by the prime (') symbol. However, it will be recognized that some differences in structure exist between the flexible bladder 54 and the flexible bladder 54'. For example, discontinuities 206' are illustrated as being inverted with respect to the discontinuities 206 and generally cover the entire cross-sectional thickness (t') of the wall 208'. While the discontinuities 206' are illustrated as generally arcuate in configuration, it will be appreciated that other configurations, such as that of discontinuities 206, which also perform the function described below may be employed instead. Also, it will be appreciated that the rib portions 182' define mounting slots 209' for receiving therein correspondingly-shaped portions (not shown) of the vial 52.

It will be understood that both the discontinuities 206 and 206' function to allow for a reduction in length of the portions of the wall 208' necessary to collapse the flexible bladders 54 and 54'. While this function is being described in connection with the embodiment of FIG. 12, this description is equally applicable to the embodiment of FIG. 11. As shown in FIG. 12, the wall 208' comprises a plurality of wall portions 212' extending between each discontinuity 206' and adjacent rib portion 182', and as shown in solid lines each wall portion 212' forms an arc when the bladder 54' is expanded. It will be recognized that during collapsing of the bladder 54' in the directions of the arrows 210', the wall portions 212' become approximately linear and form a chord as shown in the dashed and dotted lines, and then inversely arcuate as illustrated in the dashed lines. Accordingly, as illustrated, a length $L_1$ of the discontinuities 206' shown in solid lines shortens to a length $L_2$ shown in dotted and dashed lines to thereby allow free movement of the arcs 212' in the direction of the arrows 210'. Once the flexible bladder 54' has collapsed, the bladder may expand and the wall portions 212' may freely move in a direction opposite that of the arrows 210'.

Figure 13:
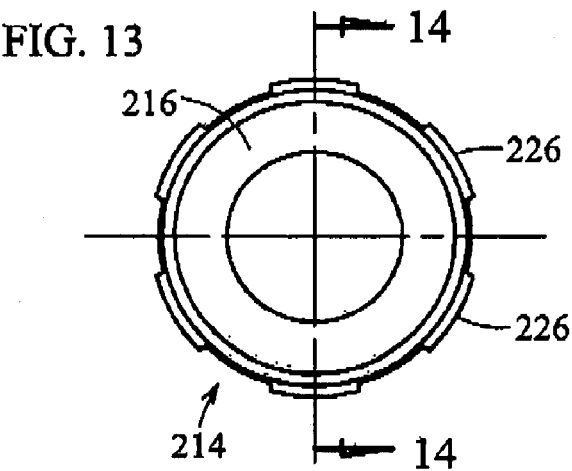
FIG. 13 is a top plan view of the rear plug employed to close the rear end of the inner bladder by forming a sandwich-type structure between the rigid vial and rear plug to hermetically seal the dispenser of FIGS. 2 and 3.
Figure 14A:
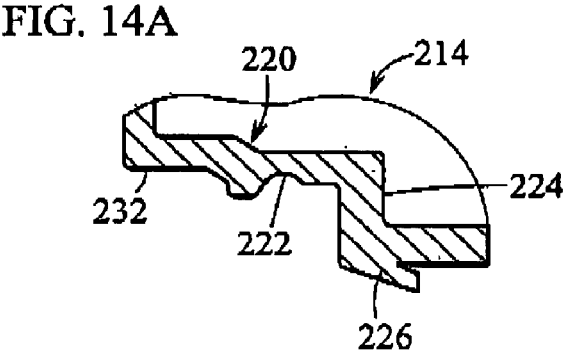
FIG. 14A is an enlarged portion of the rear plug of FIG. 14 showing further detail of an annular side wall of the plug.
Figure 17:
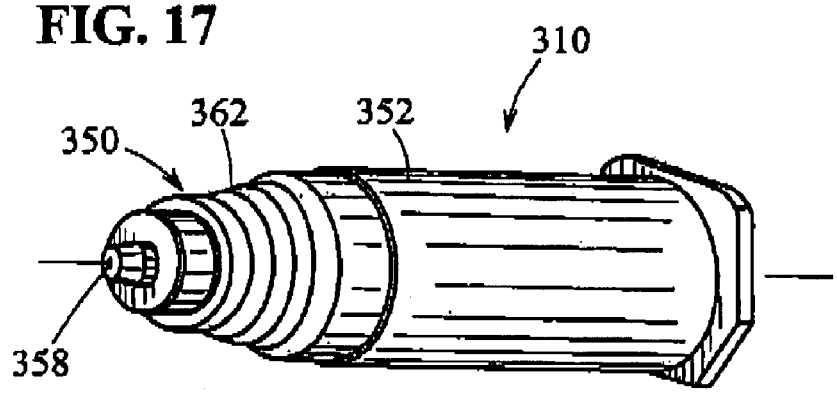
FIG. 17 is a perspective view of another embodiment of a dispenser of the present invention.
Figure 18:
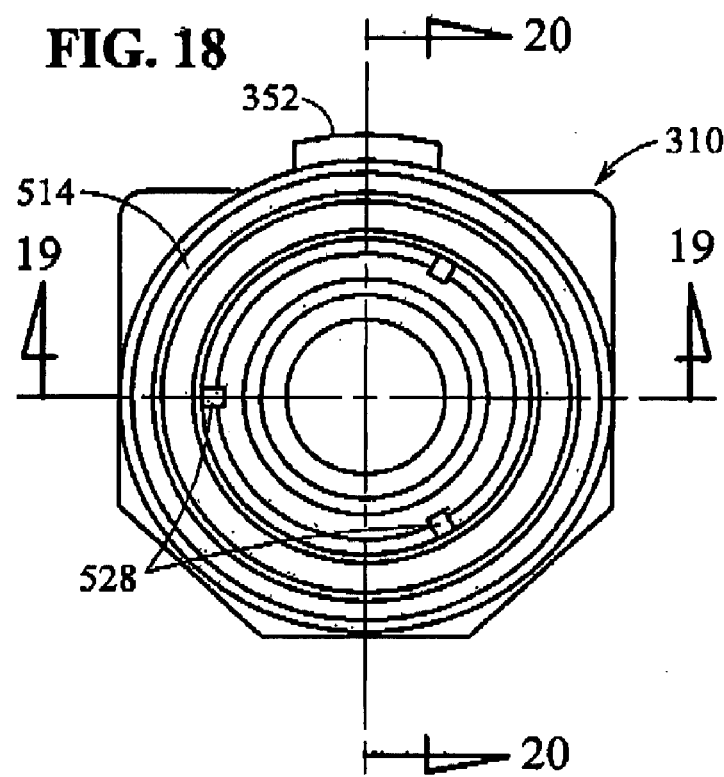
FIG. 18 is an end elevational view of the dispenser of FIG. 17.

As illustrated in FIGS. 13 and 14, the flexible bladder comprises a rear plug 214 configured to mate with the open end 178 of the flexible bladder 54 (FIG. 2) and to seal the flexible bladder 54 disposed between the rear plug and the rigid vial 52. The rear plug 214 may be composed of any suitably strong, moldable and durable material, such as a polymeric material, e.g., polyethylene, and is preferably composed of Lexan™ or a like polycarbonate for its stress-resistant properties. The rear plug 214 comprises an end wall 216 and a side wall 218 that, as seen best in FIG. 14A, preferably includes a tapered portion 220 defining a gradually increasing diameter in the direction of the rear end of the plug, an annular groove 222 spaced rearwardly of the tapered portion 220, a stepped portion 224, a plurality of outwardly-protruding protective tabs 226 (or bumps for ease of manufacturing) angularly spaced relative to each other about the axis of the plug, and an aperture 228 extending through the side wall for allowing fluid communication between the interior chamber 180 of the bladder and the ambient atmosphere. The tapered portion 220, because of the increasing diameter thereof, provides for ease of assembly of the plug 214 to the flexible bladder 54 (FIG. 2) and defines an annular space 230 (FIG. 2) located between the plug and the adjacent surface of the flexible bladder. As described above and shown in FIGS. 2 and 3, the annular groove 222 is configured to receive the inner annular lobe 192 (FIG. 10) and the stepped portion 224 sandwiches the annular flange 188 of the flexible bladder 54 against the annular ridge 172 of the rigid vial. As best seen in FIGS. 13 and 14, the safety sealing tabs 226 project upwardly and outwardly from the stepped portion 224 and are angularly spaced relative to each other about the axis of the plug. The sealing tabs 226 are provided for locking the plug 214 to the vial 52 (FIG. 2) and are configured to snap-fit within the annular groove 168 of the vial (FIG. 9) upon being pressed against the annular flange 188 of the bladder to thereby maintain an airtight seal. In addition, because the sealing tabs 226 are tapered outwardly as shown typically in FIG. 14A, the tabs easily snap into the annular groove 168 of the vial; however, the tabs cannot be moved out of the groove in the opposite direction and thereby form a tamper-proof seal. The aperture 228 provides for fluid communication between the annular space 230, chamber 180 (FIG. 2) and ambient atmosphere, and is illustrated as being generally rectangular in configuration. However, it will be understood that other configurations, such as circular or other shapes, may be employed, providing that a sufficient volume of air may pass therethrough to fill the interior chamber 180 of the flexible bladder 54.

Returning to FIGS. 10 and 10A, the flexible bladder 54 also preferably comprises a two-way valve 234 axially spaced below the sealing lobes 190 and 192 for controlling the flow of air between the interior chamber 180 of the bladder and ambient atmosphere. The valve 234 comprises an annular operator 235 projecting inwardly from the interior wall of the bladder and having a generally ridge-like configuration in cross section. As shown in FIGS. 2 and 3, the end portion of the annular operator 235 engages the annular surface 232 formed at the base of the rear plug 214, and is disposed between the annular space 230 and the interior chamber 180 of the bladder. The flexible bladder 54 further defines a plurality of support protuberances 236 that are axially spaced adjacent to the annular operator 235 and angularly spaced relative to each other about the axis 202. The end surface of each protuberance 236 is spaced inwardly relative to the end of the annular operator 235 to thereby allow the operator 235 to engage and seal the interface between the operator and rear plug, while simultaneously ensuring sufficient radial spacing between the rear plug and flexible bladder for allowing movement of the operator 235 in either direction. Thus, as can be seen, the operator 235 and annular wall 232 of the rear plug form a two-way valve allowing fluid to flow therethrough when the differential pressure across the valve is sufficient to axially flex the operator. It will be understood that the rigidity of the operator is set to allow fluid to pass therethrough when the pressure differential exceeds a predetermined threshold pressure. Thus, a significant advantage of the valve 234 is that it maintains a relatively stable micro-atmosphere within the inner chamber 180 of the flexible bladder 54 and prevents a regular exchange of air, other gases or vapors between the micro-atmosphere within the bladder and the ambient atmosphere. For example, the valve 234 allows air to be drawn into the chamber 180 upon dispensing the medicament or other substance from the main fluid chamber 55 to thereby allow the bladder to expand and fill the space of the dispensed medicament. However, the valve 234 otherwise prevents air or vapors from flowing freely between the micro-atmosphere and the ambient atmosphere. Thus, the micro-atmosphere within the chamber 180 may define different pressure and/or humidity levels in comparison to the ambient atmosphere. A significant advantage of this feature is that it insulates the micro-atmosphere from fluctuations in the pressure and/or humidity levels of the ambient atmosphere, thereby maintaining relatively stable pressure and humidity levels within the micro-atmosphere and thus preventing the ingress of air or vapors through the bladder wall and into the main fluid chamber.

In FIGS. 15A-15C, the dispenser 10 is illustrated in the full, half-full and empty conditions, respectively. In FIG. 15A, the main fluid chamber 55 is filled with, e.g., a medicament (not shown) that the pump assembly 50 may pump outwardly of the nozzle 58. Accordingly, the bladder 54 is illustrated in a collapsed state. In FIG. 15B, the flexible bladder 54 is shown in an expanded condition whereby the bladder has expanded to displace the volume of medicament dispensed from the main fluid chamber 55. To achieve this result, air has passed in the direction of arrow 240, through the valve 234 and into the interior chamber 180 of the flexible bladder. In FIG. 15C, the dispenser 10 is illustrated in an empty condition. As can be seen, the bladder 54 is fully expanded against wall 77 of the rigid vial and substantially conforms to the morphology of the rigid vial to thereby eliminate any ullage or dead space and force all medicament or other substances therein into the pump 50.

Referring now to FIGS. 16A-16C, initial assembly of the dispenser 10 for purposes of sterilization, e.g., by irradiation of energy rays, is illustrated in FIG. 16A. In particular, the rear plug 214 is fitted to the flexible bladder 54, and the plug and flexible bladder are partially inserted into the vial 52. Turning now also to FIGS. 9A and 10, the flange 188 of the flexible bladder 54, when in the partially inserted position, is disposed within the annular groove 168 of the vial 52 to thereby form an air-tight, but not a tamper-proof seal between the bladder and vial. In this state, the dispenser 10 may be sterilized and/or transported in a sealed condition prior to filling the dispenser with a medicament or other substance to be contained therein.

The filling of the dispenser 10 is illustrated schematically in FIG. 16B, wherein the flexible bladder 54 and plug 214 are separated from the vial 52 so that the main fluid chamber 55 may be accessed for filling. As can be seen, the annular flange 188 of the bladder may be pulled rearwardly and removed from the annular groove 168 of the vial to thereby open the vial and access the main fluid chamber 55. Preferably, this operation may be carried out by transporting the sterilized dispensers through a sterile transfer port, and filling the dispensers within a sterile filling machine of a type disclosed, for example, in commonly-assigned U.S. Pat. Nos. 5,641,004 and 5,816,772, which are hereby expressly incorporated by reference as part of the present disclosure. During filling, a vacuum may be drawn on the inner chamber 180 of the bladder to collapse the bladder, and the medicament or other substance to be contained therein may be introduced into the main fluid chamber 55. In some embodiments, the main fluid chamber 55 is overfilled, i.e., the amount of medicament supplied to the chamber is greater than the amount that the chamber can hold with the bladder and plug inserted. This helps eliminate the possibility of trapped air in the main fluid chamber upon insertion of the bladder 54 and rear plug 214 (i.e., the main fluid chamber will be filled solely with medicament or other substance).

As shown in FIG. 16C, upon filling the main fluid chamber 55 with the medicament or other substance to be contained therein, the flexible bladder and rear plug assembly are moved into the rigid vial such that the flexible flange 188 of the bladder is moved into engagement with the annular ridge 172, best seen in FIG. 9A, and the rear plug is pressed inwardly until the sealing tabs 226 are snapped into place within the annular groove 168 of the vial to thereby form the airtight and tamper-proof seal. The dispenser 10 may then be installed within the ocular treatment apparatus 8 described above or other suitable apparatus for dispensing medicaments or other fluids, such as nasal inhalers.

In some embodiments, it is desirable to use a vacuum to "catch" any medicament or other substance that overflows from the vial during the insertion of the bladder and rear plug. This is particularly true where the main chamber 55 was overfilled prior to installing the bladder and rear plug, in order to help prevent the possibility of trapped air in the main chamber after the bladder and rear plug are inserted. Otherwise, any excess medicament or other substance will spill out of the vial upon insertion of the bladder and rear plug.

In FIGS. 17 through 20, another embodiment of the dispenser of the present invention is indicated generally by the reference numeral 310. The dispenser 310 is substantially similar to the dispenser 10 described above, and therefore like reference numerals preceded by the numeral "3", or preceded by the numeral "4" instead of the numeral "1", or preceded by the numeral "5" instead of the numeral "2", respectively, are used to indicate like elements. The primary differences of the dispenser 310 in comparison to the dispenser 10 are that (i) the rigid vial 352 and piston 356 are formed as integral components; (ii) the nozzle 358 and slide 360 are formed as integral components; (iii) the flexible bladder 354 defines a smooth cylindrical configuration without any discontinuities or ribs formed thereon; and (iv) the rear plug 514 includes a plurality of inwardly projecting legs 538 for controlling the collapse of the flexible bladder into a predetermined collapsed shape.

Figure 21:
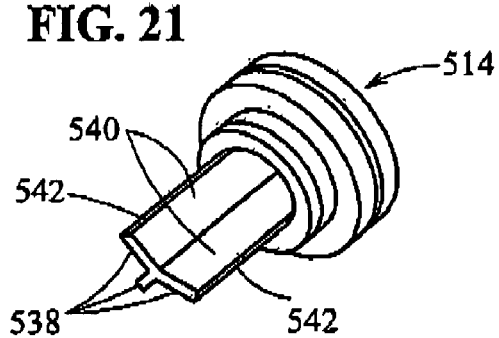
FIG. 21 is a perspective view of the rear plug of the dispenser of FIG. 17.
Figure 22:
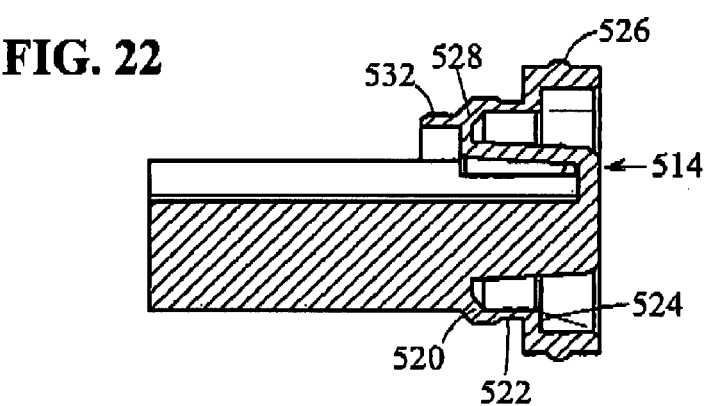
FIG. 22 is cross-sectional view of the rear plug of FIG. 21.
Figure 23:
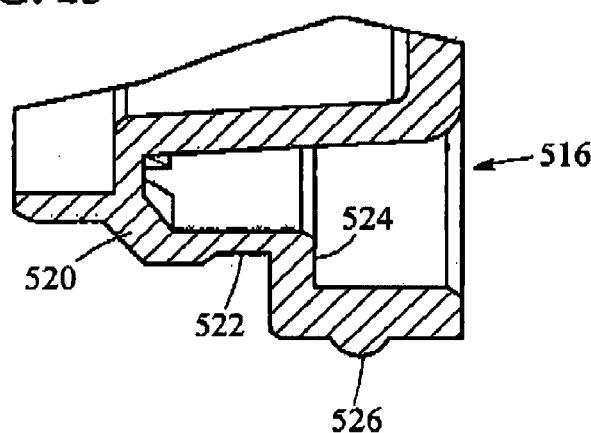
FIG. 23 is a partial, enlarged cross-sectional view of the rear plug of FIG. 21.
Figure 24:
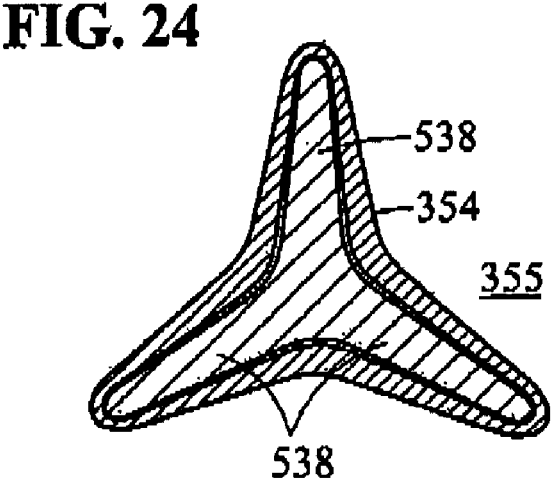
FIG. 24 is a partial, cross-sectional view of the axially-extending and radially-projecting legs of the rear plug of FIG. 21 illustrating the flexible bladder conformably engaging the legs in the predetermined collapsed condition.
Figure 25:
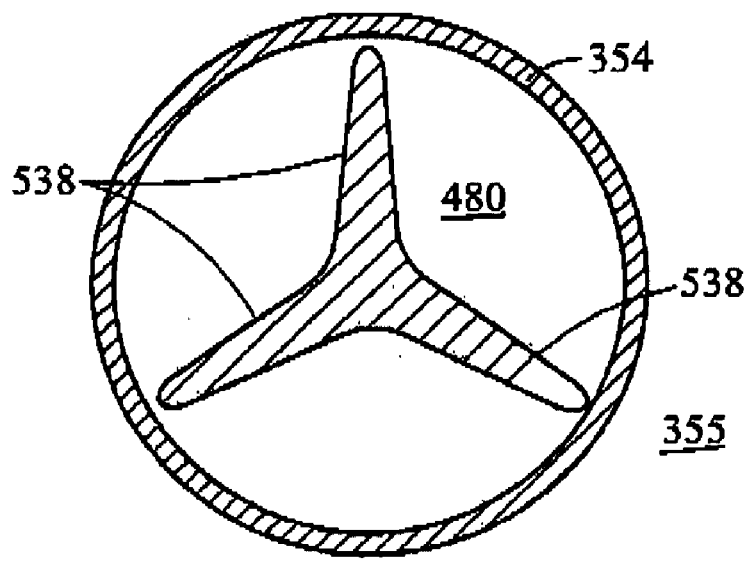
FIG. 25 is a partial, cross-sectional view of the legs of the rear plug and bladder illustrating the bladder in the expanded condition.

As shown in FIGS. 21-23, the rear plug 514 defines a plurality of inwardly projecting, axially-elongated legs 538 defining a framework within the interior chamber 480 of the flexible bladder 354 for controlling the collapse of the bladder into a predetermined collapsed shape. As shown in FIG. 21, the illustrated embodiment of the present invention includes three legs 538 angularly spaced approximately 120° relative to each other about the axis of the rear plug. Each leg lies in a respective plane intersecting the axis of the rear plug and defines approximately planar side surfaces 540 extending radially between the axis of the plug and the inner wall of the rigid vial. As shown in FIG. 19, the radial edge 542 of each leg is radially spaced inwardly relative to the inner wall of the rigid vial to thereby allow movement of the flexible bladder between the radial edges of the legs and the vial. As also shown in FIGS. 19 and 20, the legs 538 extend axially into the interior chamber 480 of the flexible bladder a distance sufficient to allow the legs to control the collapse of the bladder into the predetermined collapsed condition. In the illustrated embodiment, each leg 538 extends along at least about one-half the axial extent of the bladder. As shown in FIG. 24, in the predetermined collapsed condition, the flexible bladder 354 conformably engages the outer surfaces of the legs 538 to thereby allow the main fluid chamber 355 to be filled with a medicament or other substance. Then, as shown in FIG. 25, upon dispensing all of the medicament or other substance from the main fluid chamber 355, the resilient nature of the flexible bladder 354 causes the bladder to expand outwardly away from the legs 538. As shown typically in FIGS. 19 and 20, when fully expanded, the flexible bladder 354 conformably engages the inner wall of the rigid vial to thereby eliminate any ullage or dead space and allow all of the medicament or other substance contained with the main fluid chamber 355 to be dispensed therefrom.

As described above, the flexible bladder 538 is preferably made of a relatively low permeability elastomer, such as a vulcanized butyl rubber, or other rubbers. Such rubbers have demonstrated proven stability and/or compatibility with a wide variety of medicaments, such as pharmaceutical preparations and vaccines, and other substances, and therefore are currently preferred for such applications. In the currently preferred embodiment, the flexible bladder 354 is molded in its expanded condition, and when collapsed, the resilient nature of the bladder tends to force the bladder outwardly toward its expanded condition. The resilient forces within the bladder apply a pressure against the fluid within the main fluid chamber 355, and therefore create a higher pressure in the main fluid chamber 355 in comparison to that of the interior chamber 480 of the bladder. As a result, the pressure differential prevents the ingress of air or other gases or vapors through either the flexible bladder or rigid vial, or otherwise into the main fluid chamber. Thus, the material and/or configuration of the bladder are preferably selected to maintain a pressure differential sufficient to prevent the ingress of air or other gases or vapors into the main fluid chamber under a variety of atmospheric conditions. As described above, the preferred rubber materials disclosed herein for constructing the flexible bladder are exemplary, and numerous other materials that are currently, or later become known for performing the function of the flexible bladder may be equally employed.

Figure 26:
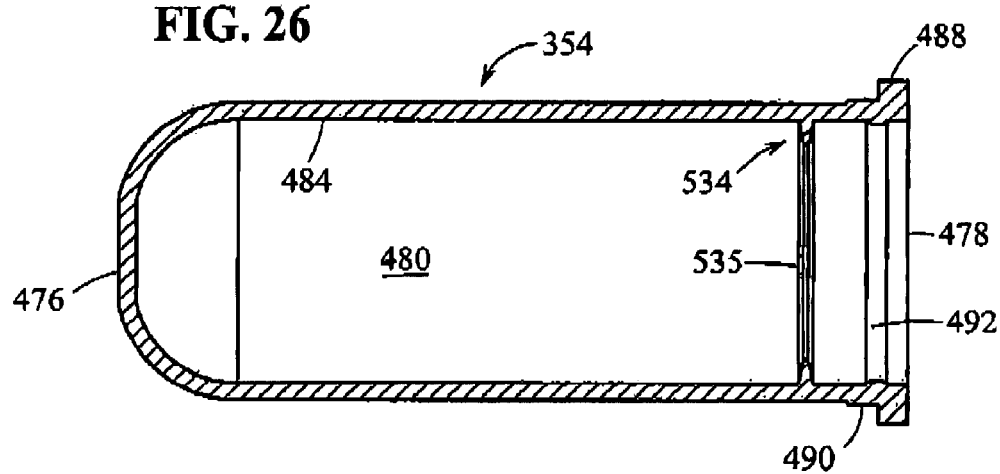
FIG. 26 is a cross-sectional view of the flexible bladder of the dispenser of FIG. 17.
Figure 27:
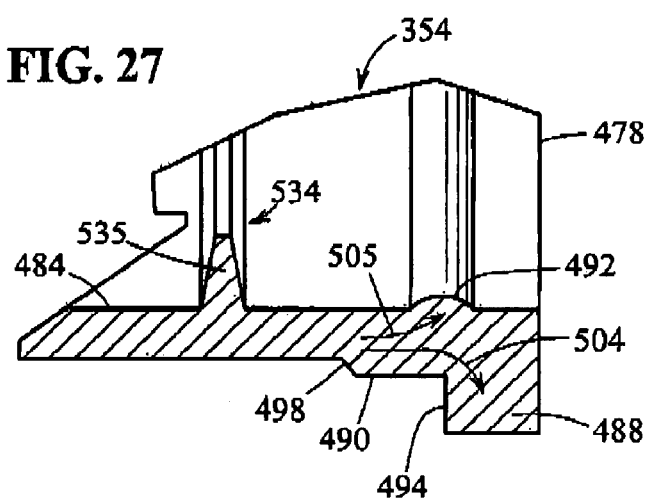
FIG. 27 is a partial, enlarged cross-sectional view of a portion of the flexible bladder of FIG. 26.

As shown in FIGS. 26 and 27, the spaced protuberances 236 described above in connection with the flexible bladder 54 of FIG. 10A may be eliminated depending upon the material of construction and/or other structural features of the flexible bladder 354. In addition, the outer annular lobe may take a shape different than that illustrated above in connection with the bladder of FIG. 10A. As shown in FIG. 27, the outer annular lobe 490 is defined by an annular raised or thickened portion, and a tapered surface 498 extending radially inwardly between the lobe or annular raised portion 490 and the outer peripheral surface of the flexible bladder 354. As shown in FIGS. 19 and 20, the annular raised portion 490 is squeezed against the inner surface of the rigid vial 352 which, in combination with the axially offset, inner annular lobe 492 being fixedly received within the annular groove 522 of the rear end cap (FIG. 23), cause the material of the flexible bladder to creep and/or otherwise flow in the directions of the arrows 504 and 505 in FIG. 27 to thereby persistently maintain an airtight seal between the flexible bladder, rear plug and rigid vial. Thus, the end seal of the flexible bladder is both radially compressed at the axially offset lobes between the rear plug and rigid vial, and is axially compressed at the flange between the rear plug and rigid vial.

As shown typically in FIG. 22, the rear plug 514 defines three apertures 528 approximately equally spaced relative to each other about the axis of the plug. In addition, rather than defining the sealing tabs 226 described above in connection with FIG. 14, the rear plug 514 defines an annular lobe 526 projecting outwardly from the peripheral surface of the rear plug and dimensioned to be snapped into the annular groove 168 of the rigid vial (FIG. 30). The dispenser 310 may be sterilized, temporarily closed, re-opened, and filled in the same manner as described above in connection with FIGS. 16A through 16C.

Figure 28:
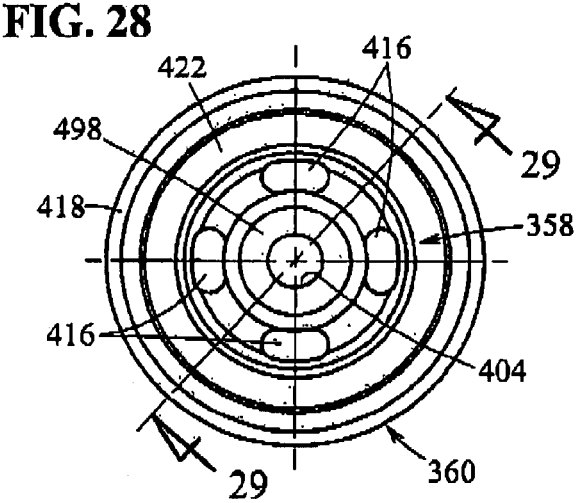
FIG. 28 is a front elevational view of the integral nozzle and slide of the dispenser of FIG. 17.
Figure 29:
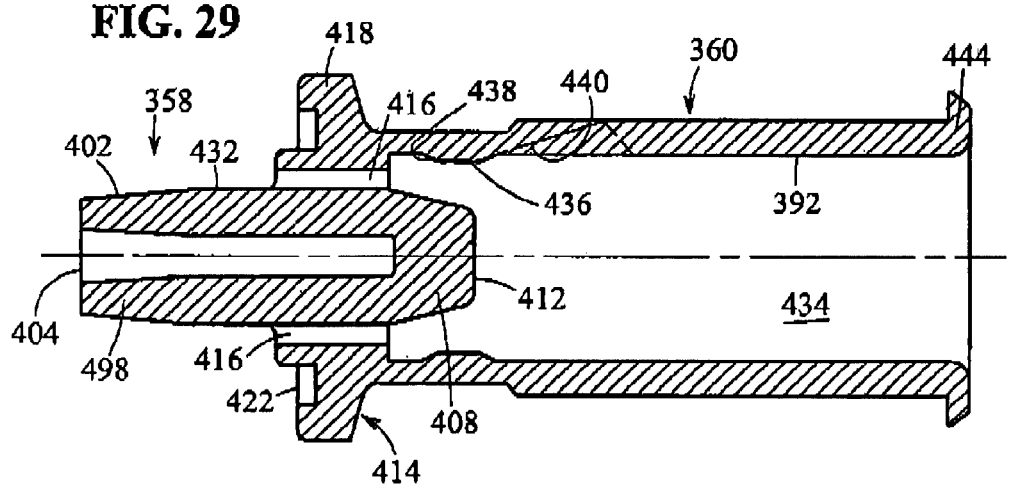
FIG. 29 is a cross-sectional view of the integral nozzle and slide taken along line 29-29 of FIG. 28.

As shown in FIGS. 28 and 29, the nozzle 358 and slide 360 are formed integral with each other. One advantage of this construction over the separate nozzle and slide described above in connection with the previous embodiment, is that the integral construction is typically less costly to manufacture and assemble, and furthermore, reduces the number of seals between components and thereby enhances the overall reliability of the dispenser.

As shown in FIGS. 30 and 31, the piston 356 and rigid vial 352 are also formed integral with each other. As with the integral nozzle and slide described above, one advantage of this construction over the separate piston and slide described above in connection with the previous embodiment, is that the integral construction is typically less costly to manufacture and assemble, and furthermore, reduces the number of seals between components and thereby enhances the overall reliability of the dispenser. In one currently preferred embodiment of the present invention, the integral nozzle 358 and slide 360 is made of a relatively soft material, and the integral piston 356 and vial 352 is made of a relatively hard material. In the operation of the dispenser 310, on the downward stroke of the piston 356, and upon reaching the compression zone 436 of the slide 360 (FIG. 29), the relative hardness and geometry of the illustrated piston causes the piston to force the compression zone 436 of the slide outwardly, or otherwise sealingly engage the compression zone of the slide, and thereby form a fluid-tight seal between the piston and slide. As illustrated in FIG. 30, the tip of the guide wall 394 defines a chamfer for facilitating sliding movement of the piston within the slide.

Forming the integral nozzle and slide of a relatively soft and/or flexible material allows the compression zone 436 of the slide to flex outwardly in order to remove the part from a core pin upon molding the part, and thus enables the nozzle and slide to be integrally molded as a single part. Preferably, compressed air is injected between the core pin and interior surface 392 of the slide to facilitate removal of the part from the core pin (not shown).

As shown in FIGS. 19 and 20, when the flexible bladder 354 is at or near its fully-expanded condition, an annular gap "C" is formed between the bladder and vial. As can be seen, the width of the gap C gradually increases in the axial direction moving from the rear end cap 514 toward the closed end 476 of the bladder. As can be seen, the gap C starts about half-way down the axial extent of the bladder and reaches its maximum width at the curved portion of the bladder between the side wall and end wall 476. The gap C may be created by forming the approximately cylindrical side wall of the flexible bladder 354 with a sufficient draft to form the gap upon insertion of the bladder into the rigid vial. The purpose of the gradually-increasing gap C is to force all fluid within the main fluid chamber 355 in the direction toward the pump 350 and prevent the formation of any pockets of fluid within the main fluid chamber that cannot be dispensed therefrom.

As shown typically in FIGS. 19 and 20, other than the slight differences necessary to create the gap C, the flexible bladder 354 defines approximately the same morphology as the interior surfaces of the rigid vial 352, thus enabling intimate and conforming engagement of the bladder with the rigid vial upon full expansion of the bladder. In addition, the flexible bladder 354 preferably defines in its fully expanded condition an outer diameter (or width) at least equal to or greater than the inner diameter (or width) of the chamber 355 of the rigid vial. These features, in combination with the resilient nature of the flexible bladder, prevent the ingress of gases or vapors into the main fluid chamber 355, and ensure usage of substantially all fluid contained within the chamber.

As shown in FIG. 32, the flexible cover 362 defines an annular mounting flange 380 on one end thereof which is received within a corresponding annular groove 374 formed on the integral piston and rigid vial (FIGS. 30 and 31) to fixedly secure the flexible cover thereto. In addition, the integral piston and rigid vial defines an annular flange 381 adjacent to the annular groove 374 which is received within a corresponding annular groove 382 of the flexible cover (FIG. 32) to further secure the cover thereto.

Figure 33:
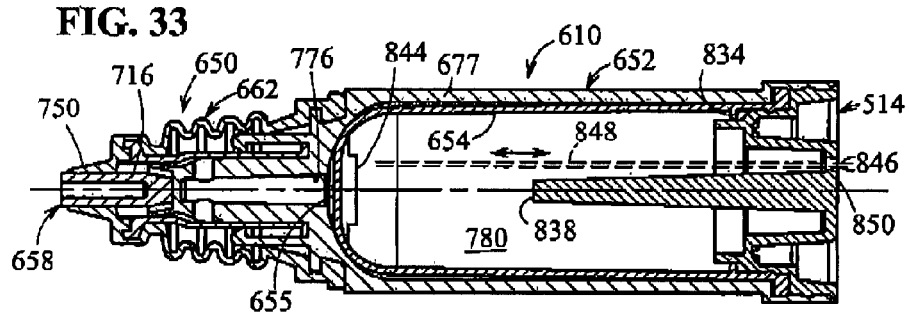
FIG. 33 is a cross-sectional view of another embodiment of the dispenser of the present invention including a resealable portion on the flexible bladder for inserting a needle or like injection member therethrough to fill the dispenser with a medicament or other substance, and allowing the needle holes to be sealed by application of thermal energy thereto.

Turning to FIG. 33, another embodiment of the dispenser of the present invention is indicated generally by the reference numeral 610. The dispenser 610 is substantially the same as the dispenser 310 described above, and therefore like reference numerals preceded by the numeral "6" instead of the numeral "3", the numeral "7" instead of the numeral "4", or the numeral "8" instead of the numeral "5", respectively, are used to indicate like elements. The primary difference of the dispenser 610 in comparison to the dispenser 310 is that the dispenser 610 includes a resealable bladder to allow the bladder to be filled in a sterile filling machine of the type disclosed in co-pending U.S. patent application Ser. No. 09/781,846, filed Feb. 12, 2001, now U.S. Pat. No. 6,604,561, which is assigned to the same Assignee as the present invention, and is hereby expressly incorporated by reference as part of the present disclosure.

As shown in FIG. 33, the flexible bladder 654 includes on its closed end 776 a resealable portion 844 overlying the closed end 776. In the illustrated embodiment, the flexible bladder 354 is formed of a first material compatible with the predetermined medicament or other substance to be contained within the main fluid chamber 655, and defines on its external side a medicament-exposed surface intended to be exposed or otherwise placed in contact with the predetermined medicament or other substance contained within the main fluid chamber. The resealable portion 844 is penetrable by a needle or like filling member for introducing the predetermined medicament or other substance through the flexible bladder and into the main fluid chamber. The penetrable region of the flexible bladder is formed of a vulcanized rubber, and therefore is substantially infusible in response to the application of thermal energy thereto. The penetrable region of the resealable portion 844, on the other hand, is fusible in response to the application of thermal energy thereto, thus allowing the penetrable region of the resealable portion to be hermetically sealed upon removing the needle or like filling member therefrom. In the illustrated embodiment, the resealable portion 844 is insert molded onto the rubber bladder during which the thermoplastic resealable layer bonds itself to the underlying rubber layer. If necessary, a mechanical fastener of a type known to those skilled in the pertinent art may be used to facilitate attachment of the resealable portion to the end wall of the flexible bladder.

The resealable member 844 is preferably made of a resilient polymeric material, such as a blend of the polymeric material sold by GLS under the registered trademark KRATON® and a low-density polyethylene, such as the polyethylene sold by Dow Chemical Co. under the trademarks ENGAGE™ or EXACT™. An important feature of the resealable member 844 is that it be resealable to form a gas-tight seal after inserting a needle, syringe or like injection member through the resealable member. Preferably, the resealable member can be sealed by heating the area punctured by the needle in a manner known to those skilled in the pertinent art and described in the above-mentioned co-pending patent application. One advantage of the blended polymer described above is that it is known to minimize the degree to which the medicament or other substance can be absorbed into the polymer in comparison to KRATON® itself.

As shown in FIG. 33, the rear plug 514 defines a filling aperture 846 formed therethrough and overlying the resealable member 844. As shown in broken lines in FIG. 33, a double lumen needle or like injection member 848 may be reciprocally moved through the filling aperture 846 to, in turn, pierce both the resealable member 844 and underlying closed end 776 of the flexible bladder. The injection member 848 is coupled in fluid communication with a source (not shown) of medicament or other substance to be contained within the main fluid chamber 655 and is actuated to fill the chamber with the medicament or other substance. Upon filling the chamber, the flexible bladder 654 is collapsed into its predetermined collapsed condition, as shown above, and the needle is withdrawn. If necessary, a vacuum may be drawn on the interior chamber 780 of the flexible bladder during filling to facilitate collapse of the bladder. Upon withdrawing the needle, a laser or other energy source (not shown) transmits a beam of laser radiation onto the penetrated region of the resealable member to seal the needle hole in the manner described in the above-mentioned co-pending patent application and thereby maintain the medicament or other substance contained therein in a sterile, hermetically sealed condition. The filling aperture 846 may be sealed with a cap 850 (shown in broken lines) to maintain the interior chamber 780 of the flexible bladder in a sealed condition.

In certain embodiments of the present invention, at least a portion of the resealable portion 844 is formed of a thermoplastic material defining a needle penetration region that is pierceable with a needle to form a needle aperture therethrough, and is heat resealable to hermetically seal the needle aperture by applying laser radiation at a predetermined wavelength and power thereto. In an alternative embodiment of the present invention, the entire body of the portion 844 is formed of the thermoplastic material. In another embodiment of the invention as described above, an overlying portion of the resealable portion if formed of the fusible thermoplastic material, and an underlying portion of the resealable portion is formed of an infusible material, such as vulcanized rubber. Preferably, each thermoplastic portion or body defines (i) a predetermined wall thickness in an axial direction thereof, (ii) a predetermined color and opacity that substantially absorbs the laser radiation at the predetermined wavelength and substantially prevents the passage of the radiation through the predetermined wall thickness thereof, and (iii) a predetermined color and opacity that causes the laser radiation at the predetermined wavelength and power to hermetically seal the needle aperture formed in the needle penetration region thereof in a predetermined time period and substantially without burning the needle penetration region (i.e., without creating an irreversible change in molecular structure or chemical properties of the material). In one embodiment, the predetermined time period is approximately 2 seconds, is preferably less than or equal to about 1.5 seconds, and most preferably is less than or equal to about 1 second. Also in this embodiment, the predetermined wavelength of the laser radiation is about 980 nm, and the predetermined power of each laser is preferably less than about 30 Watts, and most preferably less than or equal to about 10 Watts, or within the range of about 8 to about 10 Watts. Also in this embodiment, the predetermined color of the material is gray, and the predetermined opacity is defined by a dark gray colorant added to the resealable portion material in an amount within the range of about 0.3% to about 0.6% by weight.

In addition, the thermoplastic material may be a blend of a first material that is preferably a styrene block copolymer, such as the materials sold under either the trademarks KRATON or DYNAFLEX, and a second material that is preferably an olefin, such as the materials sold under either the trademarks ENGAGE or EXACT. In one embodiment, the first and second materials are blended within the range of about 50:50 by weight to about 95:5 by weight (i.e., first material: second material). In one such exemplary embodiment, the blend of first and second materials is about 50:50 by weight. The benefits of such blends over the first material by itself are improved water or vapor barrier properties, and thus improved product shelf life; improved heat sealability; a reduced coefficient of friction; improved moldability or mold flow rates; and a reduction in hystereses losses. As may be recognized by those skilled in the pertinent art based on the teachings herein, these numbers and materials are only exemplary, however, and may be changed if desired or otherwise required in a particular system.

Figure 1B:
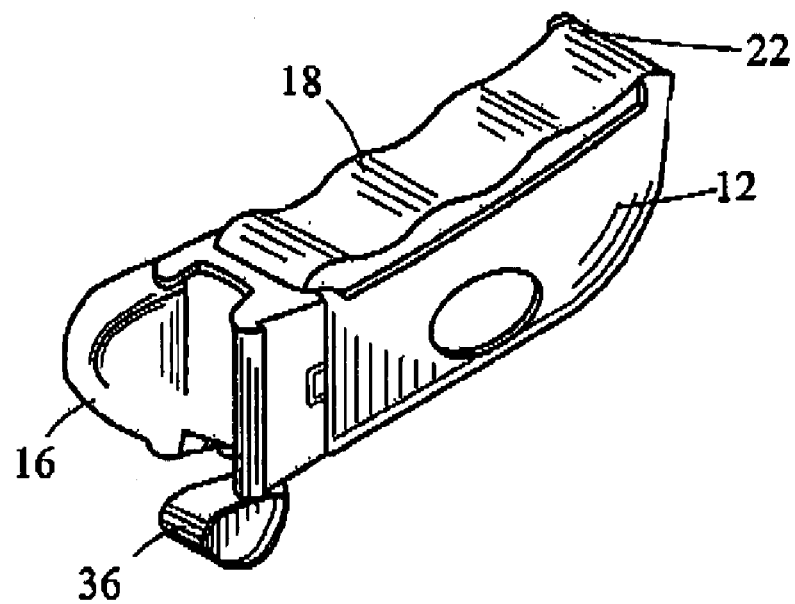
FIG. 1B is a perspective view of the ocular treatment apparatus of FIG. 1.
Figure 1D:
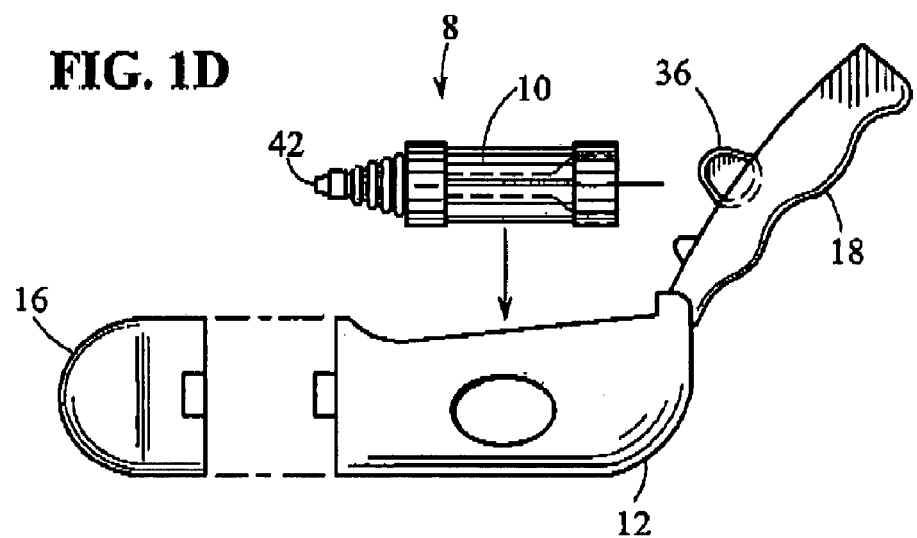
FIG. 1D is an exploded view, in side elevation, of the ocular treatment apparatus of FIG. 1B.
Figure 1C:
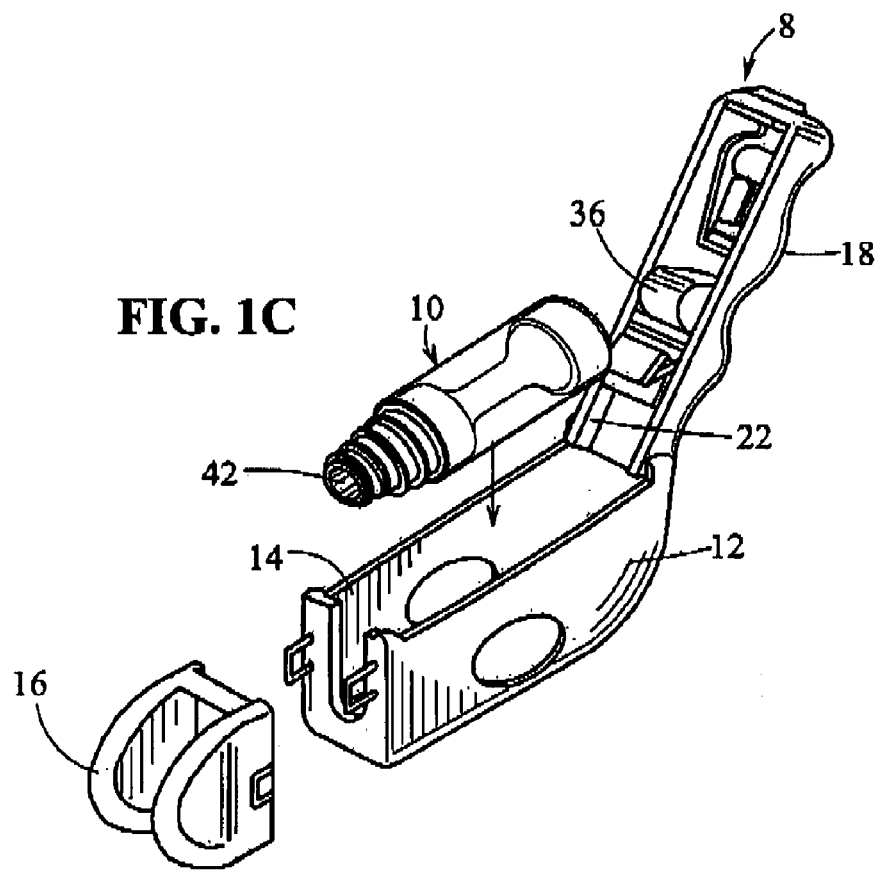
FIG. 1C is an exploded view, in perspective, of the ocular treatment apparatus of FIG. 1B.
Figure 34A:
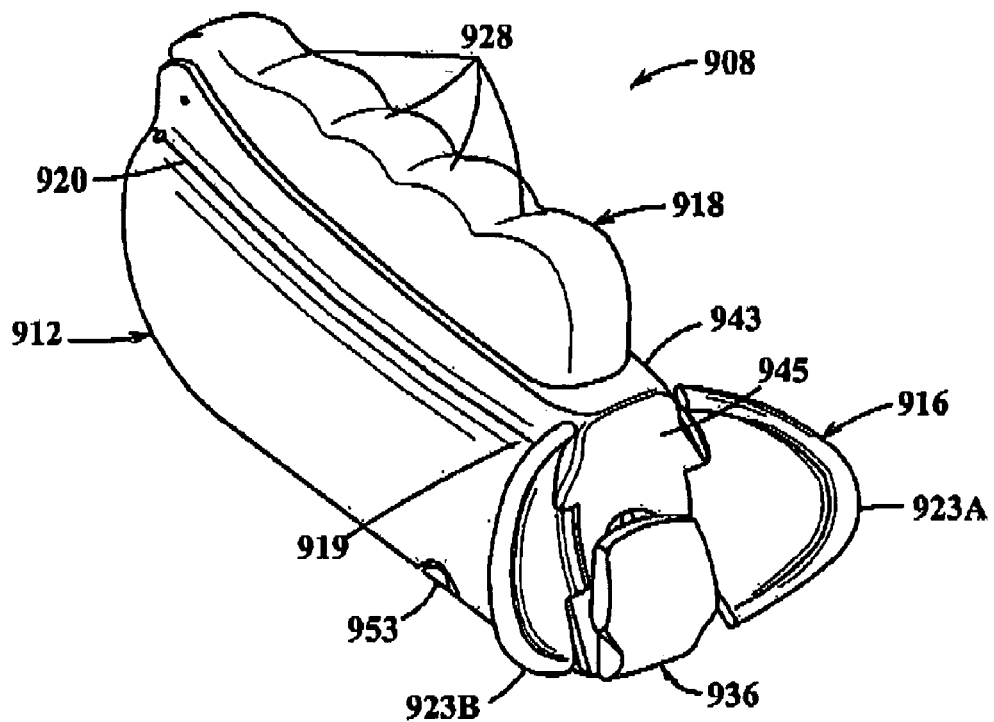
FIG. 34A is a front-top perspective view of an ocular treatment apparatus according to another embodiment of the present invention.
Figure 34B:
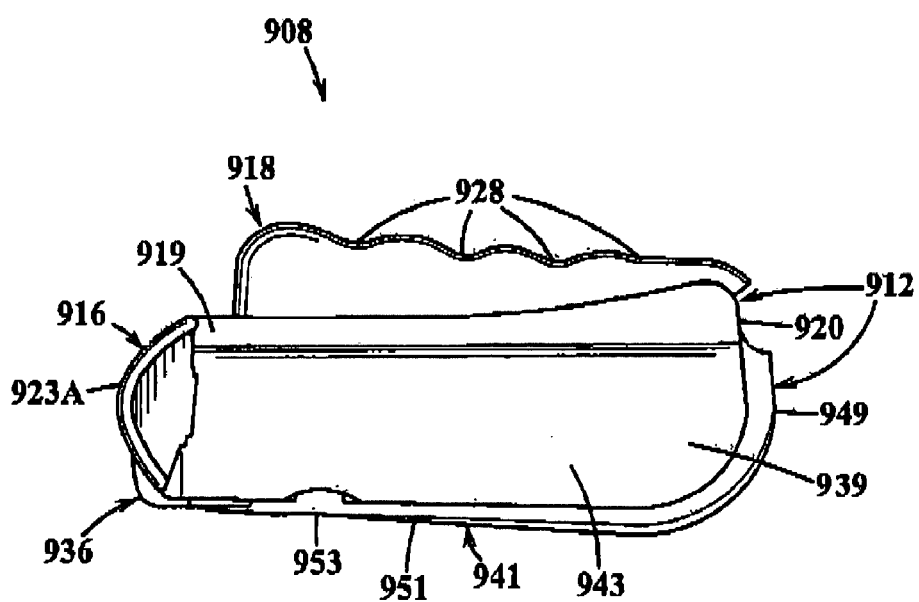
FIG. 34B is a side elevational view of the ocular treatment apparatus of FIG. 34A.
Figure 34C:
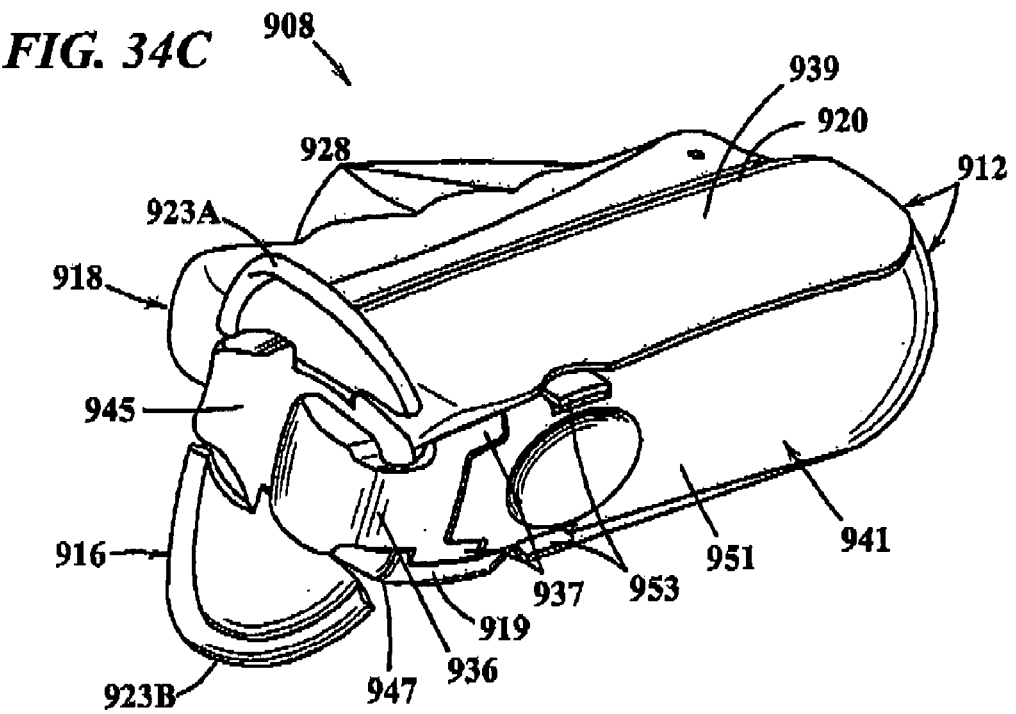
FIG. 34C is a front-bottom perspective view of the ocular treatment apparatus of FIG. 34A.

FIGS. 34A-34C show an ocular treatment apparatus 908 according to another aspect of the present invention. As will be apparent in view of the description hereinafter, the treatment apparatus 908 is similar in many respects to the treatment apparatus 8 (FIG. 1B).

Figure 37:
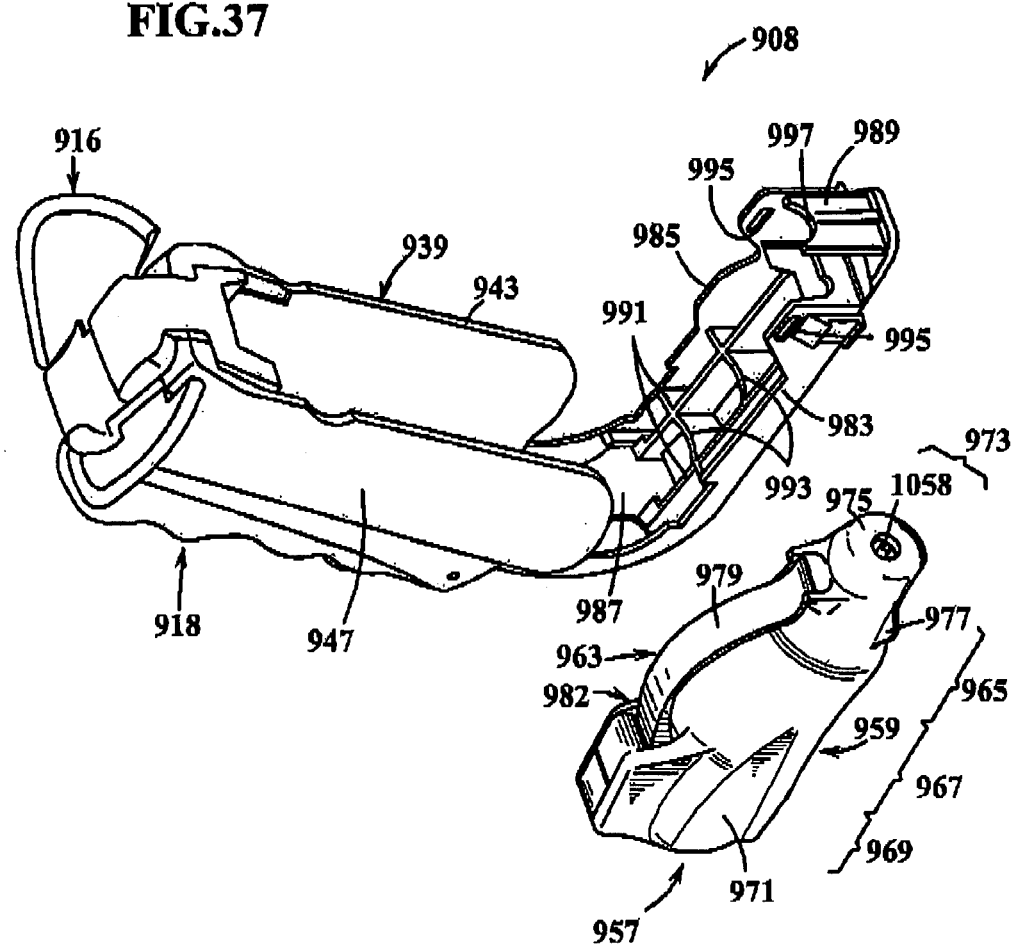
FIG. 37 is a partially exploded view, in perspective, of the ocular treatment apparatus of FIG. 35A.

Referring to FIG. 34A, the treatment apparatus 908 includes a housing 912, an eye cover 916 and a trigger 918. The housing 912 has a first end 919 and a second end 920. The eye cover 916 has wings 923A, 923B, which are pivotably connected to the first end 919 of the housing 912. The trigger 918, which is elongated and has finger grooves 928, is pivotably connected to the second end 920 of the housing 912. The housing 912 generally defines an interior cavity (details of the inner cavity are shown in FIG. 37).

The apparatus 908 further includes an eyelid depressor 936, which has two spaced apart fingers 937 (FIG. 34C) pivotally connected to the first end 919 of the housing 912 (i.e., the same end of the housing to which the eye cover 916 is connected).

Referring now to FIGS. 34B, 34C, the housing 912 has two portions 939, 941. The first portion 939 (hereafter the "main portion" 939) of the housing is generally U-shaped to define three side walls: a first side wall 943, a second side wall 945, and a third side wall 947. The second portion 941 (hereafter the "cover portion" 941) is generally L-shaped to define a fourth side wall 949 and a fifth side wall 951 (the fifth side wall being referred to herein as a bottom wall). One end of the cover portion 941 is pivotally mounted to an upper region of the main portion 939, as will be further described hereinafter. The other end of the cover portion 941 has prongs 953 adapted to engage the main portion 939. The engagement locks the main portion 939 to the cover portion 941 to provide a "closed state" (as shown) to thereby conceal the inside of the housing 912. Forcing the prongs 953 toward one another causes the prongs 953 to disengage from the main portion 939, which frees one or both of the first and cover portions 939, 941 to pivot (relative to the other) to provide an "open state" and thereby expose the interior cavity generally defined by the housing 912 (see FIGS. 35A-35B, 37).

The pronged end of the cover portion 941 extends into the region between the spaced apart fingers 937 (FIG. 34C) of the eyelid depressor 936. The spacing between the fingers 937 is sufficient to ensure that the eyelid depressor 936 and the cover portion 941 are each able to pivot without interference from the other.

Figure 35A:
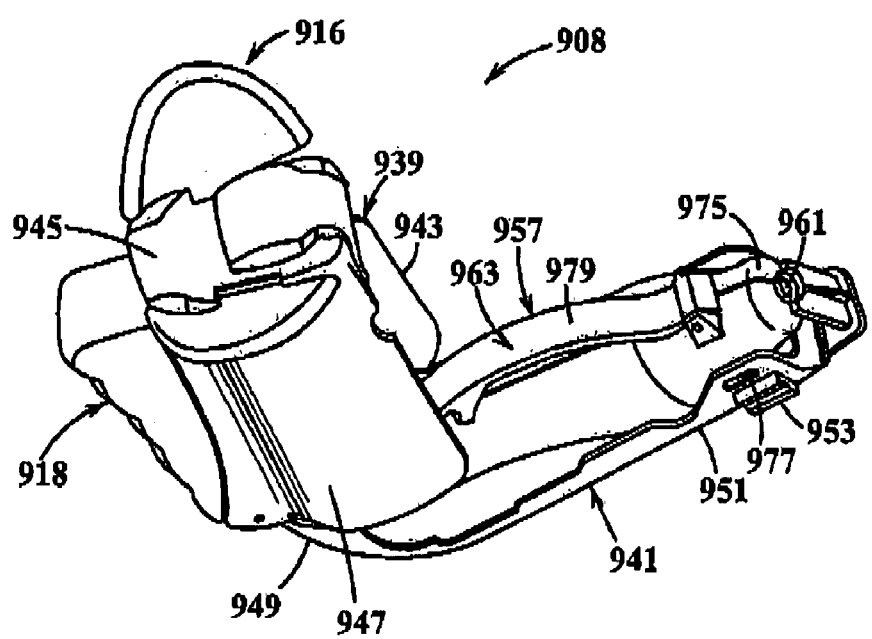
FIG. 35A is a perspective view of the ocular treatment apparatus of FIG. 34A, with the housing in an open state.
Figure 35B:
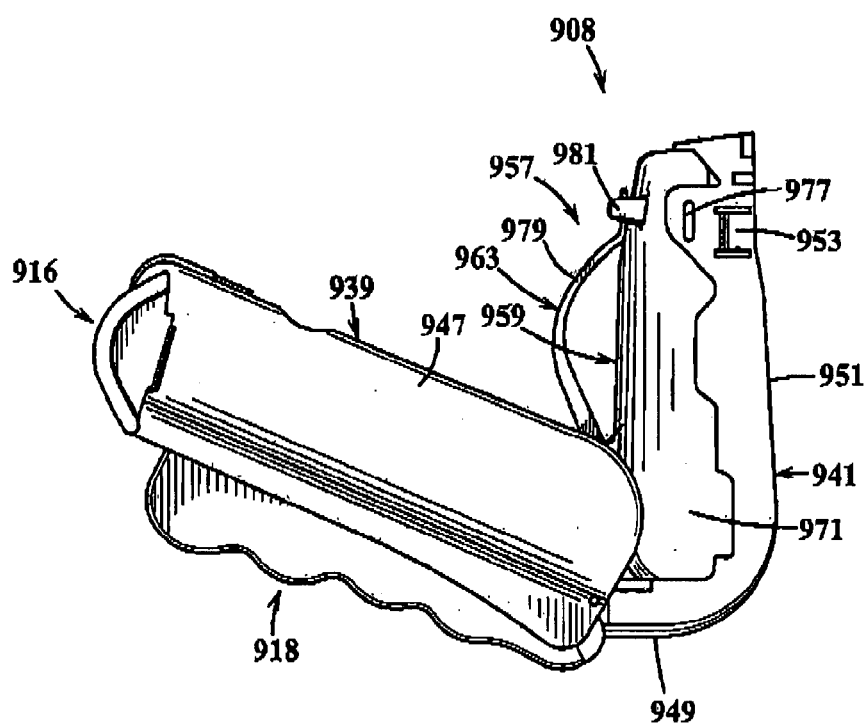
FIG. 35B is a side elevational view of the ocular treatment apparatus of FIG. 34A, with the housing in the open state.
Figure 36:
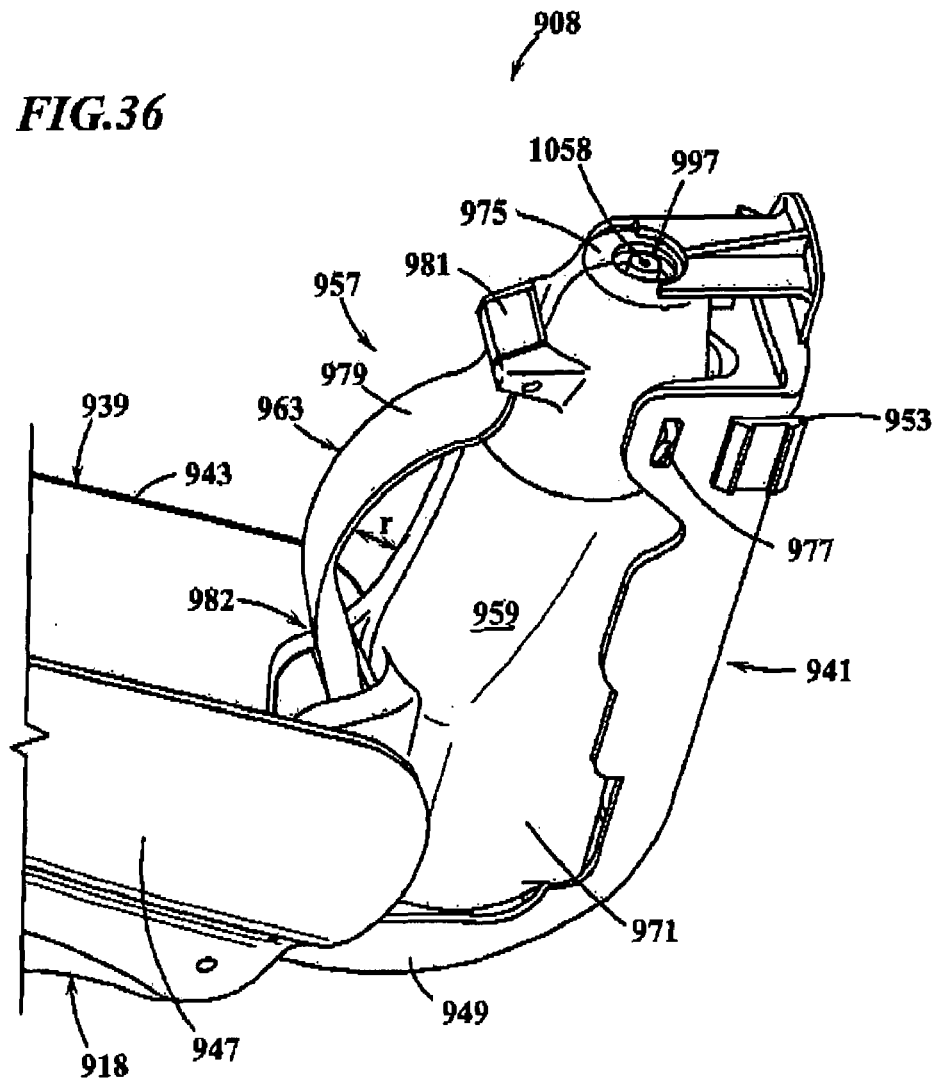
FIG. 36 is an enlarged perspective view of a portion of the cartridge of FIG. 35A.

FIGS. 35A-35B show the treatment apparatus 908 with the housing 912 in the open state, whereby a cartridge 957 in accordance with one embodiment of one aspect of the present invention can be seen. The cartridge 957 is used for storing and delivering medicament (or other substance). FIG. 36 is an enlarged perspective view of a portion of the treatment apparatus 908, showing further details of the cartridge 957 and the cover portion 941 of the housing 912.

FIG. 37 is a partially exploded view, in perspective, of the ocular treatment apparatus 908, showing still further details of the cartridge 957 and the cover portion 941 of the housing 912.

Referring to FIGS. 36, 37, the cartridge 957 includes a casing 959, a nozzle 1058, and an actuator 963. The casing 959 can be viewed as having an anterior region 965, a mid region 967, and a posterior region 969 (FIG. 36). The anterior region 965 has a truncated conical-like shape. The mid and posterior regions 967, 969 are approximately cylindrical in shape except for two flattened (i.e., substantially planar) side walls 971. Note that one of the flattened side walls is shown. The other flattened side wall is on the opposite side of the cartridge 957. Providing flattened side walls narrows the width 973 of the cartridge 957 to enable the cartridge to fit within the interior cavity of the housing. The diameter of the posterior region 969 is slightly greater than the diameter of the mid region 967. The anterior region 965 of the casing has a wall 975 with an aperture that receives a tip of the nozzle 1068 and is in fluid communication with a fluid path out of the nozzle 1068. In addition, projections 977 extend radially from the anterior region of the casing 959. As will be further described hereinafter, the projections 977 are adapted to engage features on the cover portion 941 of the housing 912, or to engage an eyelid depressor when used without the housing 912.

In this embodiment, the casing comprises two halves, each of which is integrally formed. The two halves are ultimately joined together during fabrication of the cartridge.

The actuator 963 comprises a lever 979, one end of which is pivotably connected to the anterior region 965 of the casing 957 via a hinge 981. The other end of the lever 979 extends into an opening in the posterior region 969 of the casing 957. In this embodiment, the lever 979 is formed so as to have a radius "r".

The cartridge 957 is adapted to be inserted into the cover portion 941 prior to using the treatment apparatus 908. If the cartridge becomes empty of medicament, the cartridge 957 may be removed from the cover portion 941 and replaced by another cartridge. In this embodiment, the cartridge is a self contained. Moreover, the cartridge is a substantially sealed unit, meaning that there are substantially no openings in the outside surface of the cartridge (other than the medicament flow path provided through the one way valve of the nozzle) that do not have a seal.

To that effect, the cover portion 941 has walls 983, 985, and abutments 987, 989 that define a longitudinally extending seat to receive the cartridge 957. Longitudinal ribs 991 and transverse ribs 993 disposed on the inside of the cover portion 941 further define the seat for the cartridge 957 and cooperate with the walls, 983, 985, and abutments 987, 989, to properly position the cartridge 957. The walls limit lateral movement of the cartridge 957. The abutments 987, 989 limit axial movement. In addition, each of the walls has an opening 995 that cooperates with a respective projection 977 on the cartridge 957 so as to releasably retain the cartridge 957 to the cover portion 941 and further position the cartridge 957 relative to the cover portion 941 and the housing 912. The width of the cover portion 941 is small enough to fit between the first and third side walls 943, 947 of the main portion 939 of the housing 912. The abutment 989 has a slot 997 in flow communication with a flow path out of the nozzle 1068.

Figure 38:
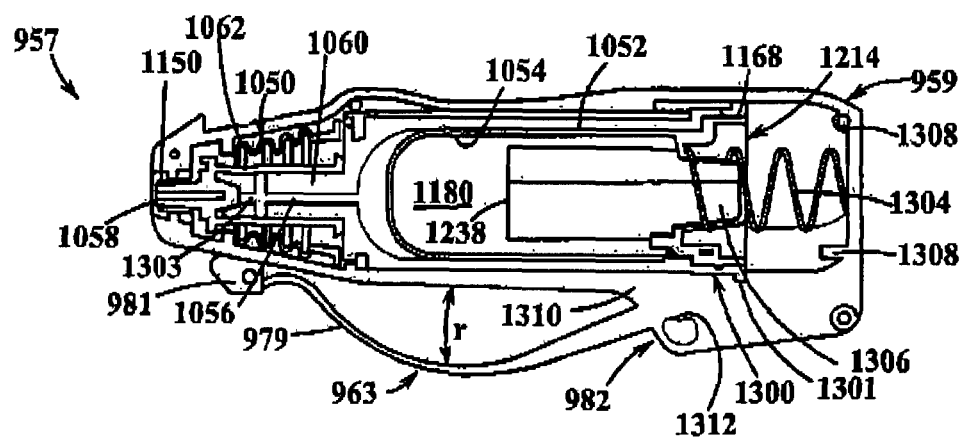
FIG. 38 is a partially broken away, side elevational view of the cartridge of FIG. 35A.

FIG. 38 is a partially broken away, side elevational view of one embodiment of the cartridge of FIG. 357. In this embodiment, the cartridge 957 includes a pump assembly 1050, a rigid vial 1052, a flexible bladder 1054, a piston 1056, a nozzle 1058, a slide 1060, a pump cover 1062, a nozzle cover 1150, a cavity 1180, a rear plug 1214, and a valve 1234, which are similar to the pump assembly 350, rigid vial 352, flexible bladder 354, piston 356, nozzle 358, slide 360, pump cover 362, nozzle cover 450, cavity 480, rear plug 514, and valve 534 described above with respect to FIGS. 17-20.

Hereafter reference numerals preceded by the numerals "10" instead of the numeral "3" indicate similar elements. Similarly, reference numerals preceded by the numerals "11" instead of the numeral "4" indicate similar elements, and reference numerals preceded by the numerals "12" instead of the numeral "5" indicate similar elements. For example, the rear plug 1214 includes a plurality of inwardly projecting legs 1238 for controlling the collapse of the flexible bladder into a predetermined collapsed shape. The rigid vial 1052 includes a peripheral groove 1168 and has an annular ridge 1172 for engaging the flexible bladder 1054.

Figure 39A:
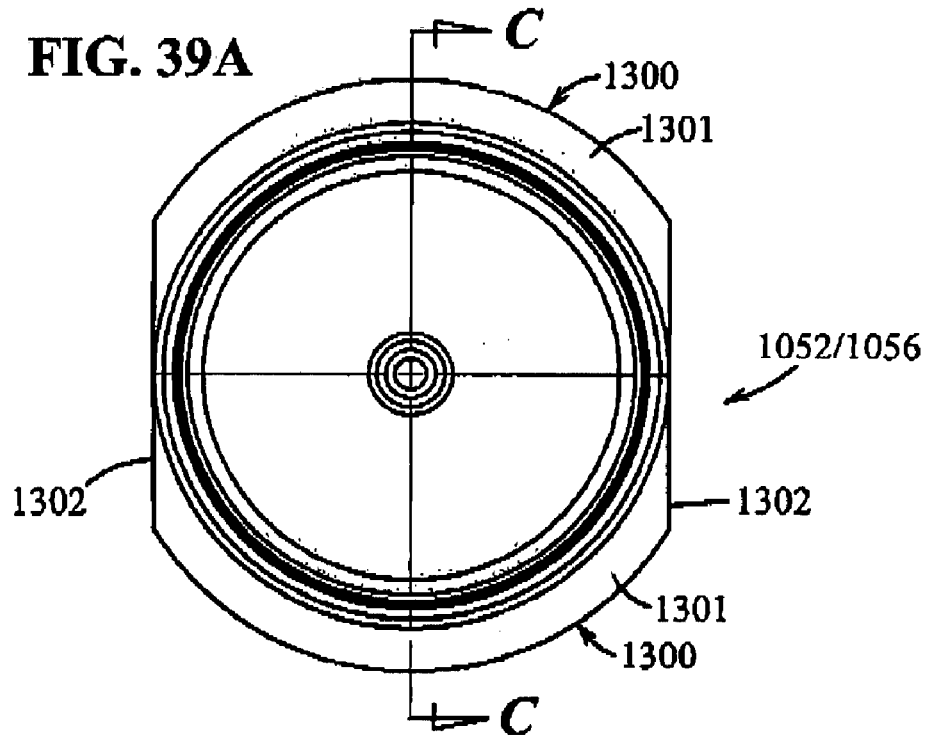
FIG. 39A is a rear elevational view of the integral piston and vial of FIG. 38.
Figure 39B:
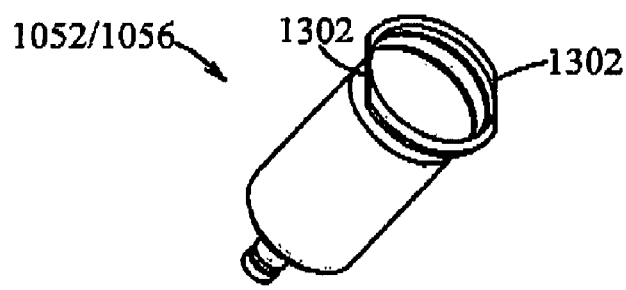
FIG. 39B is a rear-bottom perspective view of the integral piston and vial of FIG. 38.
Figure 39C:
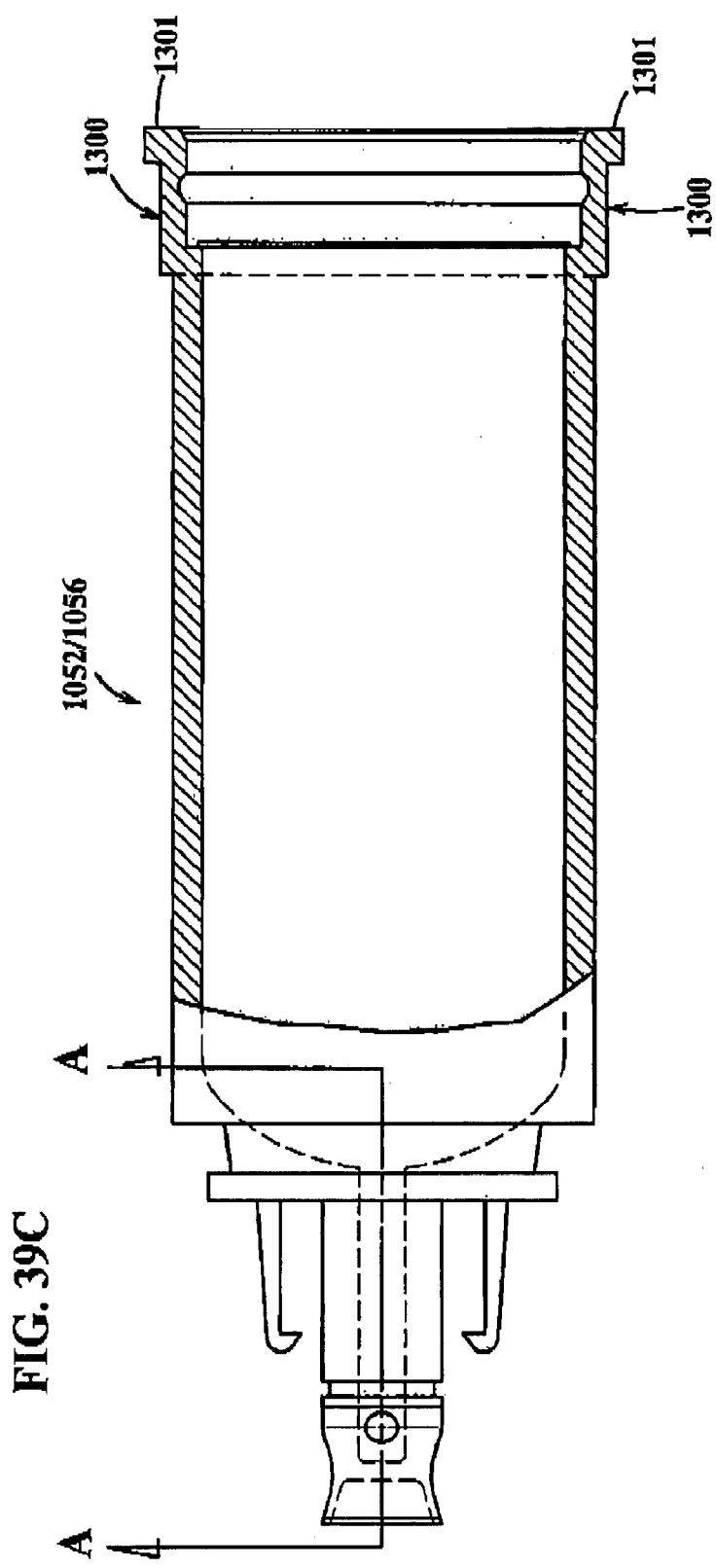
FIG. 39C is a side elevational view of the integral piston and vial of FIG. 38.

There are however, three main differences to note. First, the rigid vial 352 has an increased diameter portion and an annular ridge (see increased diameter portion 170 and annular ridge 172 (FIG. 9A)); however, in this embodiment, the vial 1052 has only of a portion of an increased diameter portion 1300 (FIGS. 39A, 39B) and only a portion of an annular ridge 1301 (FIGS. 39A, 39B). This is because the vial 1052 has flattened side walls 1302 (FIGS. 39A, 39B), which narrow the width of the vial so as to enable the vial 1052 to fit within the interior cavity defined by the casing 959. As stated above, the casing 959 has flattened side walls 971 (FIGS. 35-37) in order to fit within the interior cavity defined by the housing 912. Although not shown, the flattened side walls 1302 (FIGS. 39A, 39B) of the vial 1052 are circumferentially aligned with and/or abut the flattened side walls 971 (FIGS. 35-37) of the casing 959. Second, the slide 1060 has a neck 1303 that is approximately fifty percent shorter in length than the neck of the slide 360 (see neck 136 (FIG. 7)). This is so that the treatment apparatus will dispense approximately one half the dosage dispensed by the apparatus of FIGS. 17-20. Third, the length of the piston 1056 is shorter than the length of the piston 356 order to accommodate the shorter length of the neck on the slide 1060.

It should be recognized that the dosage can be precisely controlled by controlling the volume defined by the neck 1303. This is because, referring also now to FIGS. 4, 7, once the annular wall 94 (FIG. 4) of the piston 56 (FIG. 4) reaches the neck 1303 of the slide 1060, the annular wall 94 forms a seal that prevents medicament from backflowing into the main chamber 55, and consequently, the amount of medicament trapped in the neck 1303 of the slide 1060 defines the amount of medicament to be expelled from the nozzle. Thus, for example, in some embodiments, the dosage amount is precisely ten micro liters (ul). However, as may recognized by those of ordinary skill in the pertinent art based on the teachings herein, the dosage volume may be precisely controlled or set to virtually any dosage volume that may be required for a particular application, or otherwise desired, including without limitation the following other dosage volumes: 15, 20, 25, 30, 35 or 40 microliters. Accordingly, a significant advantage of the currently preferred embodiments of the present invention is that the dosage volume can be precisely controlled, for example, to maximize the pharmacological benefits of a particular medicament, or to set the dosage volume to be substantially equal to (or to otherwise correspond to) the volume that can be received and retained within an ocular cul-de-sac.

The cartridge 957 further includes a spring 1304. The spring 1304 is disposed between the external surface of the posterior wall of the rear plug 1214 and the internal surface of the posterior wall of the casing 959. A guide 1306 on the rear plug and longitudinal ribs 1308 on the casing 959 retain the spring in a desired position. As will be described hereinafter, the spring 1304 provides a force that helps overcome friction and propel the medicament dosage out of the cartridge 957 and into the eye.

As stated above, one end of the lever 979 is pivotably connected to the casing 959 via the hinge 981. The other end of the lever 979 extends into the opening 982 in the casing 959. The casing has a pair of surfaces 1310, 1312 that seal against the end of the lever extending into the casing 959. The radially inner one of these surfaces 1310 seal against a radially inner surface 1314 of the lever 979. The radially outer one of these surfaces 1312 seals against a radially outer surface 1316 of the lever 979.

In the operation of the cartridge, a radially inward force is applied to the lever 979. This forces a portion 1318 of the lever 979 into contact with the casing 959, which causes the lever 979 to straighten, and thereby causes the end of the lever to move in a direction toward the posterior end of the cartridge and engage the portion of the annular ridge 1301 of the vial 1052. The lever continues to move toward the posterior end of the cartridge, which drives the piston 1056 in the same direction to thereby prime the pump (as described in detail above) and compress the spring 1304. With increasing radial force applied to the lever 979, the free end of the lever 979 eventually disengages from the portion of the annular ridge 1301 and thereby releases the integral vial 1052 and piston 1056 from the force of the lever 979. As a result, and due to the resiliency or spring-like nature of the pump assembly 1050 (as described in detail above) as well as the spring force of the compressed spring 1304, the integral piston 1056 and vial 1052 move in a direction toward the anterior end of the cartridge 957 and, in turn, force a predetermined dosage of medicament (or other substance) from the nozzle 1058.

Figure 40A:
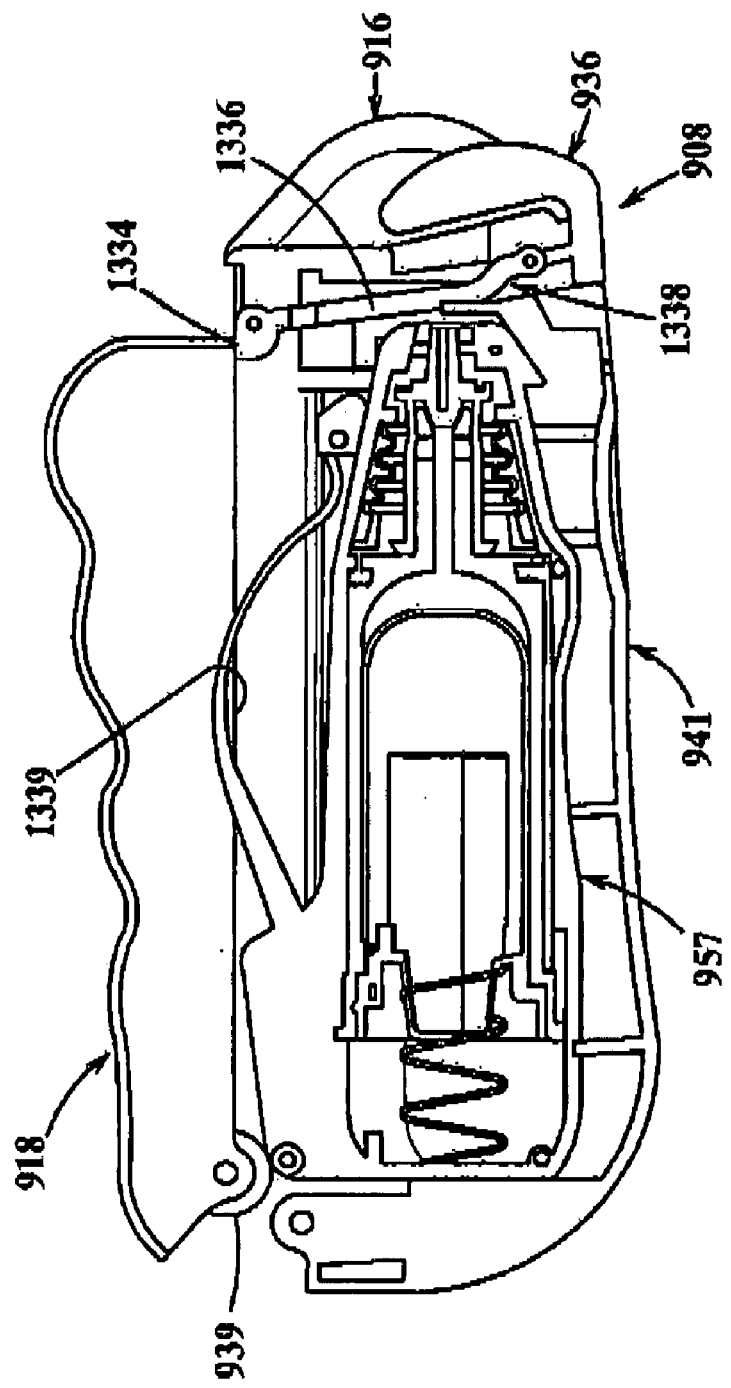
FIG. 40A is a partially broken away, side elevational view of the ocular treatment apparatus of FIG. 34A.
Figure 40B:
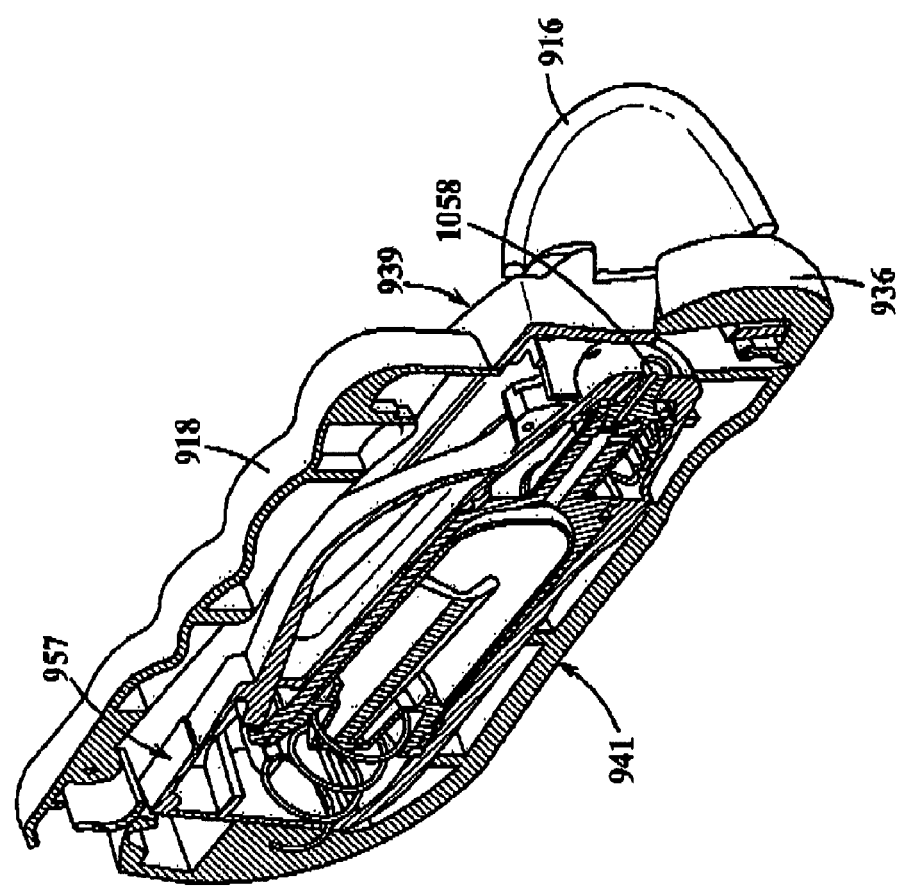
FIG. 40B is a partially broken away, front-bottom perspective view of the ocular treatment apparatus of FIG. 34A.

FIGS. 40A-40B are partially broken away views of the treatment apparatus 908.

Figure 40C:
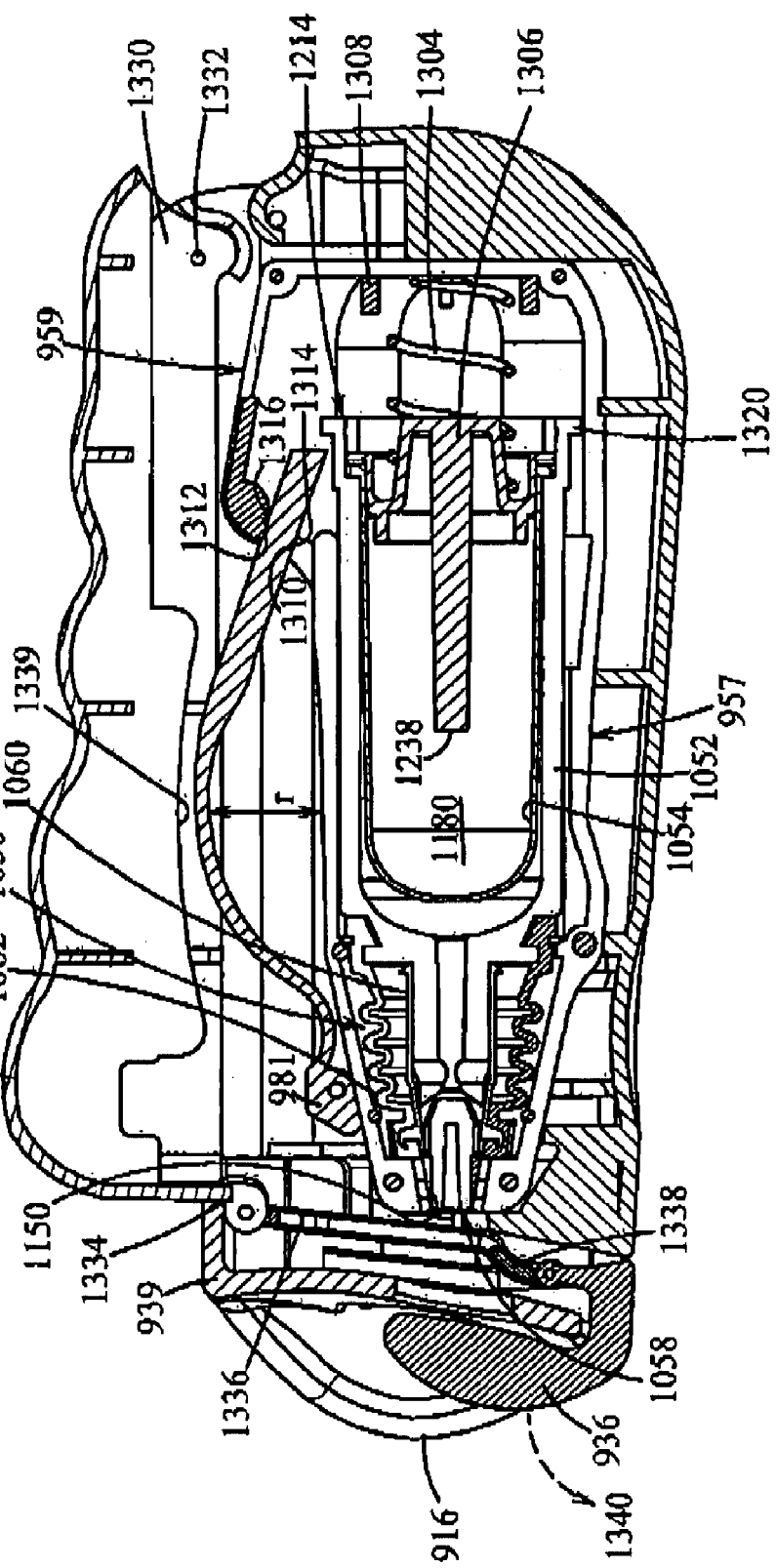
FIG. 40C is a cross-sectional view of the ocular treatment apparatus of FIG. 34A.

FIG. 40C is a cross-sectional view of the ocular treatment apparatus of FIG. 34A. Referring to FIG. 40C, the trigger 918 has one end 1330 pivotably connected to the housing 912 via a pin 1332. The other end 1334 of the trigger 918 is connected to an arm 1336 with a curved end 1338, which connects to an end of the eyelid depressor 936, for pivotably moving the eyelid depressor 936 upon actuating the trigger 918. The trigger 918 further includes a surface 1339 adapted to transmit an applied force to the lever 979 of the cartridge 957.

In use, the eye cover 916 of the treatment apparatus 908 is placed adjacent to the tissue surrounding the eye with the eyelid depressor 936 engaging the tissue adjacent to the ocular cul-de-sac. Upon squeezing the trigger 918, the eyelid depressor 936 rotates in the direction of the arrow 1340, and in turn moves the tissue adjacent to the eye to expose the ocular cul-de-sac. Rotation of the eyelid depressor 936 is caused by the arm 1336 which thereby uncovers the nozzle 1058. Simultaneously, the surface 1339 of the trigger 918 applies force to the lever 979 of the cartridge 957, which causes the cartridge to deliver a predetermined dosage of medicament (or other substance) from the nozzle 1058, as described above.

In some embodiments, the wings 923A, 923B of the eye cover 916 are sufficiently pivotable so as to enable the wings 923A, 923B to cover at least a portion of the nozzle 1058 when the apparatus 908 is not in use.

It should be recognized that, in this embodiment, the pivot for the trigger 918 and the pivot for the lever 979 are on opposite sides of the apparatus. That is, the pivot for the trigger 918 is located generally in the posterior region of the apparatus 908, the pivot for the lever 979 is located generally in the anterior portion of the apparatus 908. In some embodiments, the pivot for the trigger 918 and the pivot for the lever 979 are approximately at opposite ends of the apparatus (e.g., the pivot for the trigger 918 is disposed approximately at one end, the pivot for the lever 979 is located approximately at the other end). Note that in this embodiment, the trigger 918 and the lever each pivot in about the same direction, e.g., downward. Of course, other embodiments may employ other types of actuators and/or arrangements.

Figure 41A:
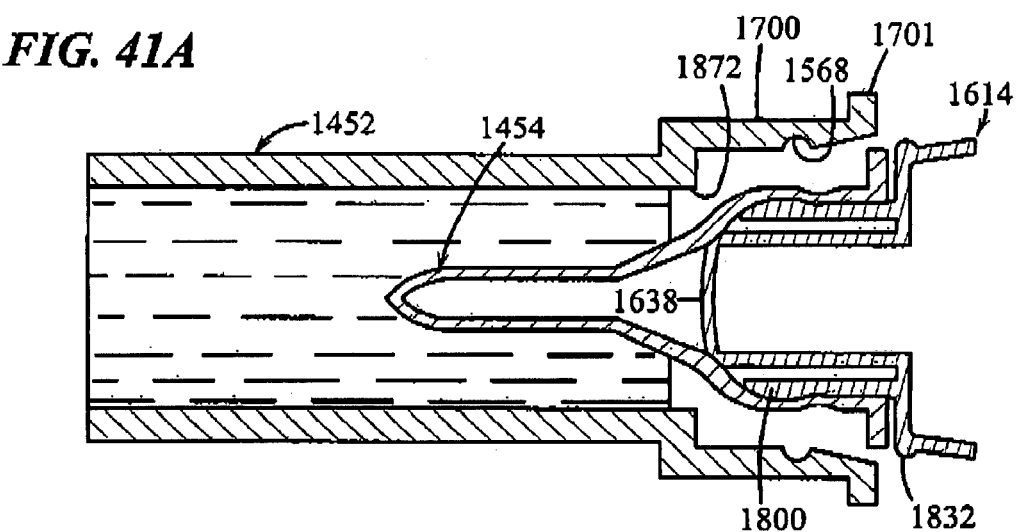
FIG. 41A is a side elevational view, partly in section, showing another embodiment of the rigid vial and bladder, wherein the vial is in a filled and un-capped condition.
Figure 41B:
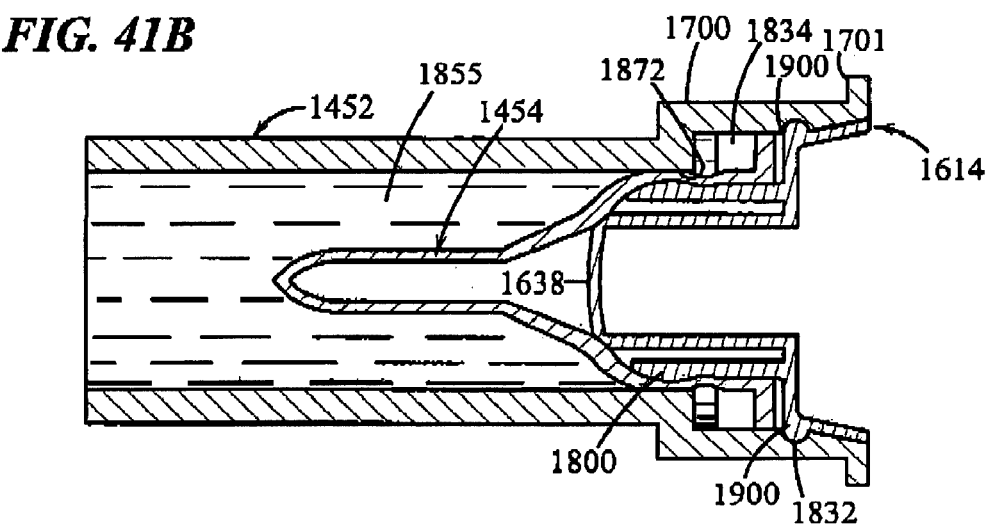
FIG. 41B is a side elevational view, partly in section, showing the rigid vial and bladder of FIG. 41A, wherein the vial is in a capped condition.
Figure 42:
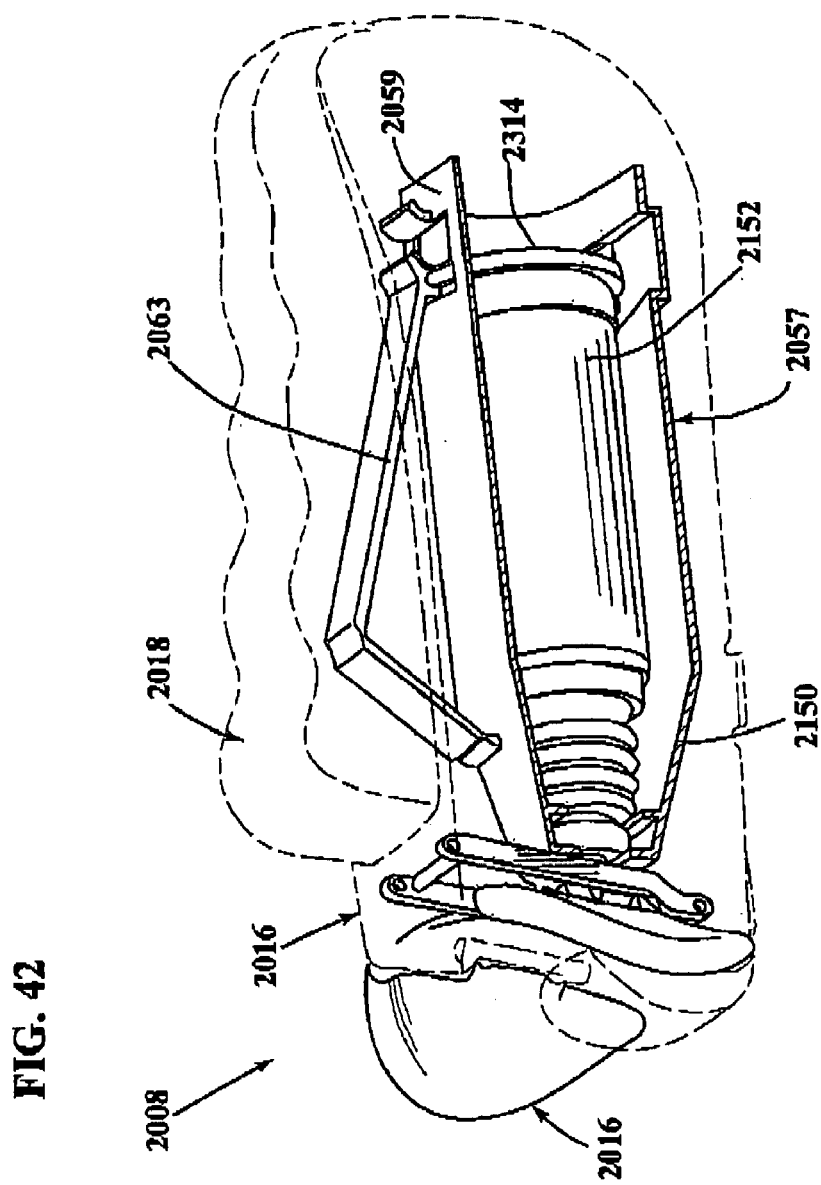
FIG. 42 is a front-top perspective view, partially in phantom, of an ocular treatment apparatus according to another embodiment of the present invention.
Figure 43:
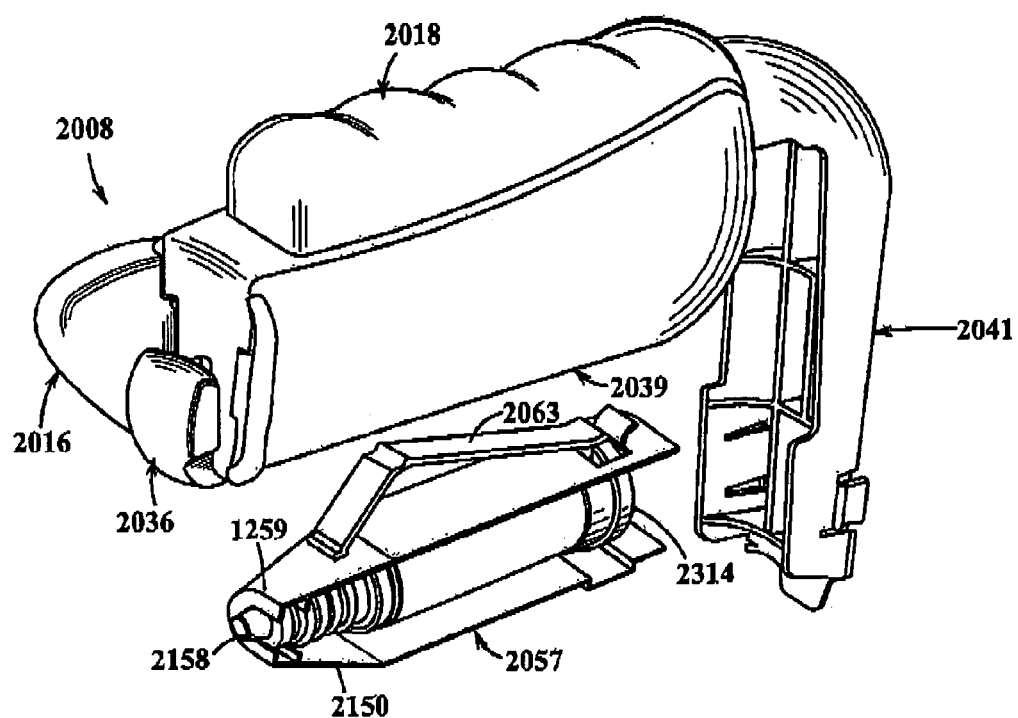
FIG. 43 is a partially exploded view, in perspective, of the ocular treatment apparatus of FIG. 41.
Figure 44:
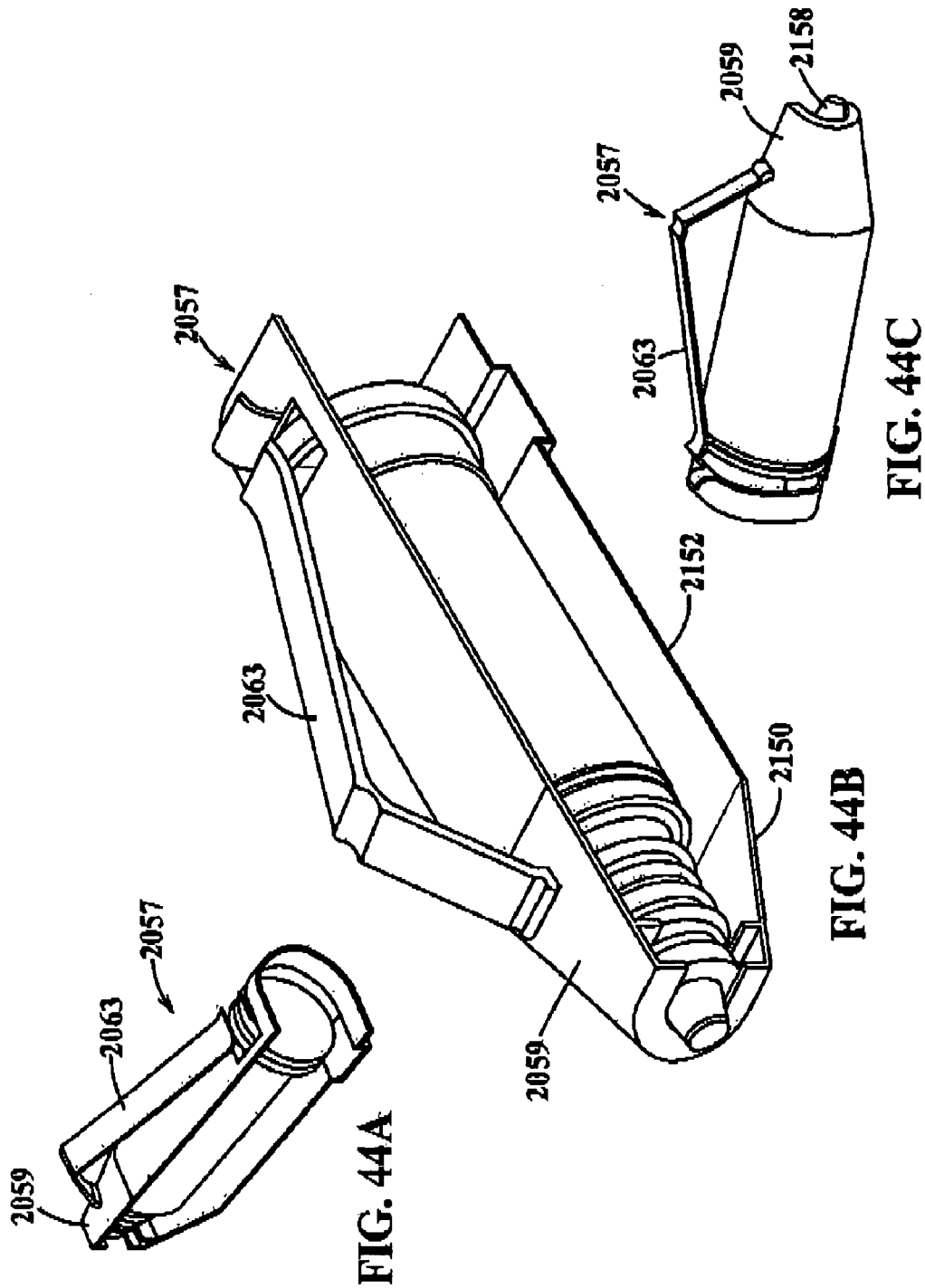
FIGS. 44A-44C are perspective views of the cartridge of FIG. 41.
Figure 45:
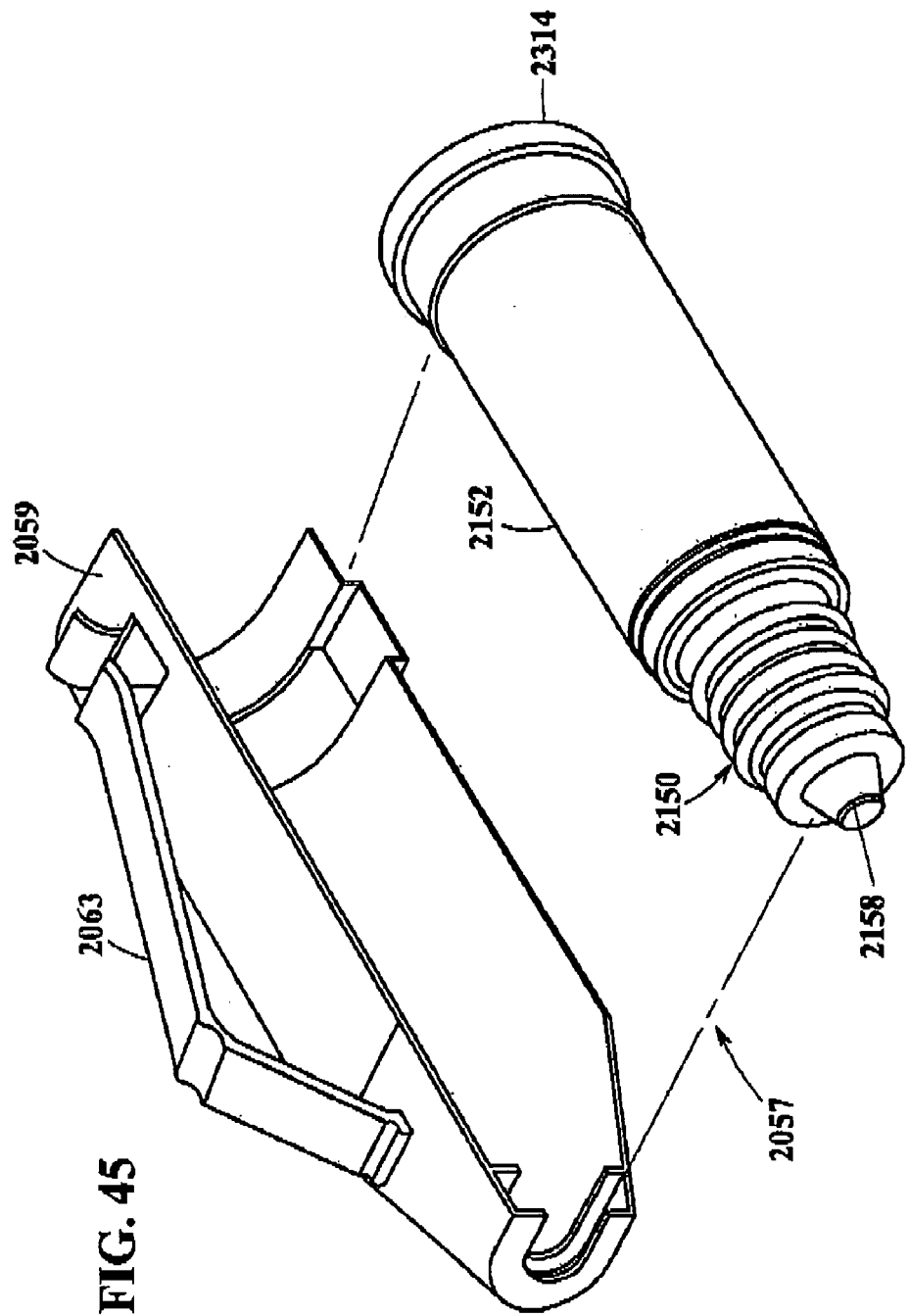
FIG. 45 is an exploded view, in perspective, of the cartridge of FIG. 41.

FIG. 41A is a side elevational view, partly in section, showing another embodiment of a rigid vial 1452, a bladder 1454, and a rear plug 1614, shown in a filled and un-capped condition. FIG. 41B is a side elevational view, partly in section, showing the rigid vial, and bladder of FIG. 41A in a capped condition. In this embodiment of the rigid vial 1452, bladder 1454, and rear plug 1614, there is no need for vacuum capping. The rigid vial 1452, bladder 1454, and rear plug 1614 are similar to the rigid vial 1052, flexible bladder 1054, and rear plug 1214 described above with respect to FIGS. 38. Hereafter reference numerals preceded by the numerals "14" instead of the numerals "10" indicate similar elements. Similarly, reference numerals preceded by the numerals "15" instead of the numerals "11" indicate similar elements, reference numerals preceded by the numerals "16" instead of the numerals "12" indicate similar elements, and reference numerals preceded by the numerals "17" instead of the numerals "13" indicate similar elements.

Referring to FIG. 41B, the rigid vial 1052 includes a peripheral groove 1568, an increased diameter portion 1700, an annular ridge portion 1701, a main fluid chamber 1855, and an annular ridge 1872 at an anterior portion of the increased diameter portion 1700. The main fluid chamber 1855 is similar to the main fluid chamber 55 (FIG. 9). The rear plug 1614 has inwardly projecting legs 1638, an annular rib 1800, and an annular surface 1832. The projection legs 1638 are similar to legs 1238 (FIG. 38) for controlling the collapse of the bladder 1454 into a predetermined collapsed shape. The annular rib 1800 forces the bladder 1454 into sealing contact against an anterior portion of the increased diameter portion 1700 of the vial 1452, to thereby seal the main fluid chamber 1855. The annular surface 1832, which is similar to the annular surface 532 (FIG. 19), forces a posterior portion 1900 of the bladder 1454 into sealing contact with the rigid vial 1452, to thereby define, in cooperation with the bladder 1454 and the increased diameter portion 1700 of the rigid vial 1452, an annular chamber 1834. As described below, the presence of the annular chamber 1834 helps avoid spillage when capping the rigid vial.

Referring to FIG. 41A, one method for filling the main fluid chamber 1855 without vacuum capping is as follows. The main chamber 1855 of the rigid vial 1452 is supplied with a medicament (or other substance) to be contained therein. The chamber is preferably overfilled, i.e., the amount of medicament supplied to the chamber 1855 is preferably greater than the amount that the chamber 1855 can hold with the bladder and plug inserted. This helps ensure that the main fluid chamber 1855 will be filled solely with medicament or other substance, upon insertion of the bladder 1454 and rear plug 1614 (i.e., no trapped air in the main fluid chamber 1855).

Referring now to FIG. 41B, the flexible bladder 1454 and rear plug 1614 assembly are moved into the rigid vial 1452 such that the bladder 1454 engages the annular ridge 1872 and the rear plug 1614 is pressed inwardly until the annular surface 1872 snaps into place within the annular groove 1568 of the vial to thereby force the posterior portion 1900 of the bladder 1454 into sealing contact with the rigid vial 1452 and form an airtight seal. By this process, the excess medicament or other substance is pushed out of the main chamber 1855 but does not spill because it is captured by the an annular chamber 1834. Consequently, there is no need to use a vacuum to capture the excess medicament. Of course, the main chamber 1855 should not be filled to the extent that excess medicament or other substance will exceed (i.e., overflow) the annular chamber 1834.

Although the cartridge 957 is shown used with a treatment apparatus having a number of features, e.g., housing 912, eye cover 916, trigger 918, eyelid depressor 936, the cartridge can also be used with treatment apparatus having only a portion of these features. For example, in some embodiments, the cartridge 957 is used in association with a treatment apparatus without a cover portion to hide the cartridge. Thus, even when mounted in the housing, the cartridge may be in plain sight at all times. In some other embodiments, for example, the cartridge may be used with a treatment apparatus that does not have an eye cover 916, a trigger 918, an eyelid depressor 936. Of course, some treatment apparatus may have more features than that of the treatment apparatus 908.

Figure 46:
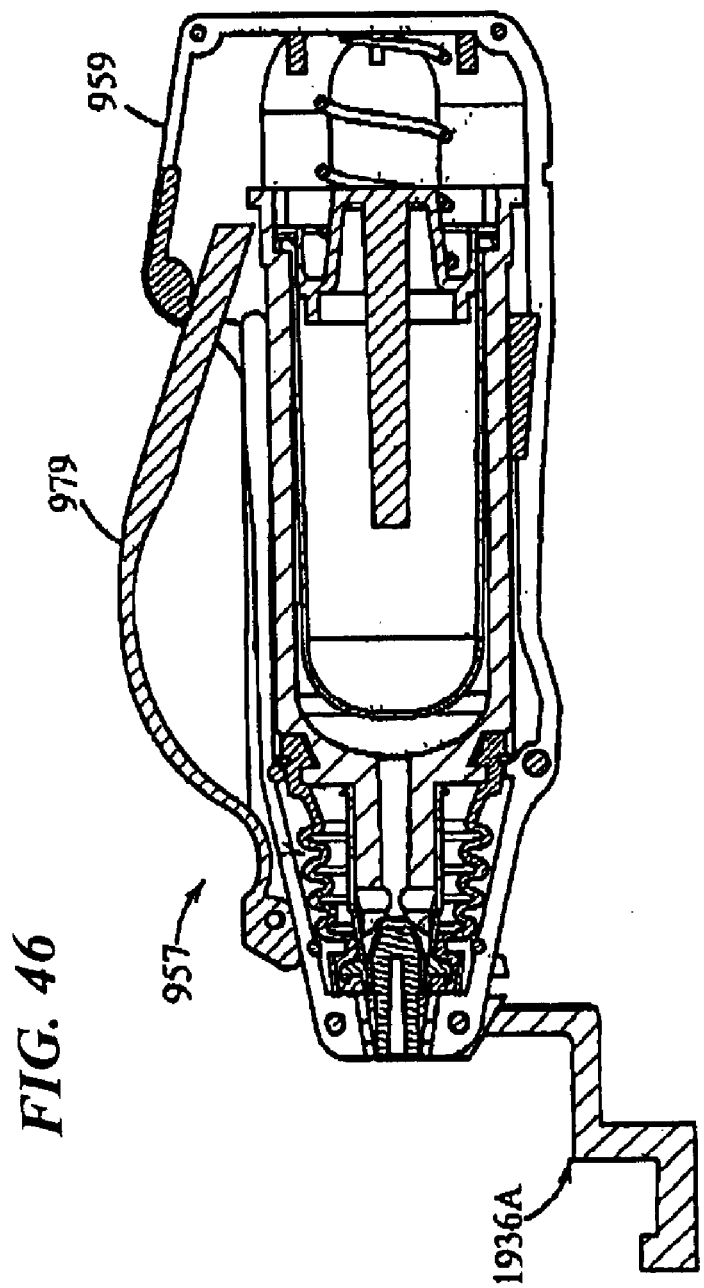
FIG. 46 is a cross sectional view of the cartridge of FIG. 41 with one embodiment of an eyelid depressor.
Figure 47A:
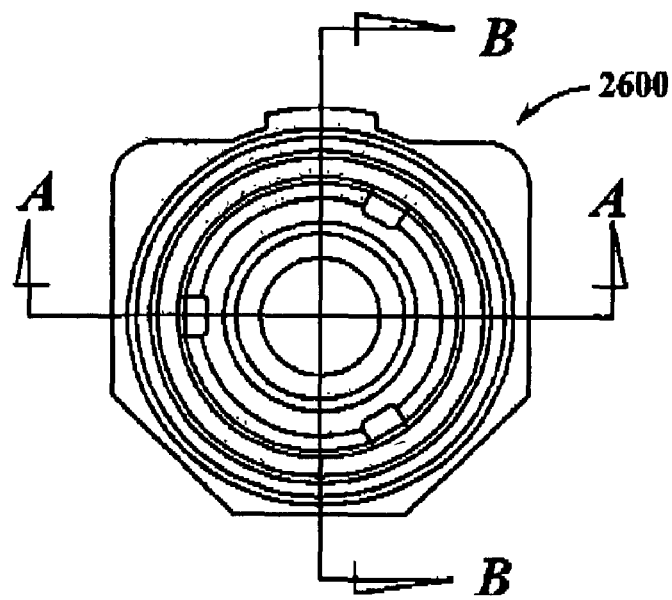
Figure 47B:
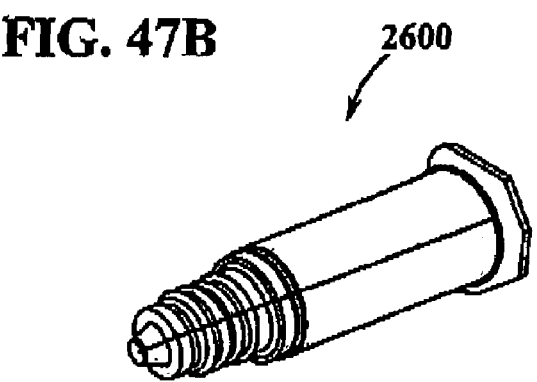
Figure 48:
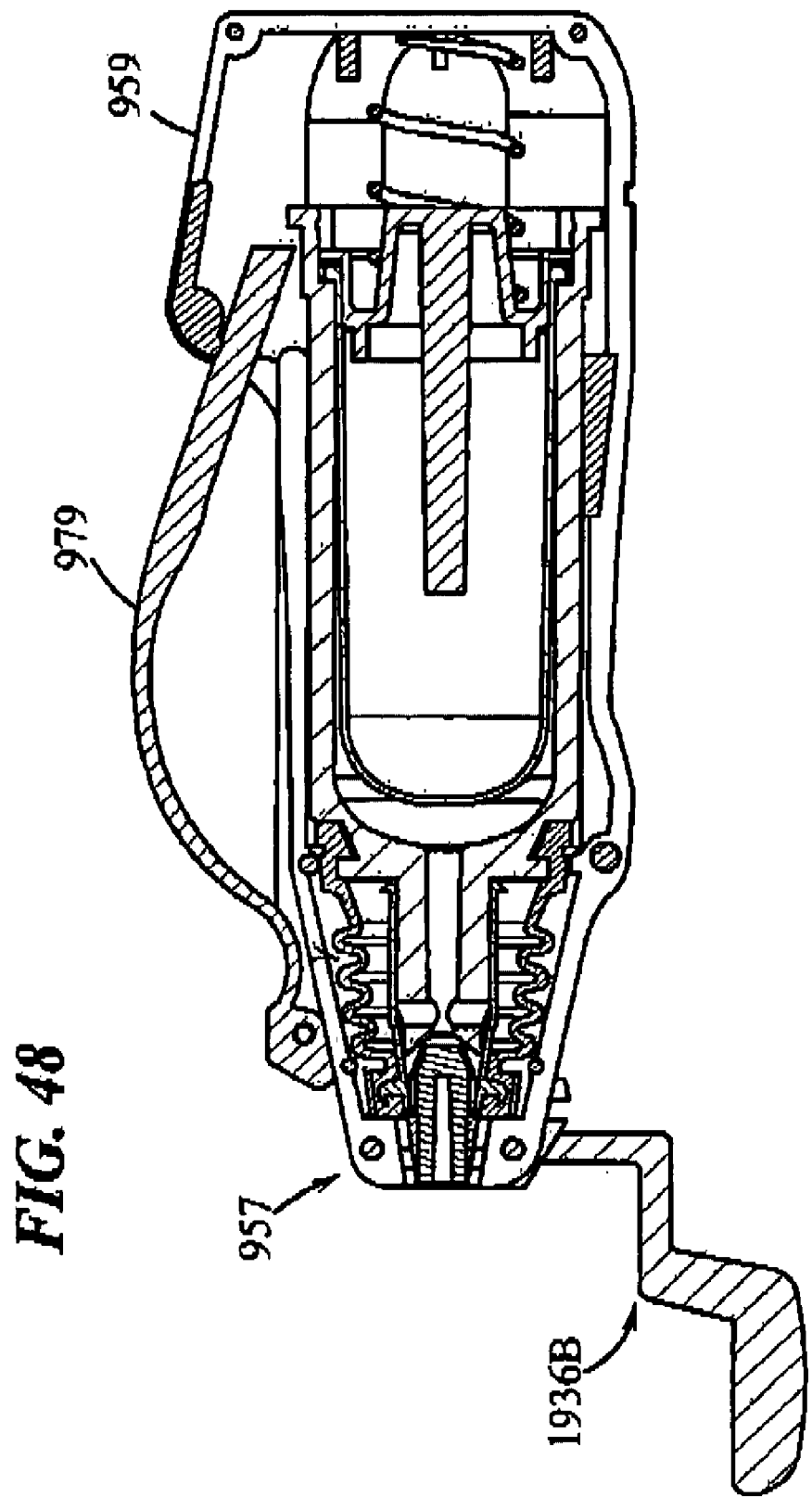
FIG. 48 is a cross sectional view of the cartridge of FIG. 41 with another embodiment of an eyelid depressor.

Moreover, although the cartridge 957 is shown used within the treatment apparatus 908, it should be recognized that the cartridge 957 could be used by itself, i.e., without the rest of the apparatus 908. For example, the user could depress the lever of the cartridge with his or her hand. Furthermore, if desired, an eyelid depressor and/or other feature(s) may be combined with the cartridge 957 in order to further assist the user in dispensing medicament. The eyelid depressor need not be trigger actuated as with the eyelid depressor 936. An example of a cartridge 957 with one embodiment of an eyelid depressor 1952 is shown in FIG. 46. A cartridge 957 with another embodiment of an eyelid depressor 1954 is shown in FIG. 48. As may be recognized by those of ordinary skill in the pertinent art based on the teachings herein, the eyelid depressors may take any of numerous different shapes and configurations that are currently known, or later become known for performing the functions of any of the various eyelid depressors as indicated herein.

Furthermore, it should be understood that the cartridge 957 is not limited to the specific embodiments of the cartridge 957 shown above. For example, in some embodiments, the cartridge may not employ an integral pump and vial. Moreover, some embodiments may employ a different shape casing, a different actuator, and/or a different storage and/or delivery system.

In addition, it should be understood that the dispensers and cartridges disclosed herein are not limited to eye treatment or even medical applications.

FIGS. 42-45 show an ocular treatment apparatus 2008 according to another aspect of the present invention. The treatment apparatus 2008 is similar to the treatment apparatus 908 (FIGS. 34-40). Except where otherwise noted, reference numerals preceded by the numerals "20" instead of the numeral "9" indicate similar elements, reference numerals preceded by the numerals "21" instead of the numerals "10" indicate similar elements, and reference numerals preceded by the numerals "23" instead of the numerals "12" indicate similar elements, except where otherwise noted.

For example, the treatment apparatus 2008 includes a housing 2012, an eye cover 2016, a trigger 2018, and an eyelid depressor 2036, which are similar to the housing 912, eye cover 916, trigger 918, and eyelid depressor 936 of the treatment apparatus 908 (FIGS. 34-40).

The primary differences between the treatment apparatus 2008 and the treatment apparatus 9008 relate to differences between the cartridge 2057 and the cartridge 957 (FIGS. 35-40). In particular, (i) the cartridge 2057 has an actuator 2063 that includes two living hinges instead of the curved lever 957, (ii) the cartridge 2057 is open, instead of substantially sealed, so as to permit access to the components within the cartridge 2057, (iii) the cartridge 2057 does not employ a spring disposed between the rear plug 2314 and the casing 2059, (iv) the cartridge 2057 does not have flattened portions corresponding to those of the cartridge 957 (see flattened portions 971 (FIG. 37)), and (v) the nozzle 2158 extends completely through the casing 2059.

Although the lever and casing are shown above as being separate pieces, this is not required. For example, in some embodiments, the lever and casing are formed into a single integral component.

FIGS. 47A-47D are views of another embodiment of a fluid storage and delivery system 2600 that may be used in the cartridge. This embodiment includes a pump assembly 2650, a rigid vial 2652, a flexible bladder 2654, a piston 2656, a nozzle 2658, a slide 2660, a pump cover 2662, a nozzle cover 2750, a cavity 2780, a rear plug 2814, and a valve 2834 (see FIG. 47D).

It should be recognized that although the cartridge 957 is a substantially sealed unit, the present invention is not limited to cartridges that are substantially sealed units. For example, some embodiments may employ a cartridge that is self contained (or at least substantially self contained) but not substantially sealed. Other embodiments may employ a cartridge that is not even self contained.

Although the second portion 941 of the housing 912 has prongs 953 adapted to engage the first portion 939 to releasably lock the first portion 939 to the second portion 941, this is not meant to preclude the use of other types of engaging structures to lock the first portion to the second portion.

As stated above, the cartridge could be used by itself, i.e., without the rest of the apparatus 908. In addition, the cartridges and/or dispensers disclosed herein are not limited to eye treatment or even medical applications.

Figure 49:
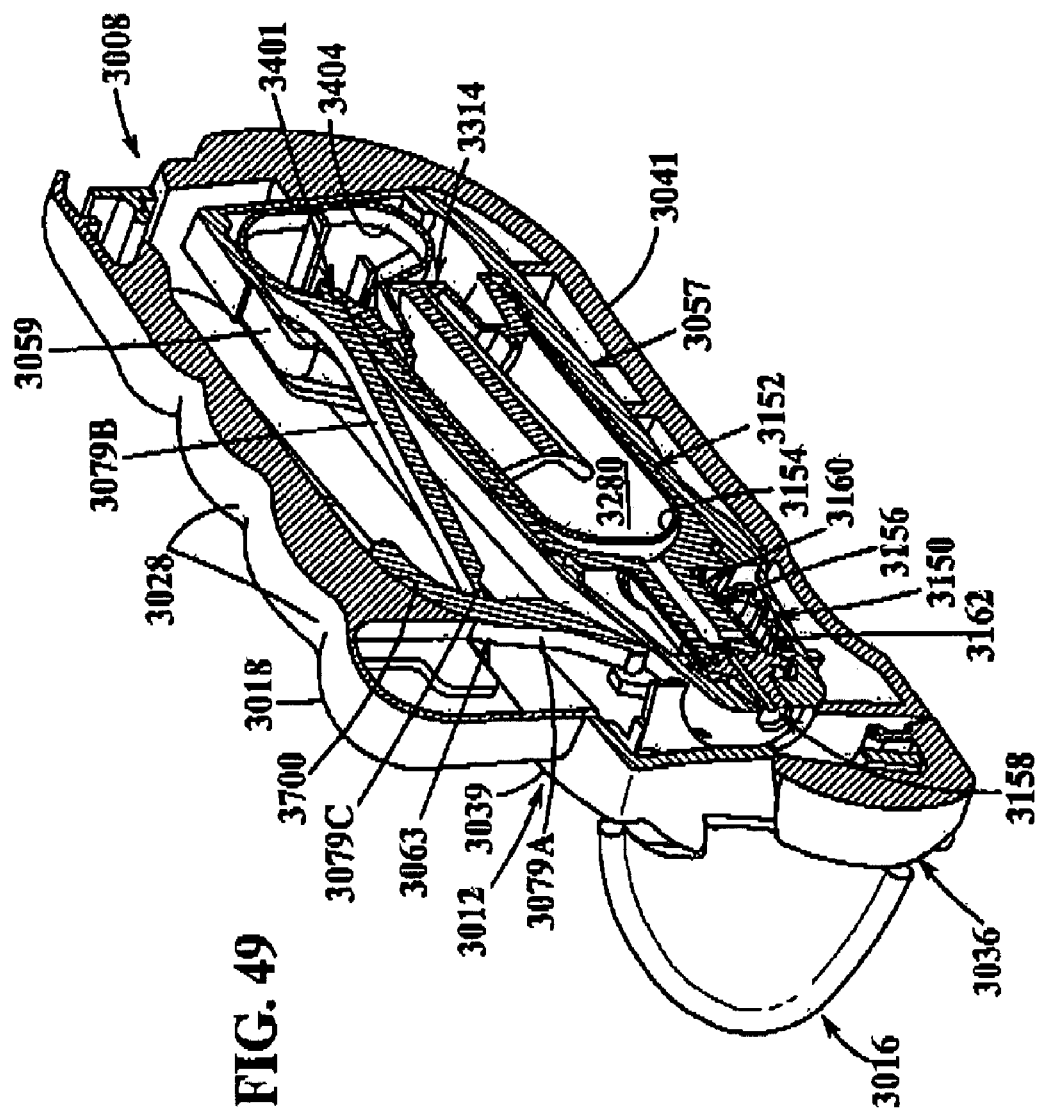
FIG. 49 is a partially broken away, perspective view of an ocular treatment apparatus according to another aspect of the present invention.
Figure 50A:
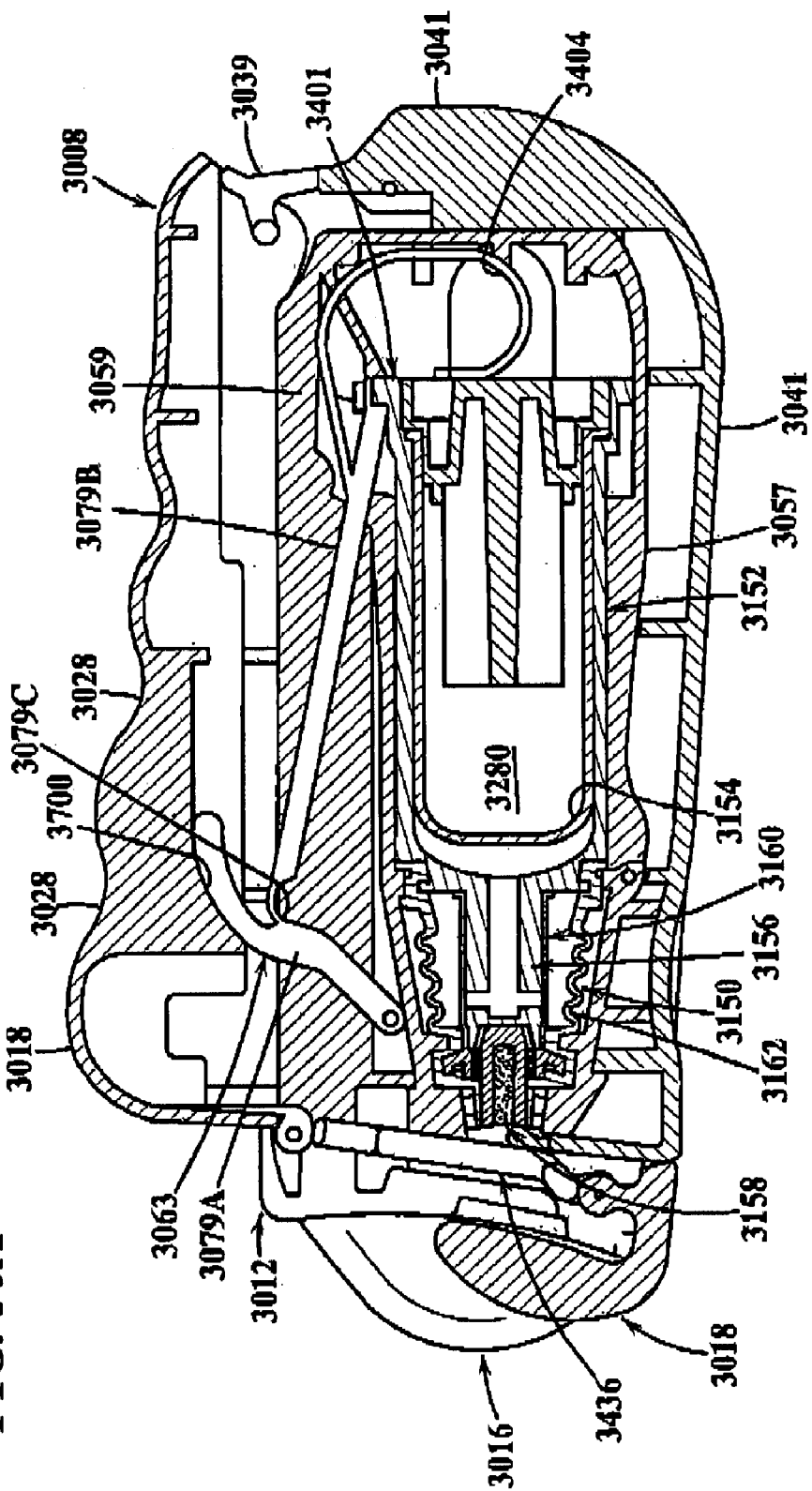
FIGS. 50A-50D are sequential side elevational views, partly in section, showing the operation of the ocular treatment apparatus of FIG. 49 as progressively greater force is applied to the trigger.
Figure 50B:
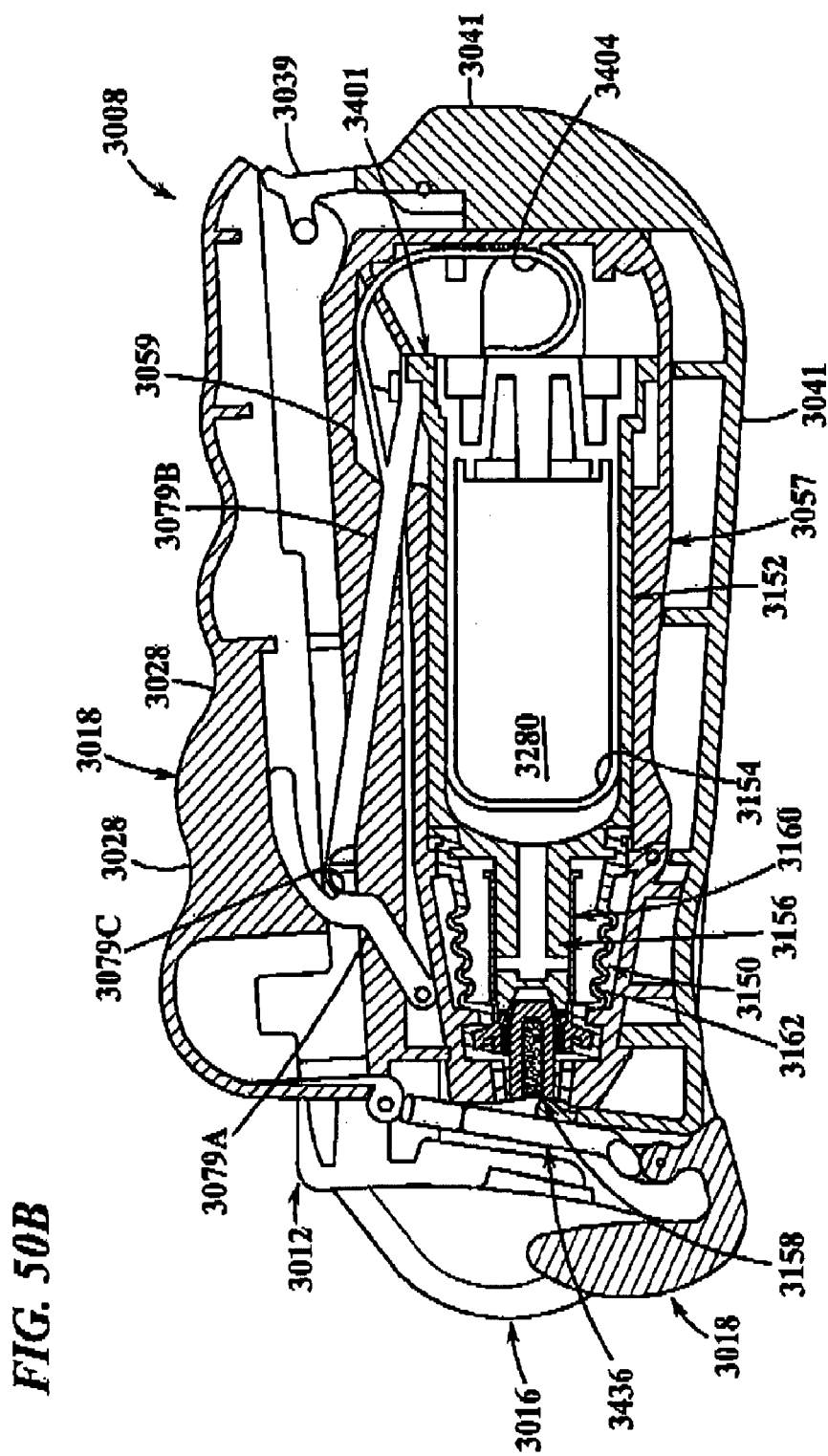
Figure 50C:
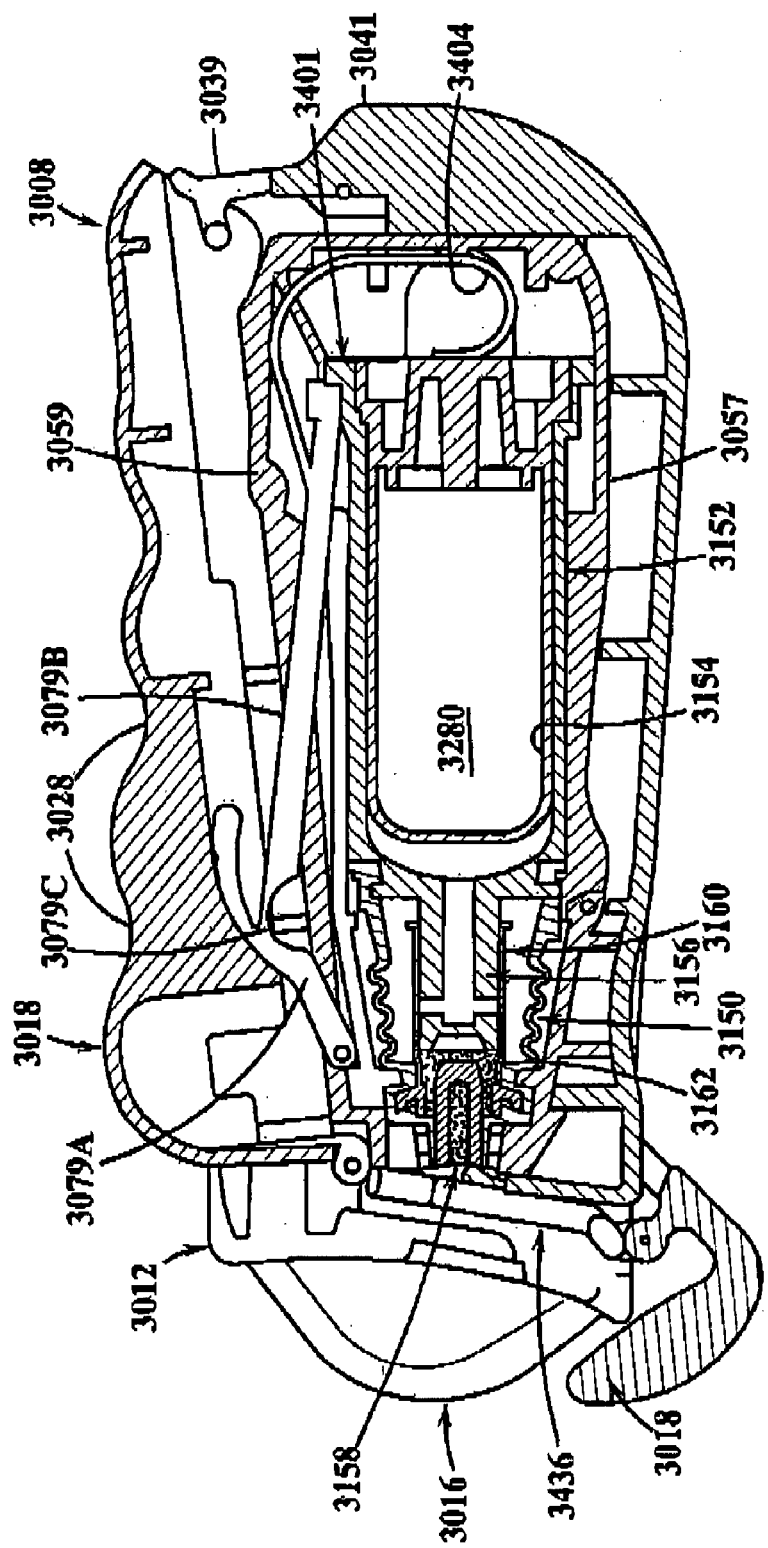
Figure 50D:
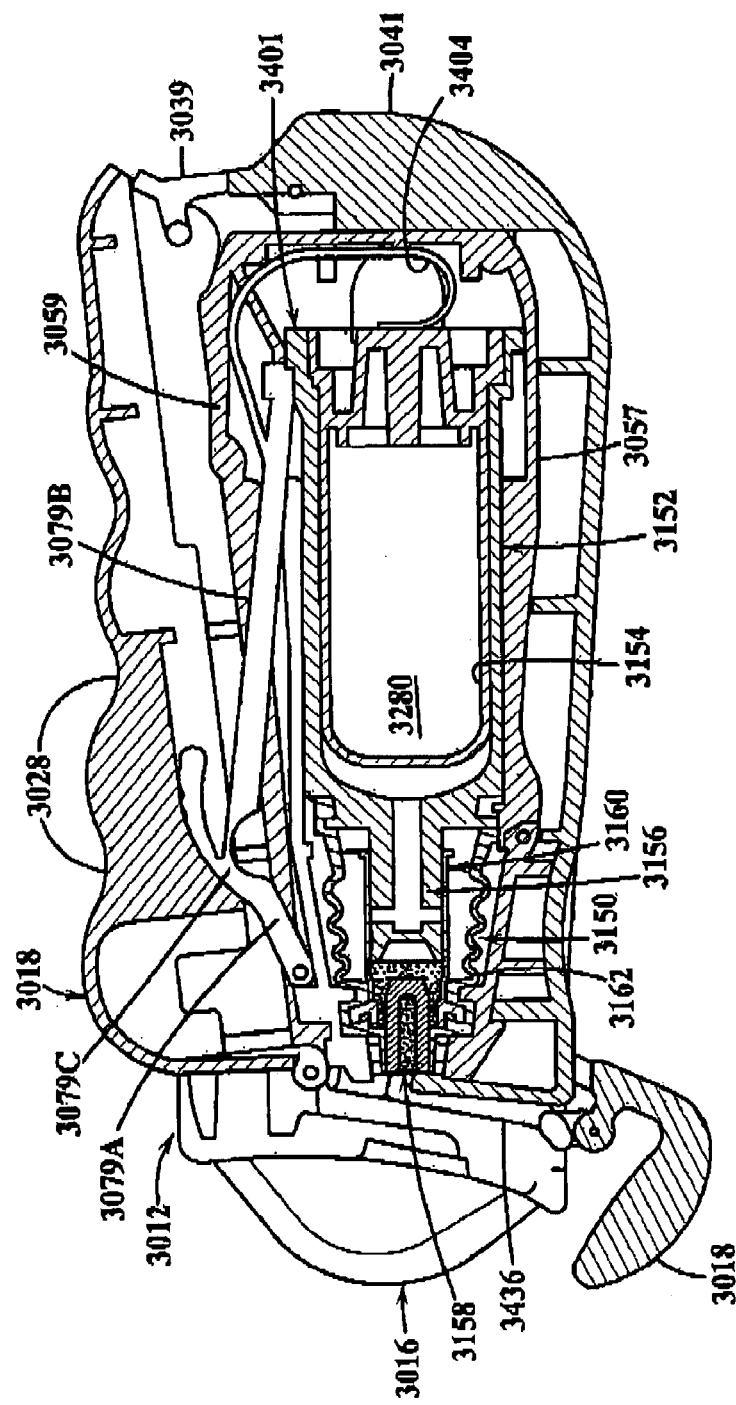
Figure 50E:
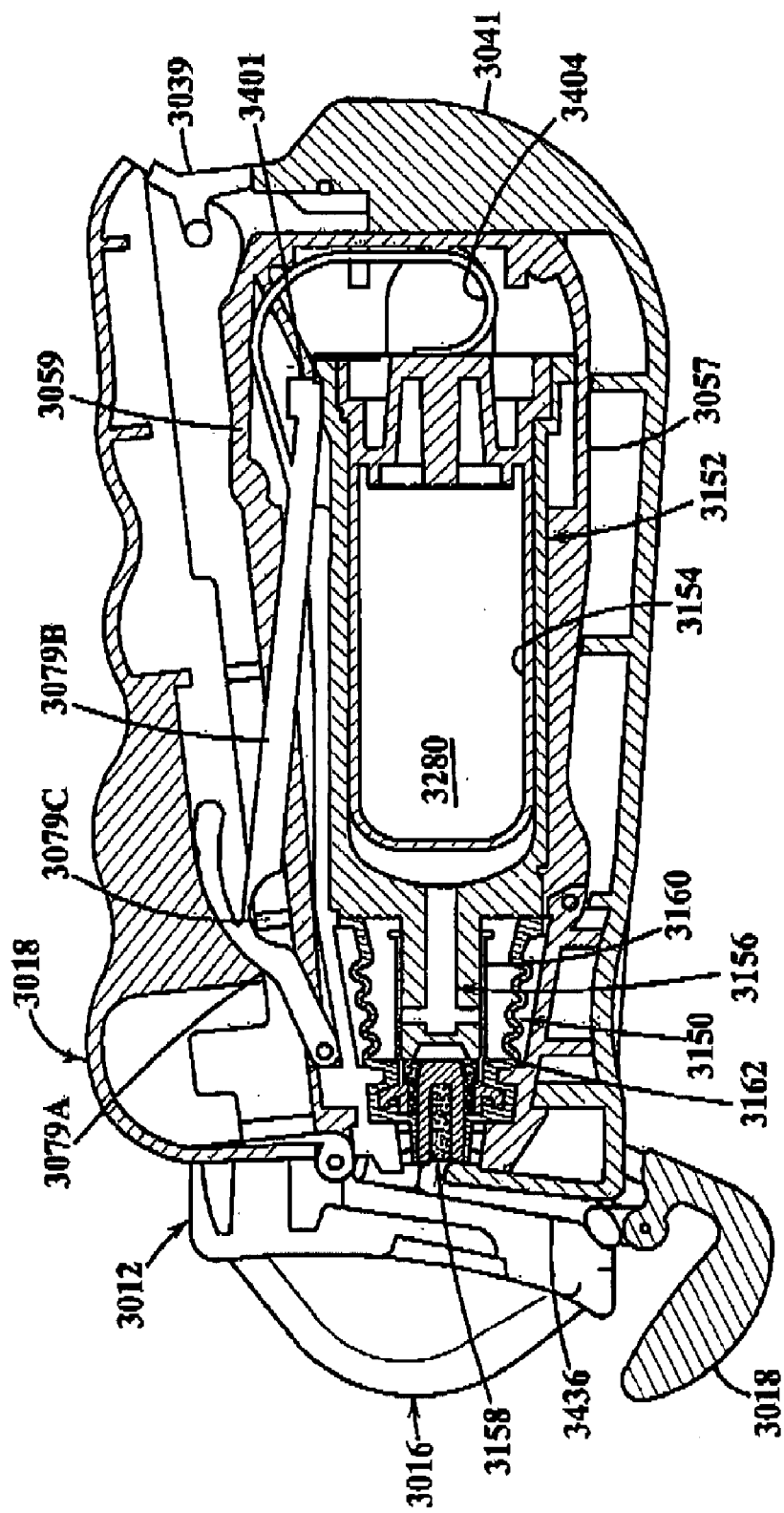
FIGS. 50E-50H are sequential side elevational views, partly in section, showing the operation of the ocular treatment apparatus of FIG. 49 after the trigger is fully actuated and the trigger progressively returns to its initial state.
Figure 50F:
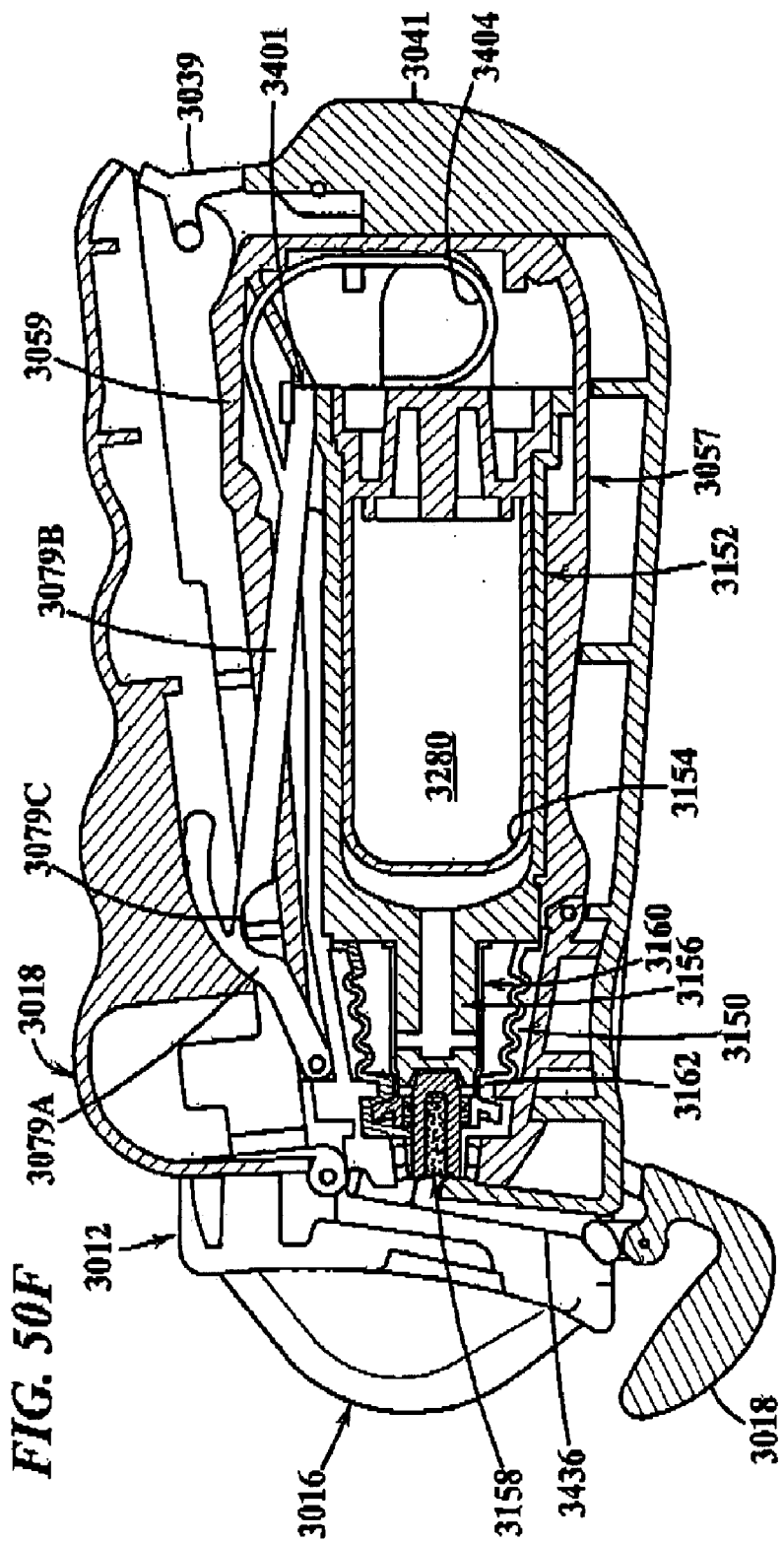
Figure 50G:
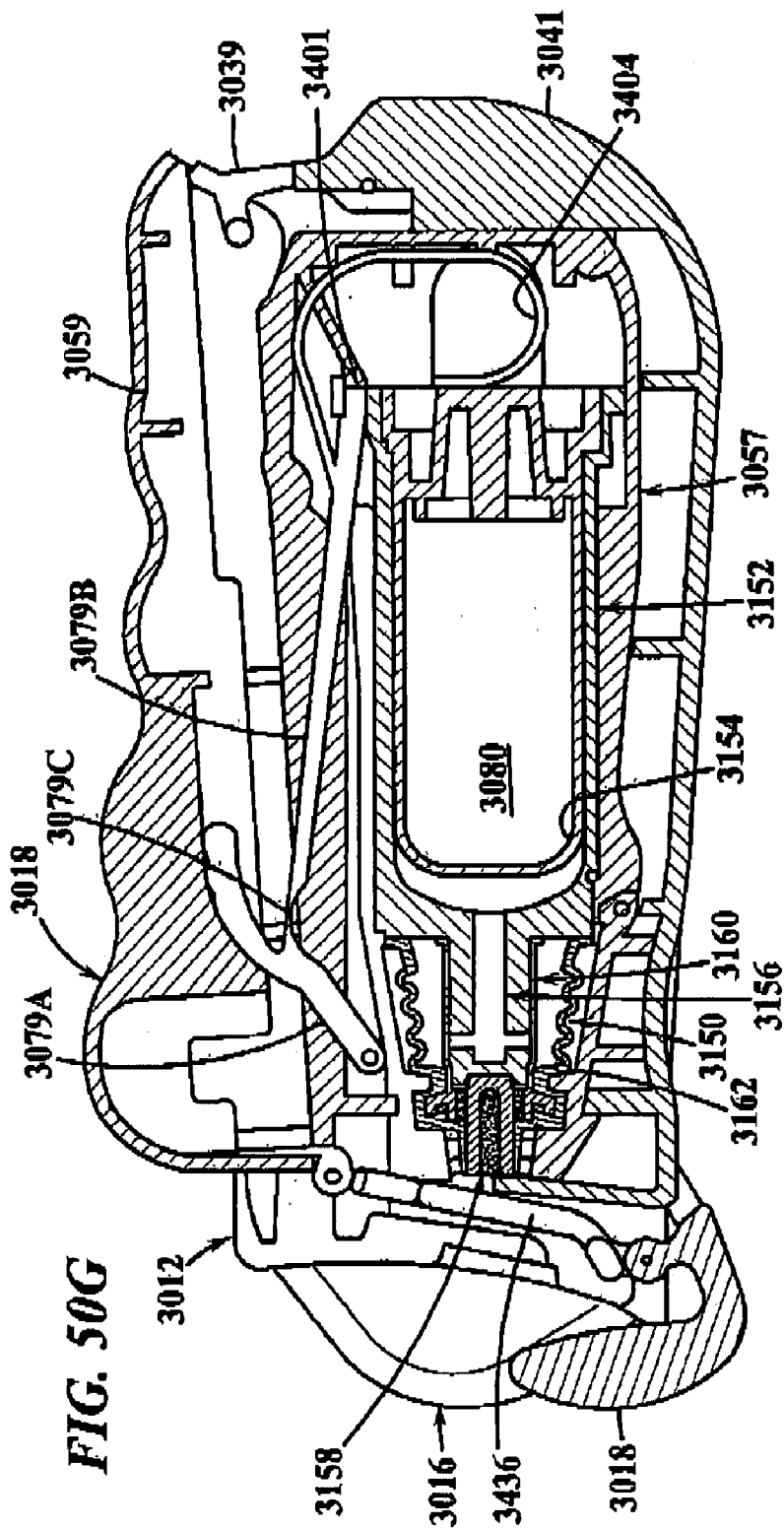
Figure 50H:
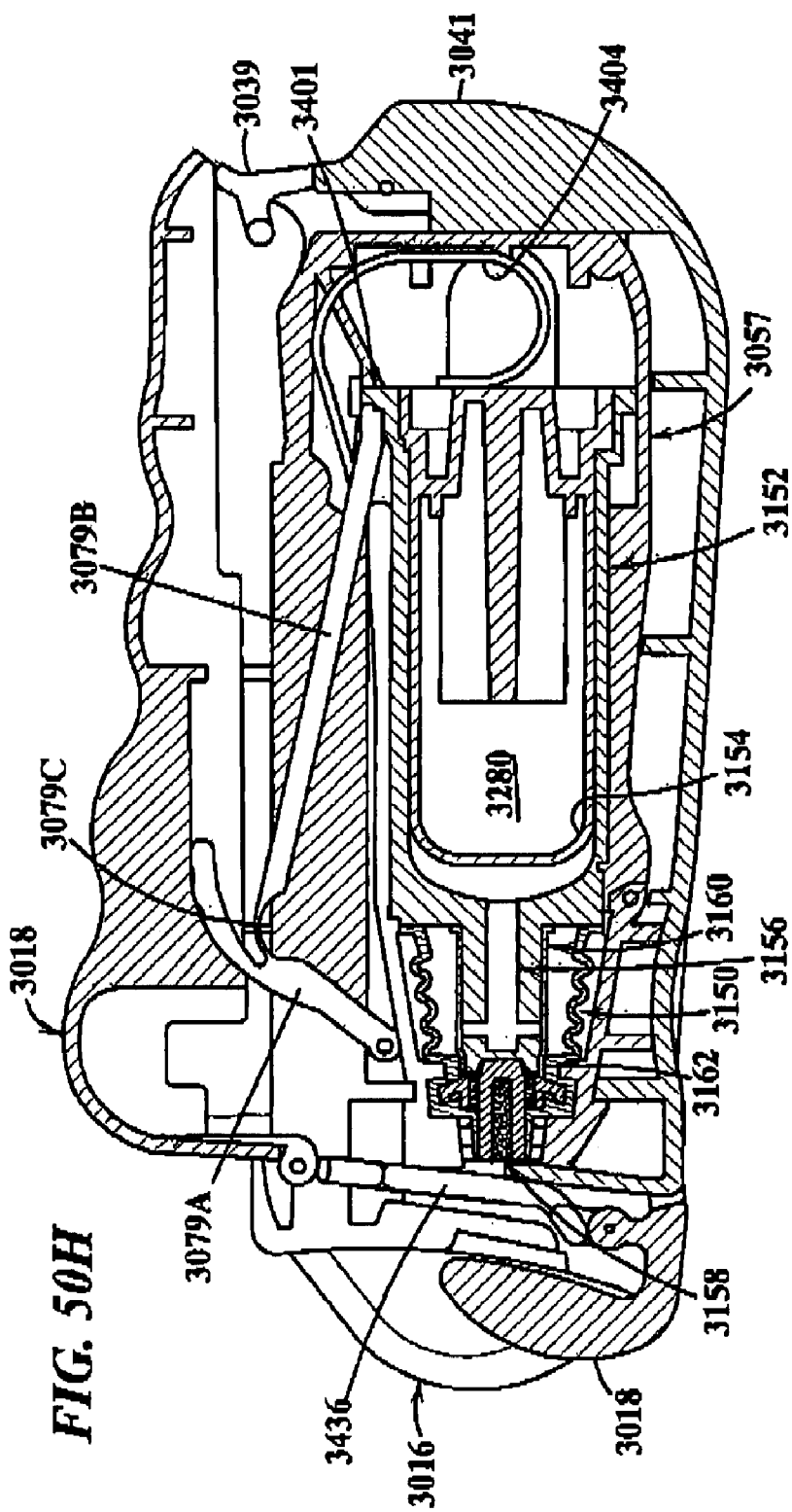

FIG. 49 is a partially broken away, perspective view of an ocular treatment apparatus 3008 according to another aspect of the present invention. The treatment apparatus 3008 is similar to the treatment apparatus 908 (FIGS. 34-40). Except where otherwise noted, reference numerals preceded by the numerals "30" instead of the numeral "9" indicate similar elements, reference numerals preceded by the numerals "31" instead of the numerals "10" indicate similar elements, reference numerals preceded by the numerals "32" instead of the numerals "11" indicate similar elements, reference numerals preceded by the numerals "33" instead of the numerals "12" indicate similar elements and reference numerals preceded by the numerals "34" instead of the numerals "13" indicate similar elements, except where otherwise noted.

For example, the treatment apparatus 3008 includes a housing 3012, an eye cover 3016, a trigger 3018, and an eyelid depressor 3036, which are similar to the housing 912, eye cover 916, trigger 918, and eyelid depressor 936 of the treatment apparatus 908 (FIGS. 34-40). The housing 3012 includes first and second portions 3039, 3041, which are similar to first and second portions 939, 941.

The treatment apparatus 3008 further includes a cartridge 3057 that includes a casing 3059, an actuator 3063, a pump assembly 3150, a rigid vial 3152, a flexible bladder 3154, a piston 3156, a nozzle 3158, a slide 3160, a pump cover 3162, a cavity 3280 and a rear plug 3314, which are similar to the a pump assembly 1050, a rigid vial 1052, a flexible bladder 1054, a piston 1056, a nozzle 1058, a slide 1060, a pump cover 1062, a nozzle cover 1150, a cavity 1180 and a rear plug 1214, described above with respect to FIGS. 34-40.

The primary differences between the treatment apparatus 3008 and the treatment apparatus 908 relate to differences between the cartridge 3057 and the cartridge 957 (FIGS. 35-40), differences between the trigger 3018 and the trigger 918, and differences between the housing 3012 and the housing 912. In particular, (i) the cartridge 3057 has an actuator 3063 which differs from the actuator 963 in that the actuator 3063 includes a lever 3079A and an arm 3079B pivotally connected thereto (e.g., at or via an elbow 3079C) in place of the lever 979 employed by the actuator 963, (ii) the cartridge 3057 has a spring 3404 (disposed between the rear plug 3314 and the casing 3059), which unlike the spring 1304 of the cartridge 957, is joined to, integrally formed with, and/or extends from, the actuator 3063 of the cartridge 3057. As will be described hereinafter, the spring 3404 provides a force that helps overcome friction and propel the medicament dosage out of the cartridge 3057 and into the eye. The trigger 3018, which is elongated and has finger grooves 3028, includes (i) a seat 3700 for the lever 3079A, the seat 3700 having a surface shaped to be complementary to the surface of the lever 3079A, and (ii) an end 3430 (pivotably connected to the housing 3012), which is slotted so as to be able to slide axially onto the pin 3432. Lastly, unlike the housing 912, the housing 3012 does not have a seat for said end 3430 of said trigger 3018.

FIGS. 50A-50D are sequential side elevational views, partly in section, showing the operation of the ocular treatment apparatus of FIG. 49 as progressively greater force is applied to the trigger. FIGS. 50E-50H are sequential side elevational views, partly in section, showing the operation of the ocular treatment apparatus of FIG. 49 after the trigger is fully actuated and the trigger progressively returns to its initial state.

Referring now to FIGS. 50A-50D, upon squeezing the trigger 3018, the eyelid depressor 3036 rotates and in turn moves the tissue adjacent to the eye to expose the ocular cul-de-sac. Rotation of the eyelid depressor 3036 is caused by the arm 3436 which thereby uncovers the nozzle 3158. Simultaneously, the trigger 3018 applies radially inward force to the lever 3079 of the cartridge 3057. This forces the lever 3079A toward the housing 3059 (note that in doing so the lever 3079A slides along the seat 3700 in the trigger 3018) and forces the elbow 3079C to begin to straighten, thereby causing the end of the arm 3079B to move in a direction toward the posterior end of the cartridge and engage the portion of the annular ridge 3401 of the vial 3152. In some embodiments, the movement of the arm causes the spring 3404 to compress. As additional radially inward force is applied, the elbow 3079C further straightens and the arm 3079B continues to move in the posterior direction, thereby driving the piston 3156 in the same direction so as to prime the pump (as described in detail above) and compress (or further compress) the spring 3404.

Referring now to FIGS. 50E-50H, with further radial force applied to the lever 3079A, the arm 3079B eventually disengages from the portion of the annular ridge 3401 and thereby releases the vial 3152 and piston 3156 from the force applied by the arm 3079B. As a result, and due to the resiliency or spring-like nature of the pump assembly 3150 as well as the spring force of the compressed spring 3404, the piston 3156 and vial 3152 move in a direction toward the anterior end of the cartridge 3057 and, in turn, force a predetermined dosage of medicament (or other substance) from the nozzle 3158.

Figure 51:
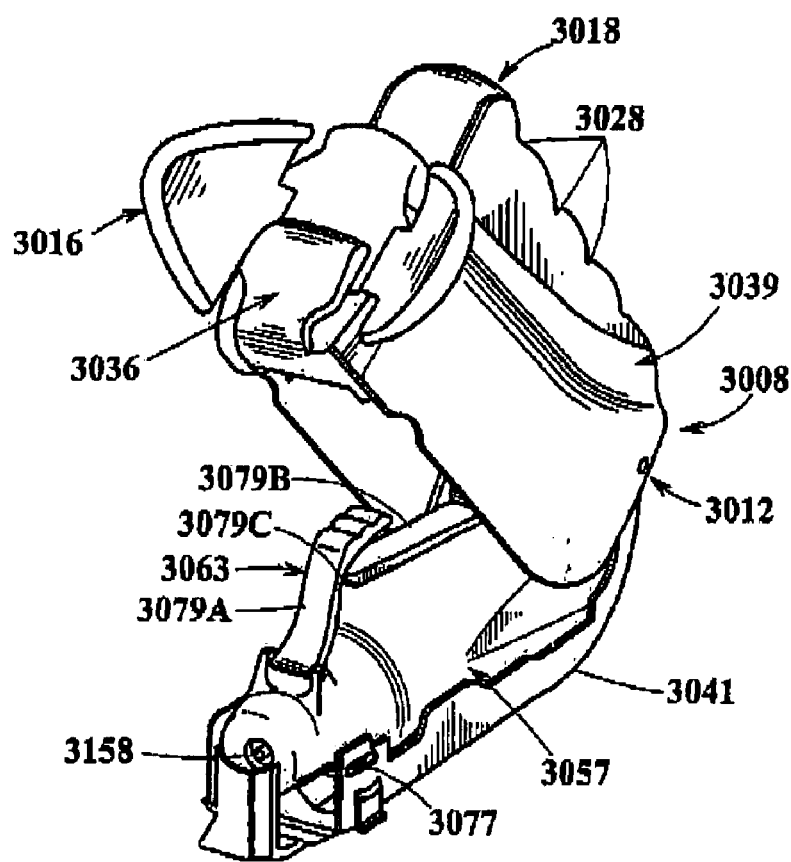
FIG. 51 is a perspective view of the ocular treatment apparatus of FIG. 49, with the housing in an open state.

FIG. 51 is a perspective view of the ocular treatment apparatus of FIG. 49, with the housing in an open state.

Figure 52:
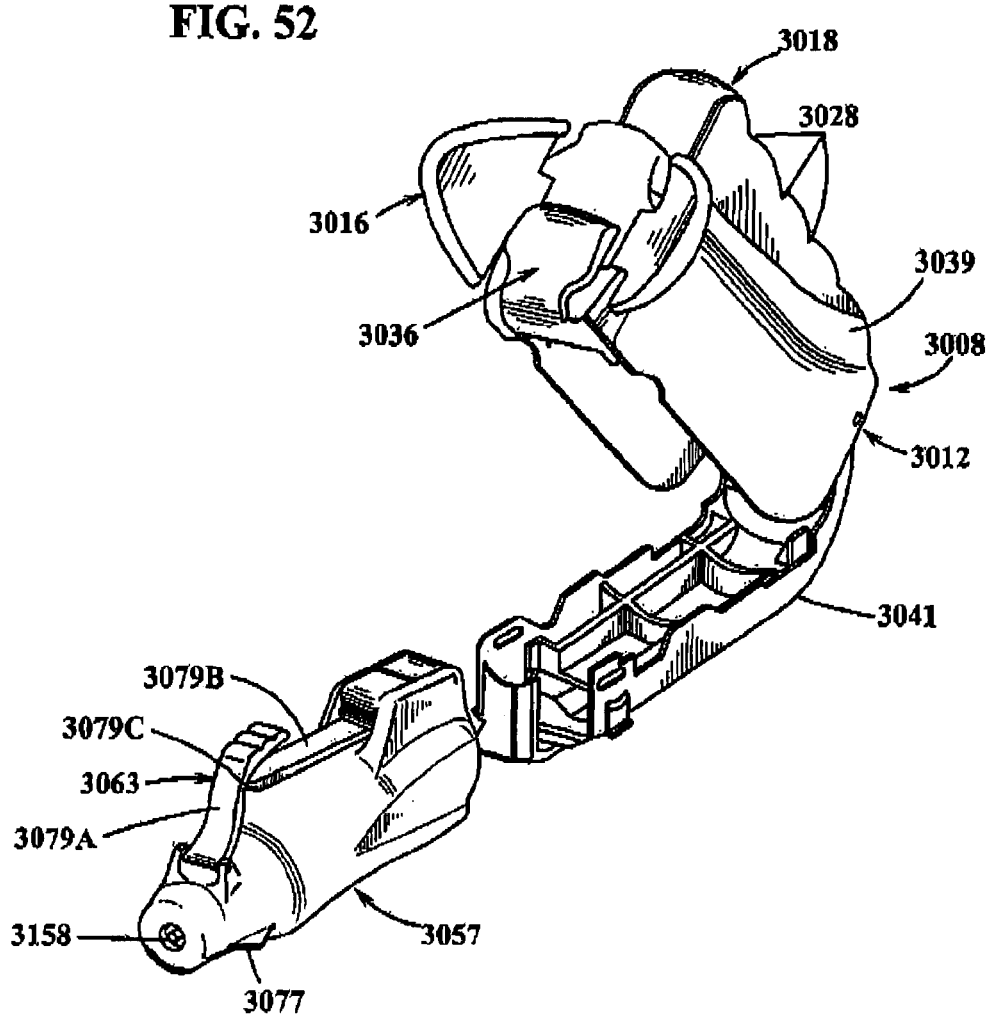
FIG. 52 is a partially exploded view, in perspective, of the ocular treatment apparatus of FIG. 49.

FIG. 52 is a partially exploded view, in perspective, of the ocular treatment apparatus of FIG. 49.

Figure 53:
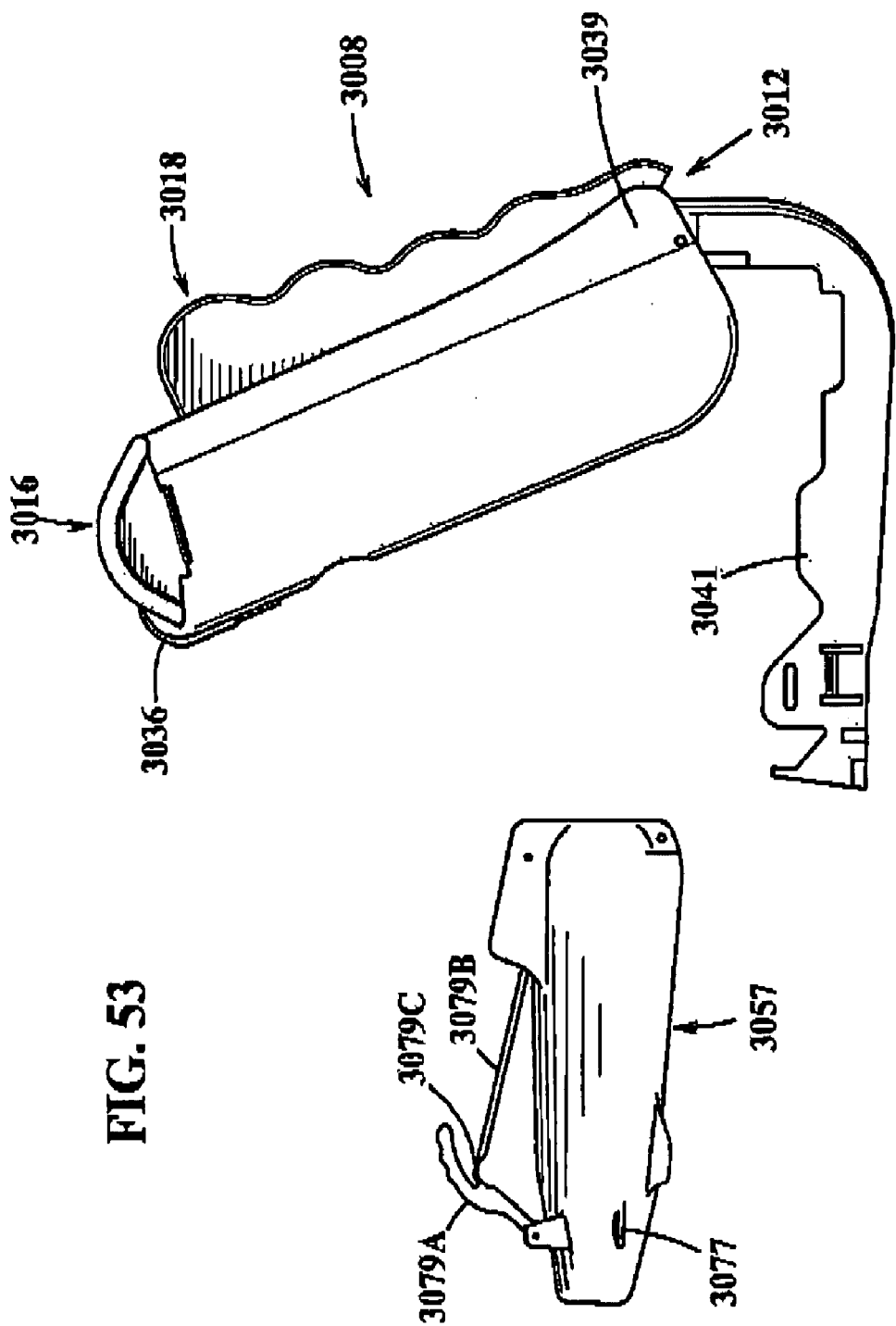
FIG. 53 is a partially exploded side elevational view, of the ocular treatment apparatus of FIG. 49.

FIG. 53 is a partially exploded side elevational view, of the ocular treatment apparatus of FIG. 49.

Although the cartridge 3057 is shown used with a treatment apparatus having a number of features, e.g., housing 3012, eye cover 3016, trigger 3018, eyelid depressor 3036, the cartridge can also be used with treatment apparatus having only a portion of these features. For example, in some embodiments, the cartridge 3057 is used in association with a treatment apparatus without a cover portion to hide the cartridge. Thus, even when mounted in the housing, the cartridge may be in plain sight at all times. In some other embodiments, for example, the cartridge may be used with a treatment apparatus that does not have an eye cover 3016, a trigger 3018, or an eyelid depressor 3036. Of course some treatment apparatus may have more features than that of the treatment apparatus 3008.

Moreover, as stated above for the cartridge 957, although the cartridge 3057 is shown used within a housing, it should be recognized that the cartridge 3057 could be used by itself, i.e., without the housing. For example, a user could use their hand to depress the actuator 3063 of the cartridge 3057. Furthermore, if desired, an eyelid depressor and/or other feature(s) may be combined with the cartridge 3057 in order to further assist the user in dispensing medicament. The eyelid depressor need not be trigger actuated as with the eyelid depressor 3036. In some embodiments, an eyelid depressor may be integrally formed into the housing 3059 of the cartridge 3057. Some other embodiments may employ an eyelid depressor that is not integral with the cartridge 3057, but rather is formed separately and thereafter attached to the cartridge.

Figure 54:
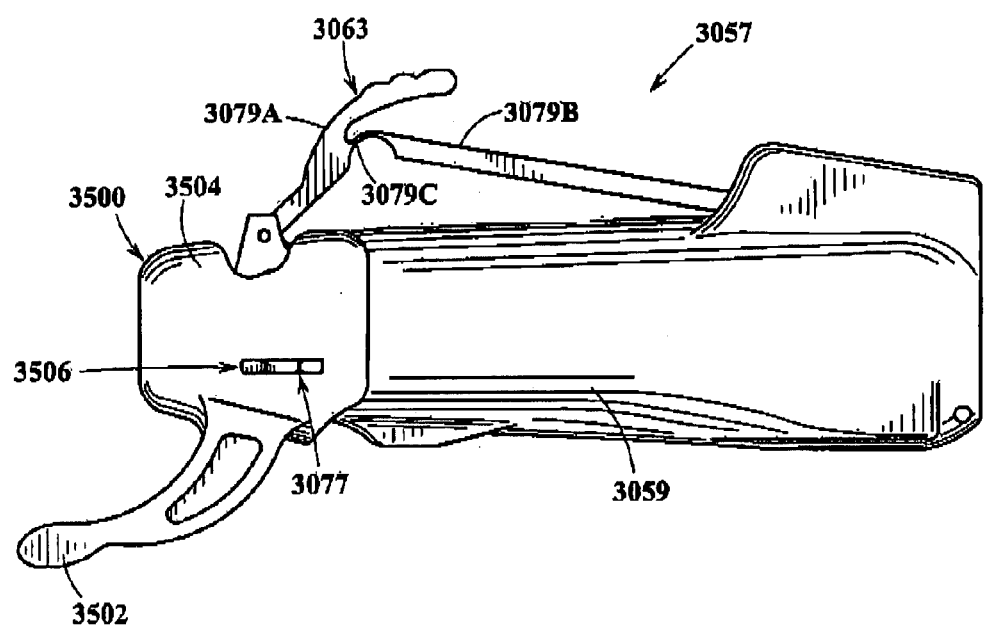
FIG. 54 is an enlarged side elevational view of the cartridge of FIG. 49 with an eyelid depressor releasably secured thereto, in accordance with another aspect of the present invention.
Figure 55:
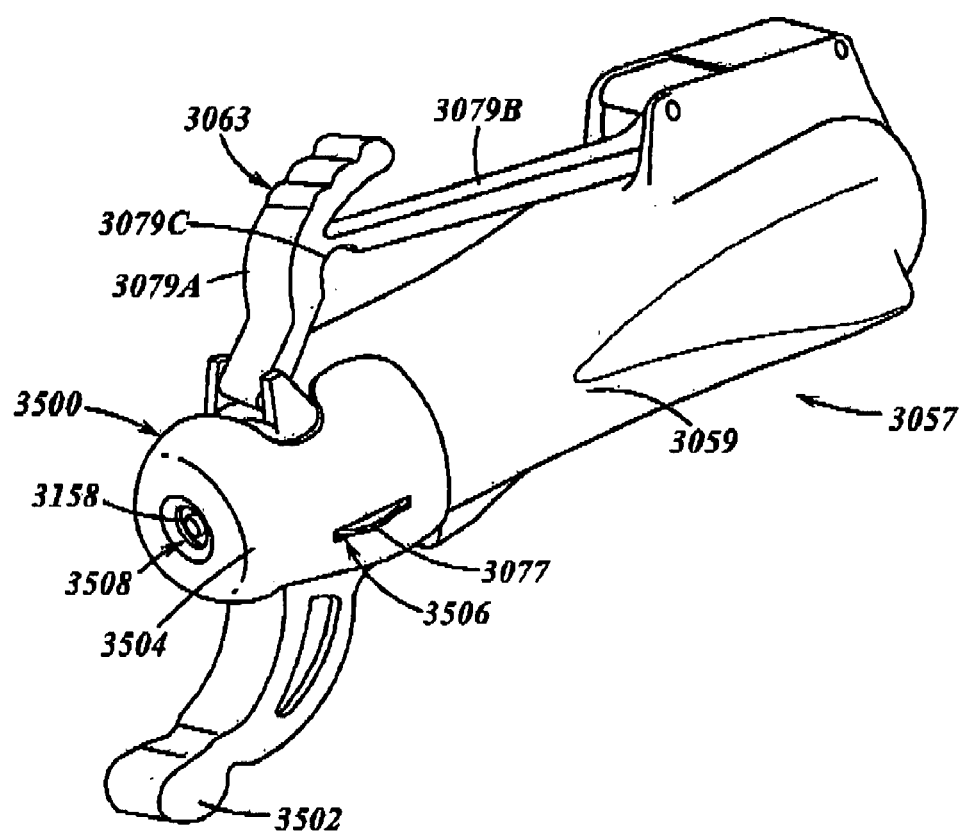
FIG. 55 is a perspective view of the cartridge and eyelid depressor of FIG. 54.

FIGS. 54-55 show one method for providing the cartridge with an eyelid depressor. This method makes use of a cap 3500 that is provided with an integral eyelid depressor 3502 and is adapted to be releasably secured to the cartridge 3057. In particular, the cap 3500 has a peripheral wall 3504 that is shaped and dimensioned to receive the end of the cartridge 3057. The peripheral wall 3504 defines openings 3506 that are adapted to receive the projections 3077, which extend from the housing 3059 of the cartridge 3057. This configuration allows the cap 3500 to be pressed or snapped onto the cartridge 3057 and/or to engage said cartridge so as to releasably secure the cap 3500 to the cartridge 3057. The peripheral wall 3504 of the cap further defines an opening 3508 in register with the nozzle 3158 so as not to block the flow of medicament delivered out of the nozzle 3158.

Figure 56:
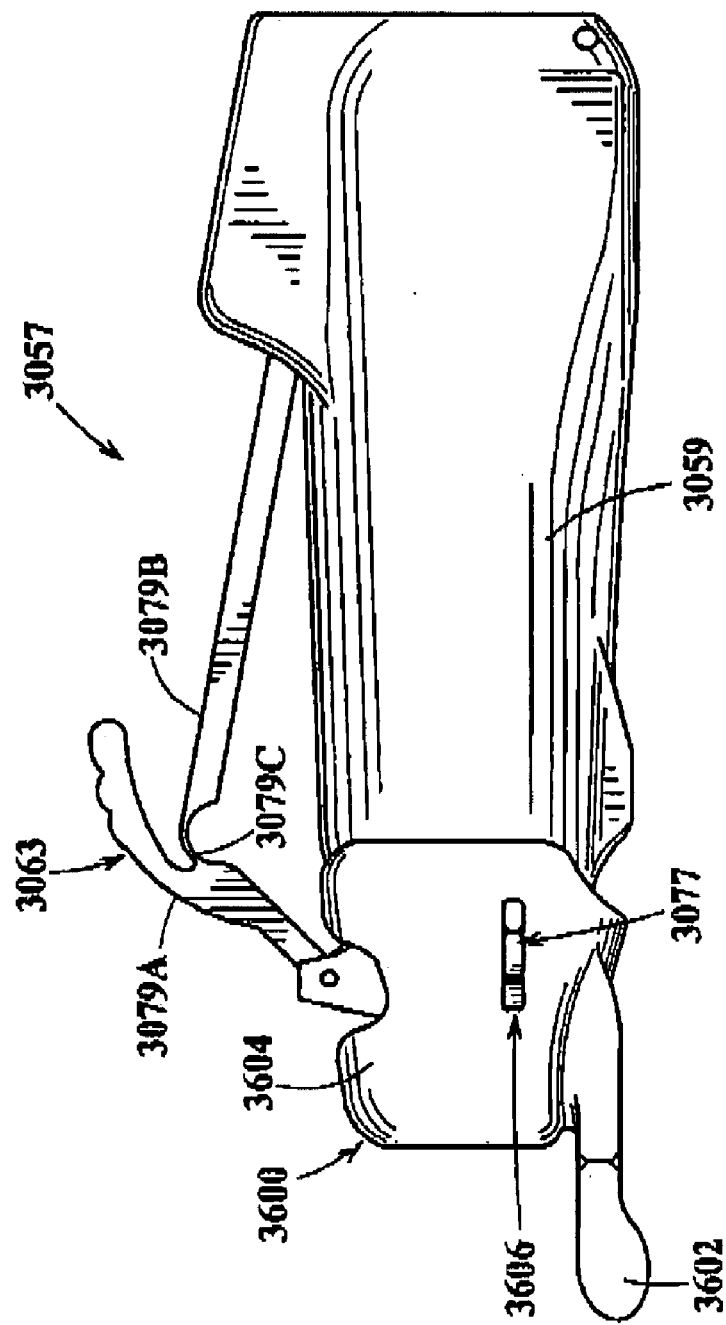
FIGS. 56-57 are side elevational views of the cartridge of FIG. 49 with an another embodiment of an eyelid depressor releasably secured thereto.
Figure 57:
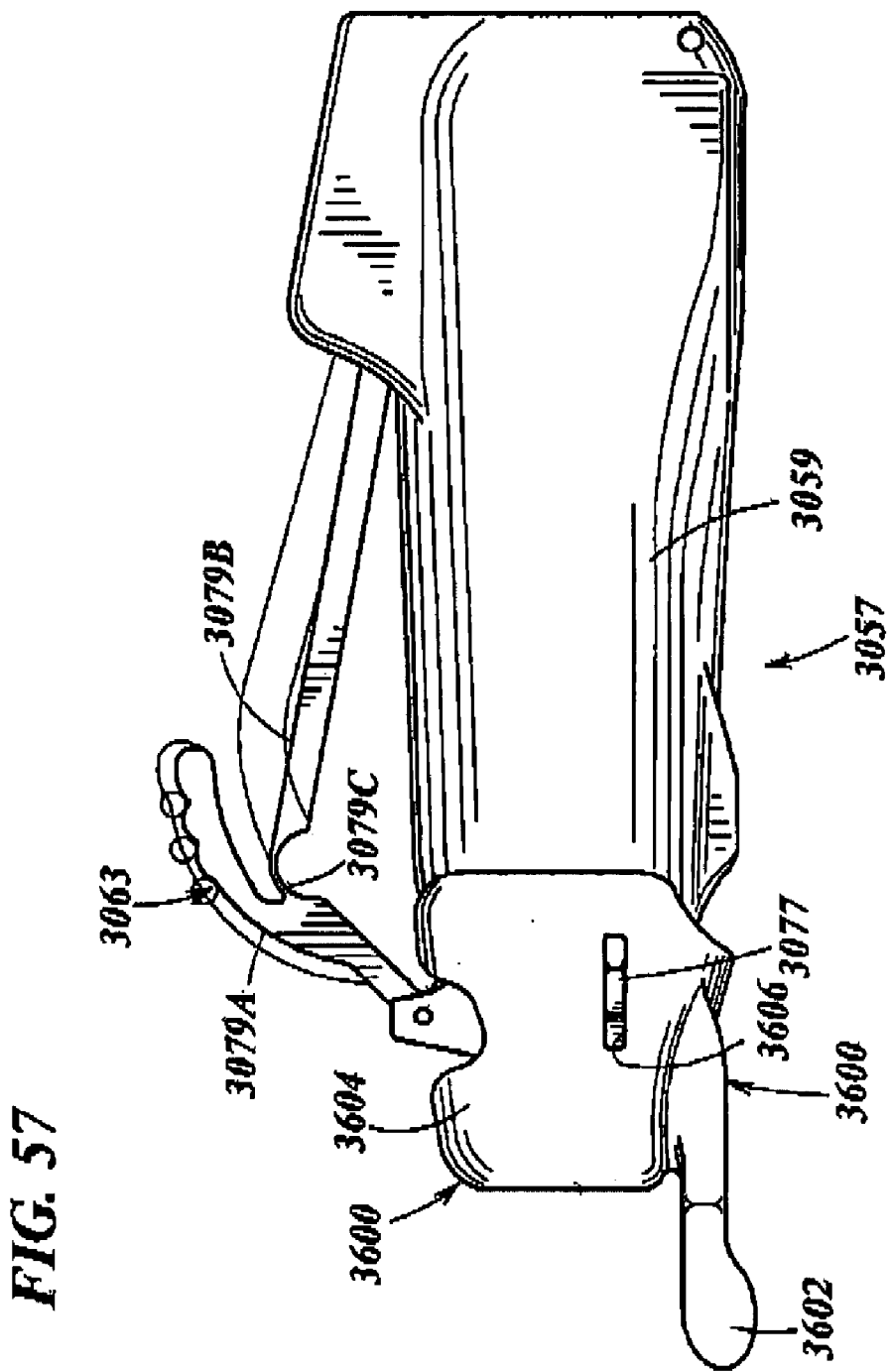
Figure 58:
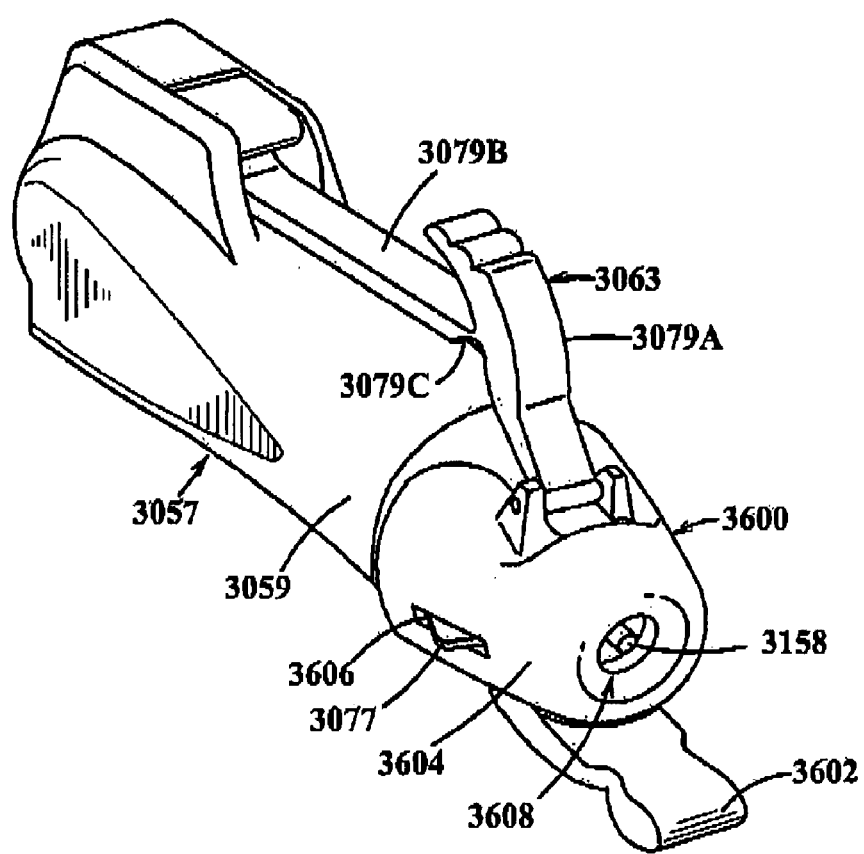
FIG. 58 is a perspective view of the cartridge and eyelid depressor of FIG. 56.

FIGS. 56-58 are views of the cartridge with another cap 3600 having an integral eyelid depressor 3602. The cap 3600 is similar to the cap 3500 (FIGS. 54-55) except for the design of the eyelid depressor 3602. Otherwise, reference numerals preceded by the numerals "36" instead of the numeral "35" indicate similar elements. As can be seen, the eyelid depressor 3602 is spaced closer to the nozzle than in the previous embodiment. As may be recognized by those of ordinary skill in the pertinent art based on the teachings herein, the shape, configuration and/or orientation of the eyelid depressors may be adjusted as desired to achieve, for example, patient comfort, or to ensure or otherwise facilitate delivery of a drop into a predetermined region of the eye, such as the ocular cul-de-sac.

Some other methods for providing a cartridge with an eyelid depressor are shown in FIGS. 46 and 48.

Still other methods for releasably or fixedly securing an eyelid depressor to the cartridge should be apparent to those of ordinary skill in the art in view of the description herein.

Figure 59:
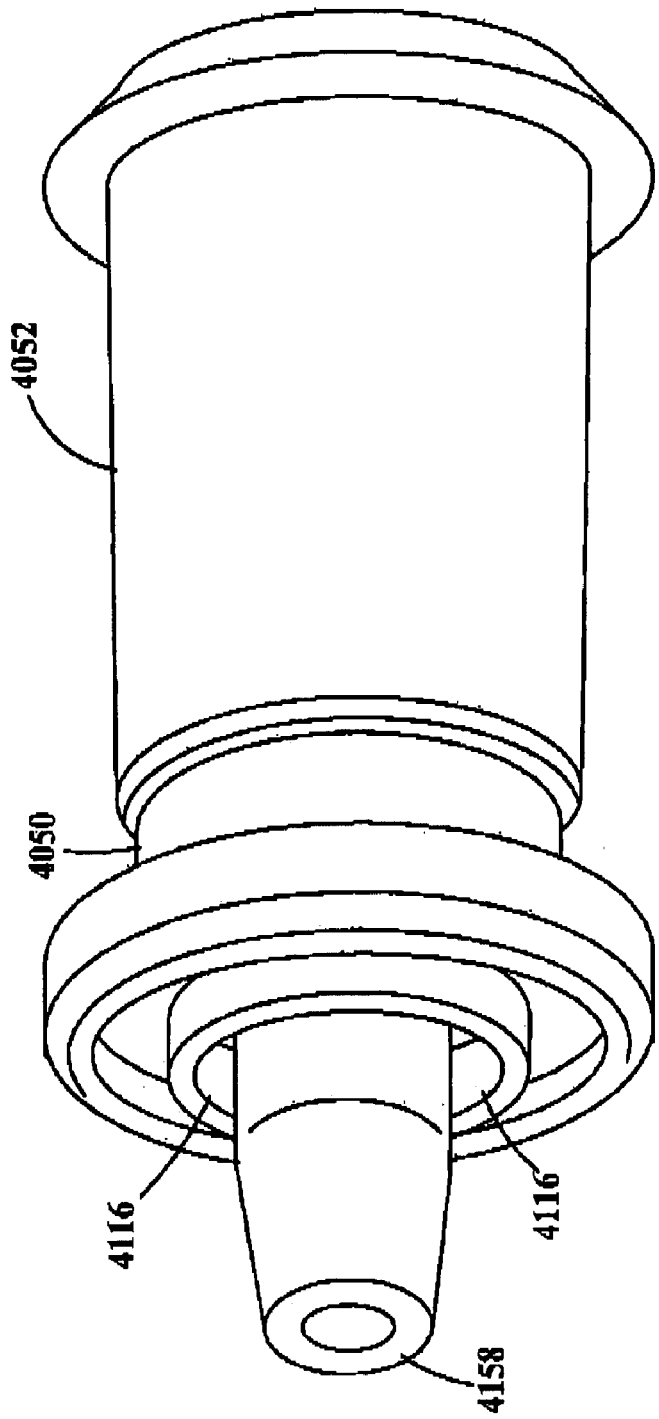
FIG. 59 is a view of one embodiment of a nozzle, piston and vial that may be used in the cartridge of FIG. 49.
Figure 60A:
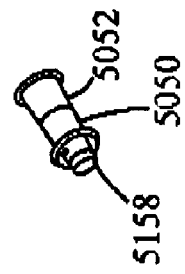
FIGS. 60A-60D are views of another embodiment of a nozzle, piston and vial that may be used in the cartridge of FIG. 49.
Figure 60D:
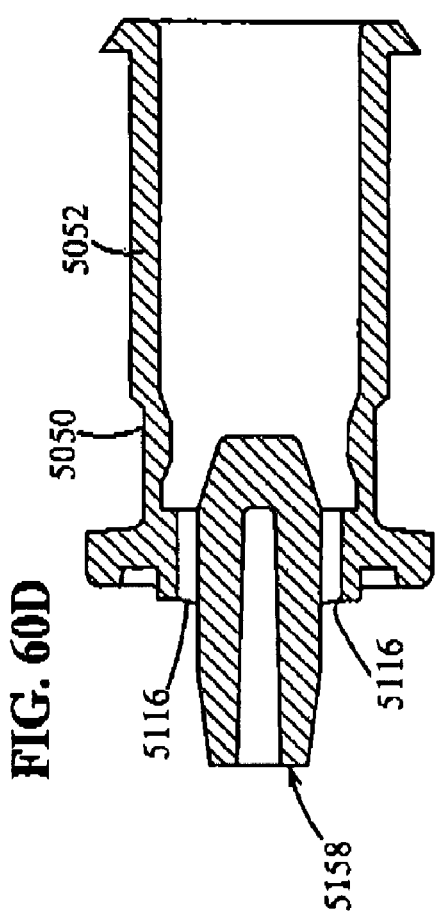
Figure 60B:
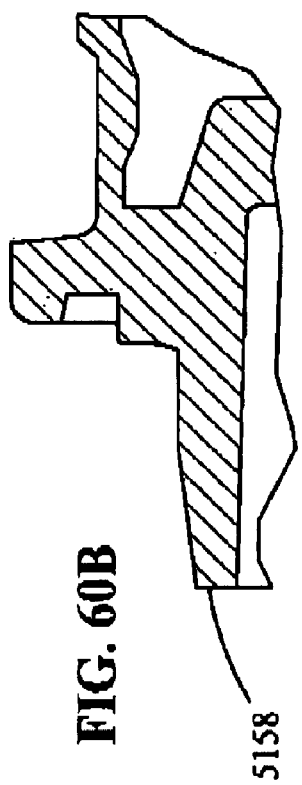
Figure 60C:
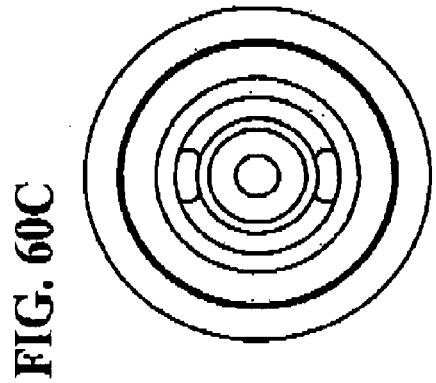

FIG. 59 shows one embodiment of a nozzle, piston and vial which may be used in the cartridge of FIG. 49. Except where otherwise noted, reference numerals preceded by the numeral "4" instead of the numeral "3" indicate similar elements. This particular embodiment has two slots 4116 for the passage of fluid or other substances therethrough. The two slots 4116 are disposed diametrically opposite one another, viewed in relation to the central bore of the nozzle 4158. This slot configuration produces a generally elongated spray pattern (i.e., the spray pattern of the medicament delivered from the apparatus has a somewhat elongated cross section).

One advantage of this slot configuration is that an elongated spray pattern better conforms to the shape of the ocular cul-de-sac, as compared to that provided by a circular spray pattern. Thus, with this slot configuration, a greater percentage of medicament may be delivered into the ocular cul-de-sac, as compared to the percentage that would be delivered to the ocular cul-de-sac by a circular spray pattern is used.

As stated above, it is often desired to direct the medicament to a particular region of the eye. In at least some embodiments, it is desirable to deliver the medicament to the cul-de-sac of the conjunctiva, sometimes referred to as the ocular cul-de-sac, which has a generally elongated shape.

When such a slot configuration is used, keying is preferably incorporated into the cartridge 3057 and/or treatment apparatus 3008 to help ensure that the generally elongated spray pattern will be generally in register with the generally elongated shape of the ocular cul-de-sac. Although not shown in FIG. 66, keying may be incorporated by providing the vial 4052, or a portion thereof, with flattened side walls that are complementary to, circumferentially aligned with, and/or abut, the flattened side walls of the cartridge casing 3059. See for example, the flattened side walls 1302 on the vial (FIGS. 39A, 39B), which narrow the width of the vial 1052 so as to enable the vial 1052 to fit within the interior cavity defined by the casing 959.

FIGS. 60A-60D are views of another embodiment of a nozzle, piston and vial that may be employed in the cartridge of FIG. 49. Except where otherwise noted, reference numerals preceded by the numeral "5" instead of the numeral "3" indicate similar elements. This embodiment also employs two diametrically opposed slots 5116 that facilitate a generally elongated spray pattern.

Other configurations for providing a generally elongated spray pattern will be apparent to those of ordinary skill in the art in view of the description herein.

Notwithstanding the advantages of a generally elongated spray pattern, it should be understood that the treatment apparatus of FIG. 49 is not limited to such spray patterns.

Note that, except where otherwise stated, phrases such as, for example, "extends radially" mean "extends in a direction that has, but is not limited to, a radial component. Consequently, the direction may be a purely radial one or one that has a radial component in addition to an axial and/or circumferential component.

Note that, except where otherwise stated, phrases such as, for example, "connected to" mean "connected directly to" or "connected indirectly to". Thus, except where otherwise stated, "coupled to" means "coupled directly to" or "coupled indirectly to".

Also note that, except where otherwise stated, terms such as, for example, "comprises", "has", "includes", and all forms thereof, are considered open-ended, so as not to preclude additional elements and/or features.

As may be recognized by those of ordinary skill in the pertinent art based on the teachings herein, numerous changes and modifications may be made to the above-described and other embodiments of the present invention without departing from the spirit of the invention as defined in the claims. For example, the components of the dispensers may be made of any of numerous different materials that are currently or later become known for performing the functions of such components. Similarly, the components of the dispensers may take any of numerous different shapes and/or configurations. Also, the dispensers may be used to dispense any of numerous different types of fluids or other substances for any of numerous different applications, including, for example, ophthalmic, nasal, dermatological, or other pharmaceutical or OTC applications. Further, the sterile filling machine used to fill the dispensers of the present invention may take any of numerous different configurations that are currently, or later become known for filling the dispensers. For example, the filling machines may have any of numerous different mechanisms for sterilizing, feeding, evacuating and/or filling the dispensers. In addition, the dispensers may incorporate any of numerous different features to accommodate any of such filling machines and/or methods. Further, the pump and/or dispensing valve each may take a configuration that is different than that disclosed herein. Accordingly, this detailed description of currently preferred embodiments is to be taken in an illustrative, as opposed to a limiting sense.

What is claimed is:

1. An ophthalmic dispenser comprising:
    a housing;
    a trigger coupled to the housing;
    a self contained cartridge disposable within the housing and comprising:
        a body defining a fluid reservoir;
        a pump coupled in fluid communication with the reservoir and defining a compression chamber, the pump being movable between (i) a first actuated position, and (ii) a rest position;
        a nozzle comprising a valve including an annular, axially-extending valve seat, an outlet aperture coupled in fluid communication between the valve seat and the compression chamber, and a flexible valve cover extending about the valve seat and forming an annular, axially-extending interface therebetween, wherein the interface is connectable in fluid communication with the outlet aperture, and at least part of the valve cover is movable between (i) a normally closed position with the valve cover engaging the valve seat to close the interface and form a fluid-tight seal therebetween, and (ii) an open position with at least part of the valve cover spaced away from the valve seat in response to fluid flowing through the outlet aperture at a pressure greater than a valve opening pressure to allow the passage of pressurized fluid therebetween; and
    an actuator coupled to the cartridge and drivingly connected between the trigger and the pump, the actuator having a spring formed integrally therewith, wherein in a first phase of actuation, the trigger is manually engaged to cause the actuator to actuate the pump from the rest position to the first actuated position, and in a second phase of actuation, the trigger is released to cause the pump to return to the rest position, whereby during actuation, the pump pressurizes fluid in the compression chamber and, in turn, dispenses a metered dosage of fluid through the valve and into a user's eye.

2. An ophthalmic dispenser as defined in claim 1, wherein the pump includes a slide defining an axially-elongated passageway and a piston slidably received within the axially-elongated passageway, wherein the slide defines within the axially-elongated passageway a compression zone, a first portion formed between the compression zone and the reservoir, and a second portion located on an opposite side of the compression zone relative to the first portion, wherein the first portion is defined by a first radius and the compression zone is defined by a second radius that is less than the first radius, and at least one of the piston and slide is movable relative to the other between (i) the first actuated position with the tip of the piston received within the first portion of the slide, and the compression zone coupled in fluid communication with the reservoir for receiving fluid therefrom, and (ii) the rest position with a tip of the piston received within the second portion of the slide, and the spring is drivingly connected to at least one of the piston and slide for moving at least one of the piston and slide relative to the other.

3. An ophthalmic dispenser as defined in claim 1, wherein the pump defines an elongated axis, and the actuator defines a path of movement transverse to the elongated axis of the pump.

4. An ophthalmic dispenser as defined in claim 2, wherein the actuator includes a lever arm drivingly connected between the trigger and at least one of the piston and slide for moving at least one of the piston and slide from the rest position to the first actuated position in response to movement of the trigger.

5. An ophthalmic dispenser as defined in claim 4, wherein the spring is formed integral with the lever arm.

6. An ophthalmic dispenser as defined in claim 5, wherein the spring is defined by a curvilinear end portion of the lever arm that engages the body for moving the body and, in turn, at least one of the piston and slide from the first actuated position to the rest position.

7. An ophthalmic dispenser as defined in claim 2, wherein one of the piston tip and the compression zone of the slide is softer than the other, and the piston tip and compression zone form an interference fit to thereby form a fluid-tight seal therebetween.

8. An ophthalmic dispenser as defined in claim 1, wherein the volume of the compression chamber is approximately equal to the volume of the metered dosage of fluid dispensed through the valve.

9. An ophthalmic dispenser as defined in claim 2, wherein in the rest position the piston tip is located in the second portion of the slide and the outlet aperture is coupled in fluid communication with the reservoir to reduce the pressure between the outlet aperture and the compression zone and allow closure of the valve.

10. An ophthalmic dispenser as defined in claim 2, wherein at least one of the piston and the slide is movable relative to the other between (i) the rest position with the piston tip located in the second portion of the slide; (ii) the first actuated position with the piston tip located in the first portion of the slide and the compression zone coupled in fluid communication with the reservoir for receiving fluid therefrom; (iii) a second actuated position with the piston tip located in the compression zone, a fluid tight seal formed between the piston tip and compression zone to pressurize the fluid in the compression zone to a pressure greater than the valve opening pressure and, in turn, cause the pressurized fluid to open the valve and dispense through the valve; and (iv) the rest position with the piston tip located in the second portion of the slide and the outlet aperture coupled in fluid communication with the reservoir to reduce the pressure between the outlet aperture and the compression zone and allow closure of the valve.

11. An ophthalmic dispenser comprising:
a body defining a fluid reservoir;
a pump coupled in fluid communication with the reservoir and including a slide defining an axially-elongated passageway and a piston slidably received within the axially-elongated passageway, wherein the slide defines within the axially-elongated passageway a compression zone, a first portion formed between the compression zone and the reservoir, and a second portion located on an opposite side of the compression zone relative to the first portion, wherein the first portion is defined by a first radius and the compression zone is defined by a second radius that is less than the first radius, and at least one of the piston and slide is movable relative to the other between (i) a first actuated position with the tip of the piston received within the first portion of the slide, and the compression zone coupled in fluid communication with the reservoir for receiving fluid therefrom, and (ii) a rest position with a tip of the piston received within the second portion of the slide;
a nozzle comprising a valve including an annular, axially-extending valve seat, an outlet aperture coupled in fluid communication between the valve seat and the compression zone, and a flexible valve cover extending about the valve seat and forming an annular, axially-extending interface therebetween, wherein the interface is connectable in fluid communication with the outlet aperture, and at least part of the valve cover is movable between (i) a normally closed position with the valve cover engaging the valve seat to close the interface and form a fluid-tight seal therebetween, and (ii) an open position with at least part of the valve cover spaced away from the valve seat in response to fluid flowing through the outlet aperture at a pressure greater than a valve opening pressure to allow the passage of pressurized fluid therebetween, wherein the nozzle defines a stop surface that contacts the piston tip in the rest position, and the surfaces of the piston tip and stop surface cooperate to define substantially zero volume within the second portion of the slide when the piston tip is in the rest position; and
a manually engageable actuator drivingly connected to at least one of the piston and slide, wherein the actuator is manually engageable to drive at least one of the piston and the slide from the first actuated position to the rest position to pressurize fluid in the compression zone and, in turn, dispense a metered dosage of fluid through the valve and into a user's eye.

12. An ophthalmic dispenser as defined in claim 11, wherein the stop surface defines a first morphology, and the piston tip defines a second morphology substantially conforming to the first morphology.

13. An ophthalmic dispenser as defined in claim 12, wherein the nozzle defines a single, angularly extending outlet aperture.

14. An ophthalmic dispenser as defined in claim 13, further comprising an eyelid depressor for engaging the facial tissue adjacent to an eye and lowering the eyelid to expose the ocular cul-de-sac upon delivering a metered dosage thereto, and wherein the outlet aperture of the nozzle is aligned with the eyelid depressor for delivering the metered dosage to the exposed ocular cul-de-sac.

15. An ophthalmic dispenser for dispensing a fluid, the dispenser comprising:
a housing;
a trigger coupled to the housing;
an eyelid depressor operatively coupled to the trigger and engageable with facial tissue adjacent to a user's eye for moving the tissue and, in turn, lowering the adjacent eyelid; and
a self contained cartridge disposable within the housing and comprising:
a vial, the vial including an interior, variable volume, fluid receiving chamber defined therein;

a pump in fluid communication with the fluid receiving chamber for pumping a fluid received therein from the dispenser, the pump defining a compression chamber and being engageable movable between (i) a first actuated position, and (ii) a rest position;

a nozzle disposed in fluid communication with the pump for allowing the passage of the pumped fluid therethrough, the nozzle comprising a valve seat and a flexible valve cover extending about the valve seat and forming an annular, axially-extending interface therebetween, wherein the interface is connectable in fluid communication with the compression chamber, and at least part of the valve cover is movable between (i) a normally closed position with the valve cover engaging the valve seat to close the interface and form a fluid-tight seal therebetween, and (ii) an open position with at least part of the valve cover spaced away from the valve seat in response to fluid flowing from the compression chamber at a pressure greater than a valve opening pressure to allow the passage of pressurized fluid therebetween;

a casing that retains the nozzle, the pump, and the vial arranged in that order along a longitudinal axis moving in a direction toward a posterior end of the dispenser, the casing having an anterior wall with an aperture for receiving the nozzle; and an actuator coupled to the casing and responsive to the trigger, the actuator defining a spring formed integrally therewith and being operatively coupled to at least one of the pump and the vial, wherein in a first phase of actuation, the trigger is manually engaged to cause the actuator to actuate the pump from the rest position to the first actuated position, and in a second phase of actuation, the trigger is released to cause the pump to return to the rest position, whereby during actuation, the actuator pressurizes fluid in the compression chamber and, in turn, dispenses a metered dosage of fluid through the valve and into a user's eye.

16. An ophthalmic dispenser as defined in claim 15, wherein the cartridge includes two main portions that are integrally formed and joined to one another to form the casing.

17. An ophthalmic dispenser as defined in claim 15, wherein the actuator has a first end and a second end, the first end being pivotably mounted to the casing, the second end being operatively coupled to the pump, the actuator further having a pivot disposed between the first end and the second end.

18. An ophthalmic dispenser as defined in claim 15, wherein the casing further has a longitudinally extending portion having an inner surface that is substantially conformal with a longitudinally extending portion of the vial.

19. An ophthalmic dispenser as defined in claim 15, wherein the vial, pump and the nozzle form part of a fluid storage and delivery system, the fluid storage and delivery system having an outer envelope defining a shape, and wherein the casing has an outer envelope defining a shape that is substantially the same as the shape defined by the outer envelope of the fluid storage and delivery system.

20. An ophthalmic dispenser for dispensing a fluid, the dispenser comprising:

a housing;

a trigger coupled to the housing;

an eyelid depressor operatively coupled to the trigger and engageable with facial tissue adjacent to a user's eye for moving the tissue and, in turn, lowering the adjacent eyelid; and a self contained replaceable cartridge disposable within the housing and having:

a posterior portion including a vial, the vial including an interior fluid receiving chamber defined therein;

a pump in fluid communication with the fluid receiving chamber for pumping an ophthalmic fluid received therein from the dispenser, the pump defining a compression chamber and being movable between (i) a first actuated position, and (ii) a rest position;

a nozzle disposed in fluid communication with the pump for allowing the passage of the pumped fluid therethrough, the nozzle comprising a valve including a valve seat and a flexible valve cover extending about the valve seat and forming an annular, axially-extending interface therebetween, wherein the interface is connectable in fluid communication with the compression chamber, and at least part of the valve cover is movable between (i) a normally closed position with the valve cover engaging the valve seat to close the interface and form a fluid-tight seal therebetween, and (ii) an open position with at least part of the valve cover spaced away from the valve seat in response to fluid flowing from the compression chamber at a pressure greater than a valve opening pressure to allow the passage of pressurized fluid therebetween;

a casing that retains the nozzle, the pump, and the posterior portion arranged in that order along a longitudinal axis moving in a direction toward a posterior end of the dispenser, the casing having an anterior wall with an aperture for receiving the nozzle; and an actuator operatively coupled to the trigger, pump and eyelid depressor, wherein in a first phase of actuation, the trigger is manually engaged to cause the actuator to actuate the pump from the rest position to the first actuated position, and to move the eyelid depressor to, in turn, lower an adjacent eyelid, whereby during actuation, the actuator pressurizes fluid in the compression chamber and, in turn, dispenses a metered dosage of fluid through the valve and into a user's eye, and in a second phase of actuation, the trigger is released to cause the pump to return to the rest position.

21. An ophthalmic dispenser as defined in claim 20, wherein the cartridge has two main portions that are integrally formed and joined to one another to form the casing.

22. An ophthalmic dispenser as defined in claim 21, wherein the casing further has a longitudinally extending portion having an inner surface that is substantially conformal with a longitudinally extending portion of the vial.

23. An ophthalmic dispenser as defined in claim 20, wherein the vial, pump and the nozzle form part of a fluid storage and delivery system, the fluid storage and delivery system having an outer envelope defining a shape, and wherein the casing has an outer envelope defining a shape that is substantially the same as the shape defined by the outer envelope of the fluid storage and delivery system.

24. An ophthalmic dispenser for dispensing a fluid, the dispenser comprising:

a housing;

a trigger coupled to the housing;

a cartridge disposable within the housing and having:

a vial, the vial including an interior fluid receiving chamber defined therein;

a pump in fluid communication with the fluid receiving chamber and defining a compression chamber, for pumping an ophthalmic fluid received therein from the dispenser;

a nozzle disposed in fluid communication with the pump for allowing the passage of the pumped fluid therethrough;

a spring portion disposed posterior to said interior fluid receiving chamber defined therein;

a casing that retains the nozzle, the pump, and the vial arranged in that order along a longitudinal axis moving in a direction toward a posterior end of the dispenser, the casing having an anterior wall with an aperture for receiving the nozzle; and an actuator formed integral with the spring and operatively coupled to the pump and to the trigger, wherein in a first phase of actuation, the trigger is manually engaged to cause the actuator to move the pump along the longitudinal axis in a direction toward the posterior end of the casing thereby applying force to the interior fluid receiving chamber and compressing the spring, and in a second phase of actuation, the trigger is released and the compressed spring applies a force to help propel the pump in a direction toward the anterior end of the casing.

25. An ophthalmic dispenser for dispensing a fluid, the dispenser comprising:

a housing;

a trigger coupled to the housing;

a self contained replaceable cartridge disposable within the housing and having:

a vial, the vial including an interior fluid receiving chamber defined therein;

a pump in fluid communication with the fluid receiving chamber and defining a compression chamber for pumping an ophthalmic fluid received therein from the dispenser;

a nozzle disposed in fluid communication with the pump for allowing the passage of the pumped fluid therethrough, the nozzle comprising a valve including a valve seat and a flexible valve cover extending about the valve seat and forming an annular, axially-extending interface therebetween, wherein the interface is connectable in fluid communication with the compression chamber, and at least part of the valve cover is movable between (i) a normally closed position with the valve cover engaging the valve seat to close the interface and form a fluid-tight seal therebetween, and (ii) an open position with at least part of the valve cover spaced away from the valve seat in response to fluid flowing from the compression chamber at a pressure greater than a valve opening pressure to allow the passage of pressurized fluid therebetween;

a casing that retains the nozzle, the pump, and the vial, the casing having an anterior wall with an aperture for receiving the nozzle; and an actuator being operatively coupled to the trigger and the pump and having a spring formed integral therewith, wherein in a first phase of actuation, the trigger is manually engaged to cause the actuator to actuate the pump from the rest position to the first actuated position, and in a second phase of actuation, the trigger is released to cause the pump to return to the rest position, whereby during actuation, the actuator pressurizes fluid in the compression chamber and, in turn, dispenses a metered dosage of fluid through the valve and into a user's eye.

26. An ophthalmic dispenser as defined in claim 25, wherein the cartridge has two main portions that are integrally fanned and joined to one another to form the casing.

27. An ophthalmic dispenser as defined in claim 26, wherein the casing further has a longitudinally extending portion having an inner surface that is substantially conformal with a longitudinally extending portion of the vial.

28. An ophthalmic dispenser as defined in claim 25, wherein the vial, pump and the nozzle form part of a fluid storage and delivery system, the fluid storage and delivery system having an outer envelope defining a shape, and wherein the casing has an outer envelope defining a shape that is substantially the same as the shape defined by the outer envelope of the fluid storage and delivery system.

29. An ophthalmic dispenser comprising:

a housing;

a trigger coupled to the housing;

a self contained cartridge disposable within the housing and comprising:

first means for forming a fluid reservoir;

a pump coupled in fluid communication with the reservoir and including a passageway and second means for pumping fluid within the passageway, wherein the pump defines within the passageway a compression chamber, the pump being engageable between (i) a first actuated position and (ii) a rest position;

a nozzle comprising a valve including an annular, axially-extending valve seat, an outlet aperture coupled in fluid communication between the valve seat and the compression chamber, and a flexible valve cover extending about the valve seat and forming an annular, axially-extending interface therebetween, wherein the interface is connectable in fluid communication with the outlet aperture, and at least part of the valve cover is movable between (i) a normally closed position with the valve cover engaging the valve seat to close the interface and form a fluid-tight seal therebetween, and (ii) an open position with at least part of the valve cover spaced away from the valve seat in response to fluid flowing through the outlet aperture at a pressure greater than a valve opening pressure to allow the passage of pressurized fluid therebetween; and an actuator coupled to the cartridge and drivingly connected between the trigger and the pump, the actuator having a spring formed integrally therewith, wherein in a first phase of actuation, the trigger is manually engaged to cause the actuator to actuate the pump from the rest position to the first actuated position, and in a second phase of actuation, the trigger is released to cause the pump to return to the rest position, whereby during actuation, the pump pressurizes fluid in the compression chamber to dispense fluid through the valve and into a user's eye.

30. An ophthalmic dispenser as defined in claim 29, further comprising third means for biasing at least one of the second means and axially-elongated passageway relative to the other.

31. An ophthalmic dispenser as defined in claim 30, wherein the pump defines an elongated axis, and the actuator defines a path of movement transverse to the elongated axis of the pump.

32. An ophthalmic dispenser as defined in claim 30, wherein the third means is defined by a flexible, curvilinear portion of the actuator engaging the first means for moving the first means and, in turn, at least one of the second means and axially-elongated passageway relative to the other.

33. An ophthalmic dispenser as defined in claim 30, wherein the third means is formed by the actuator.

34. An ophthalmic dispenser as defined in claim 29, wherein the actuator includes a lever arm drivingly connected to at least one of the first means and the pump, wherein the lever arm is engageable by the trigger for moving at least one of the second means and axially-elongated passageway relative to the other.

35. An ophthalmic dispenser as defined in claim 29, further comprising an eyelid depressor engageable with facial tissue adjacent to user's eye for moving the tissue and, in turn, lowering the adjacent eyelid, and wherein the actuator is drivingly connected to both the eyelid depressor and at least one of the first means and the pump for substantially simultaneously actuating the eyelid depressor and the pump.

36. An ophthalmic dispenser comprising:
first means for forming a fluid reservoir;
a pump coupled in fluid communication with the reservoir and including an axially-elongated passageway and second means for pumping fluid within the axially-elongated passageway, wherein the pump defines within the axially-elongated passageway a compression zone, a first portion formed between the compression zone and the reservoir, and a second portion located on an opposite side of the compression zone relative to the first portion, wherein the first portion is defined by a first dimension and the compression zone is defined by a second dimension that is less than the first dimension, and at least one of the second means and axially-elongated passageway is movable relative to the other between (i) a first actuated position wherein the second means is received within the first portion of the axially-elongated passageway, and the compression zone is coupled in fluid communication with the reservoir for receiving fluid therefrom, and (ii) a rest position wherein the second means is received within the second portion of the axially-elongated passageway:
a nozzle comprising a valve including an annular, axially-extending valve seat, an outlet aperture coupled in fluid communication between the valve seat and the compression zone, and a flexible valve cover extending about the valve seat and forming an annular, axially-extending interface therebetween, wherein the interface is connectable in fluid communication with the outlet aperture, and at least part of the valve cover is movable between (i) a normally closed position with the valve cover engaging the valve seat to close the interface and form a fluid-tight seal therebetween, and (ii) an open position with at least part of the valve cover spaced away from the valve seat in response to fluid flowing through the outlet aperture at a pressure greater than a valve opening pressure to allow the passage of pressurized fluid therebetween; and
a manually engageable actuator including a trigger, and a lever arm drivingly connected to at least one of the first means and the pump, wherein the lever arm is engageable by the trigger for moving at least one of the second means and the axially-elongated passageway from the first actuated position to the rest position and, in turn, pressurizing fluid in the compression zone to dispense fluid through the valve and into a user's eye.
wherein the lever arm defines at least one of (1) a flexible, curvilinear body that is flexibly movable radially and axially with movement of the trigger, and (2) a first arm portion, a second arm portion, and a living hinge flexibly connecting the first and second arm portions to each other and permitting radial and axial movement of the first and second arm portions with movement of the trigger.

* * * * *